(12) United States Patent
Pekari et al.

(10) Patent No.: US 7,714,136 B2
(45) Date of Patent: May 11, 2010

(54) TETRAHYDROPYRIDOTHIOPHENES

(75) Inventors: Klaus Pekari, Mittelbiberach (DE); Mathias Schmidt, Constance (DE); Thomas Bär, Reichenau (DE); Thomas Beckers, Constance (DE); Petra Gimmnich, Constance (DE)

(73) Assignee: 4SC AG, Planegg Martinsrid (DE)

( * ) Notice: Subject to any disclaimer, the term of this patent is extended or adjusted under 35 U.S.C. 154(b) by 92 days.

(21) Appl. No.: 11/920,572

(22) PCT Filed: May 24, 2006

(86) PCT No.: PCT/EP2006/062613

§ 371 (c)(1),
(2), (4) Date: Dec. 4, 2007

(87) PCT Pub. No.: WO2006/125813

PCT Pub. Date: Nov. 30, 2006

(65) Prior Publication Data

US 2008/0206258 A1    Aug. 28, 2008

(30) Foreign Application Priority Data

May 25, 2005 (EP) ................... 05104499
Dec. 14, 2005 (EP) ................... 05112150

(51) Int. Cl.
*C07D 471/02* (2006.01)
(52) U.S. Cl. .................................... 546/114
(58) Field of Classification Search ............. 546/114
See application file for complete search history.

(56) References Cited

U.S. PATENT DOCUMENTS

| | | | |
|---|---|---|---|
| 3,449,439 A | 6/1969 | Kuhnen et al. | |
| 4,963,559 A | 10/1990 | Suzuki | |
| 5,422,335 A | 6/1995 | Hagen et al. | |
| 6,069,620 A | 5/2000 | Nakamura et al. | |
| 2003/0218593 A1 | 11/2003 | Inoue et al. | |
| 2003/0232994 A1 | 12/2003 | Lu et al. | |
| 2004/0171603 A1 | 9/2004 | Pato et al. | |
| 2004/0209943 A1 | 10/2004 | Erickson et al. | |
| 2005/0154024 A1 | 7/2005 | Bryans et al. | |

FOREIGN PATENT DOCUMENTS

| | | |
|---|---|---|
| DE | 272078 A | 9/1989 |
| DE | 4039734 A | 6/1995 |
| WO | WO 9427969 | 12/1994 |
| WO | WO 98/02440 | 1/1998 |
| WO | WO 00/14090 * | 8/1999 |
| WO | 99046267 A1 | 9/1999 |
| WO | WO 0014090 | 3/2000 |
| WO | WO 0247762 | 6/2002 |
| WO | WO 02/092076 | 11/2002 |
| WO | 03080607 A1 | 10/2003 |
| WO | WO 03080607 | 10/2003 |
| WO | WO 03084947 | 10/2003 |
| WO | WO 03102153 | 12/2003 |
| WO | 2004024065 A2 | 3/2004 |
| WO | 2004024066 A2 | 3/2004 |
| WO | 2004069149 A2 | 8/2004 |
| WO | WO 2004/065351 | 8/2004 |
| WO | 2004092156 A1 | 10/2004 |
| WO | WO 2005023818 | 3/2005 |
| WO | 2005030770 A1 | 4/2005 |
| WO | 2005033102 A2 | 4/2005 |
| WO | WO 2005/044008 | 5/2005 |
| WO | 2005060711 A2 | 7/2005 |
| WO | 2005118071 A2 | 12/2005 |
| WO | 2005118592 A2 | 12/2005 |
| WO | 2005120642 A2 | 12/2005 |
| WO | WO 2006/14135 | 2/2006 |
| WO | 2006084869 A1 | 8/2006 |
| WO | 2006084904 A1 | 8/2006 |
| WO | WO 2006/125813 | 11/2006 |
| WO | WO 2006/125815 | 11/2006 |
| WO | WO 2008020045 | 12/2007 |

OTHER PUBLICATIONS

Database Chemcats, Columbus, Ohio, U.S., XP 002377744, 2 pages, which is the same as Sep. 3, 2007-SciFinder pp. 1 and 2.
Chemical Abstracts, CAS RN 724704-04-5 CAS RN 724704-02-3 XP 002336416, 10 pages.
Database Chemcats, Chemical Abstracts Service, Columbus, Ohio, U.S; XP002303659; Abstract and "Ambinter Screening Library", Jan. 1, 2004.
Database Chemcats, Chemical Abstracts Service, Columbus, Ohio, U.S; XP002369767; Abstract and "Interchim Intermediates", Jan. 18, 2005.
Database Chemcats, Chemical Abstracts Service, Columbus, Ohio, U.S; XP002369768; Abstract and "Ambinter Stock Screening Collection", Jul. 3, 2005.
Database Chemcats, Chemical Abstracts Service, Columbus, Ohio, U.S; XP002303660; Abstract and "TimTec Overseas Stock", Jun. 1, 2004.
Database Chemcats, Chemical Abstracts Service, Columbus, Ohio, U.S; XP002361377 Abstract and "Ambinter Screening Library", Jan. 1, 2004.
Sensfuss, U. et al., "2-Aminothiophenes from Triacetonamine: A Convenient Way to Novel Sterically Hindered Piperidine Derivatives," Heteroatom Chemistry, vol. 9, No. 6, pp. 529-536 (1998).

(Continued)

*Primary Examiner*—D. Margaret Seaman
*Assistant Examiner*—Nizal S Chandrakumar
(74) *Attorney, Agent, or Firm*—Millen, White, Zelano & Branigan, P.C.

(57) ABSTRACT

Compounds of a certain formula (I)

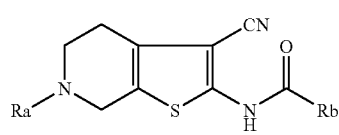

(I)

in which Ra and Rb have the meanings indicated in the description, are novel effective compounds with anti-proliferative and apoptosis inducing activity.

16 Claims, No Drawings

OTHER PUBLICATIONS

Sensfuss, U. et al., "An unusual Cascade Reaction Yielding Ortho-Peri-Fused Thienopyridopyrimidines," Heterocycles, vol. 55, No. 1, pp. 171-180 (2001).

Charette, A. Janes, M. Lebel, H., "Bis(oxazoline) copper(I)-catalyzed enantioselective cyclopropanation of cinnamate esters with diazomethane," Tetrahedron: Asymmetry, vol. 14, pp. 867-872 (2003).

Lyle, M., Wilson, P., "Synthesis of a New Chiral Nonracemic C2-Symmetric 2,2'-Bipyridyl Ligand and Its Application in Copper (I)-Catalyzed Enantioselective Cyclopropanation Reactions," Organic Letters, vol. 6, No. 5, pp. 855-857.

Chemcats, Interchim Intermediates—XP-002361378—"Thieno{2,3-c]pyridine-6(5H)-carboxylic acid, 2-[(3-chlorobenzoyl)amino]-3-cyano-4,7-dihydroethyl ester" pp. 1-5.

Non-Final Office Action dated Jun. 19, 2008 in related U.S. Appl. No. 11/597,556 filed Nov. 26, 2007. (US-2007-0213360-A1).

Non-Final Office Action dated Oct. 8, 2008 in related U.S. Appl. No. 11/883,596 filed Sep. 17, 2007. (US-2008-0096914-A1).

Non-Final Office Action dated Oct. 8, 2008 in related U.S. Appl. No. 11/628,369 filed Dec. 4, 2006. (US-2007-0259911-A1).

Non-Final Office Action dated Jun. 25, 2008 in related U.S. Appl. No. 11/597,142 filed Nov. 20, 2006. (US-2007-0244112-A1).

Non-Final Office Action dated Jun. 3, 2009 in related U.S. Appl. No. 12/411,486 filed Mar. 26, 2009.

Non-Final Office Action dated Jun. 4, 2009 in related U.S. Appl. No. 12/390,827 filed Feb. 23, 2009.

Ashimori, A., et al., "Novel 1,4-Dihydropyridine Calcium Antagonists. I. Synthesis and Hypotensive Activity of 4-(Substituted Pyridyl)-1,4-dihydropyridine Derivatives," A. Chem. Pharm. Bull., vol. 38, pp. 2446-2458 (1990).

Castanedo, G., and Sutherlin, D., "Synthesis of tetrasubstituted thiopenes on solid-support using the Gewald reaction," Tetrahedron Letters, vol. 42, pp. 7181-7184 (2001).

Interchim, Chemcats; Interchim Intermediates, Chemical Name: Benzenepropanamide, N-(6-acetyl-3-cyano-4,5,6,7-tetrahydrothieno[2,3-c]pyridin-2-yl)-; CAS Registry No. 864859-05-2; Web: http://www.interchim.com, Publication Date: Jan. 18, 2005.

Ezquerra, J., Prieto, L., Avendano, C., Martos, J., De La Cuesta, E., "Asymetric Michael Addition Reactions Using Ethyl (S)-4,4-Dimethylpyroglutamate as a Chiral Auxiliary," Tetrahedron Letters, vol. 40, pp. 1575-1578 (1999).

Fujita, M., Seki, T. and Ikeda, N., "Synthesis and Bioactivities of Novel Bicyclic Thiophenes and 4,5,6,7-Tetrahydrothieno[2,3-c]pyridines as Inhibitors of Tumor Necrosis Factor-alpha (TNF-alpha) Production," Bioorganic & Medicinal Chemistry Letters, vol. 12, pp. 1897-1900 (2002).

Huang, K. and Huang, Z., "A Practical and Controllable Enantioselective Synthesis of 2-Phenyl-1-cyclopropanecarboxylates via a Camphor-Derived Sulfonium Ylide," Synlett, No. 10, pp. 1621-1623 (2005).

Lindstedt, E. and Nilsson, M., "2-Thienyl as Auxiliary Group in Mixed Lithium Diorganocuprates," Acta Chemica Scandinavica, B 40, pp. 466-469 (1986).

Lipshutz, B., Servesko, J. and Taft, B., "Asymmetric 1,4-Hydrosilylations of alpha,beta-Unsaturated Esters," J. Am. Chem. Soc., vol. 126, pp. 8352-8353 (2004).

Sainsbury, M., Weerasinghe, D., and Dolman, D., Chemistry of 6H-pyrido[4,3-b]carbazoles. Part 9. An Efficient route to 3-[1-(3-Ethylpyridyl)] indoles and the Synthesis of Some New Ellipticines. J.C.S. Perkin I, pp. 587-590 (1982).

Sakuma, S., Sakai, M., Itooka, R. and Miyaura, N., "Asymmetric Conjugate 1,4-Addition of Arylboronic Acids to alpha,beta-Unsaturated Esters Catalyzed by Rhodium(I)/(S)-binap," J. Org. Chem., vol. 65, pp. 5951-5955 (2000).

Srikrishna, A., Kumar, P. and Viswajanani, R., "A Simple Strategy for Spirocyclopentannulation of Cyclic Ketones. Formal Total Synthesis of (+)-Acorone," Tetrahedron Letters, vol. 37, No. 10, pp. 1683-1686 (1996).

Tang, W., Wang, W. and Zhang, X., "Phospholane-Oxazoline Ligands for Ir-Catalyzed Asymmetric Hydrogenation," Angew. Chem. Int. Ed., vol. 42, No. 8, pp. 943-946 (2003).

Uemura, T. et al., "Highly Efficient Enantioselective Synthesis of Optically Active Carboxylic Acids by Ru(OCOCH3)2[(S)-H8-BINAP]," J. Org. Chem., vol. 61, pp. 5510-5516 (1996).

* cited by examiner

TETRAHYDROPYRIDOTHIOPHENES

This application was filed under 35 U.S.C. 371 as a national stage of PCT/EP2006/062613, filed May 24, 2006.

FIELD OF APPLICATION OF THE INVENTION

The invention relates to tetrahydropyridothiophene derivatives, which can be used in the pharmaceutical industry for the production of pharmaceutical compositions.

The invention further relates to the contribution made to the art by the finding, that said tetrahydropyridothiophene derivatives display cell-cycle dependent, anti-proliferative and apoptosis inducing activity.

The invention also relates to the use of these compounds for the therapy of hyperproliferative diseases, in particular human cancer.

KNOWN TECHNICAL BACKGROUND

Cancer chemotherapy was established with the alkylating agent Cyclophosphamide (Endoxan®), an oxazaphosphorin pro-drug activated preferentially in the tumor. The target of alkylating agents like Cyclophosphamide is DNA and the concept, that cancer cells with uncontrolled proliferation and a high mitotic index are killed preferentially, proved to be very successful. Standard cancer chemotherapeutic drugs finally kill cancer cells upon induction of programmed cell death ("apoptosis") by targeting basic cellular processes and molecules. These basic cellular processes and molecules include RNA/DNA (alkylating and carbamylating agents, platin analogs and topoisomerase inhibitors), metabolism (drugs of this class are named anti-metabolites and examples are folic acid, purin and pyrimidine antagonist) as well as the mitotic spindle apparatus with αβ-tubulin heterodimers as the essential component (drugs are categorized into stabilizing and destabilizing tubulin inhibitors; examples are Taxol/Paclitaxel®, Docetaxel/Taxotere® and vinca alkaloids).

A subgroup of proapoptotic anticancer agents target cells preferentially in mitosis. In general these agents do not induce apoptosis in non-dividing cells, arrested in the G0, G1 or G2 phase of the cell division cycle. In contrast, dividing cells going through mitosis (M-phase of the cell division cycle), are killed efficiently by induction of apoptosis by this subgroup agents. Therefore, this subgroup or class of anti-cancer agents is described as cell-cycle specific or cell-cycle dependent. Tubulin inhibitors, with Taxol (Paclitaxel®) as a prominent example, belong to this class of cell-cycle specific, apoptosis inducing anti-cancer agents.

The international application WO2004/024065 describes, inter alia, tetrahydropyridothiophene derivatives as glucagons antagonists for the treatment of diabetes.

The german document DE4039734 describes, inter alia, N-alkylated tetrahydropyridothiophene derivatives as components of herbicidal agents.

The german document DD272078 describes, inter alia, N-alkylated tetrahydropyridothiophene derivatives with anti-anaphylactic und antihistaminergic properties.

The international application WO2005/033102 describes thiophene-based compounds exhibiting ATP-utilizing enzyme inhibitory activity.

The international application WO2004/092156 describes substituted 3-cyanothiophene acetamides as glucagon receptor antagonists.

The international application WO9946267 describes 2-aminothiophene derivatives as modulators of protein tyrosine phosphatases.

The international application WO2005/060711 describes a method of treating diseases mediated by sirtuin, e.g. SirT1 mediated deacetylation, using substituted thiophene compounds.

The international application WO2005/033102 describes a method of combating phytopathogenic diseases on plants using 2-aminothiophene derivatives.

The international application WO2004/069149 describes aminosulfonyl-substituted thienopyridine derivatives which are said to be capable of inhibiting the interactions between effector cell adhesion molecules and glycosaminoglycans and thus useful for treating diseases related to cell adhesion and cell migration.

The international applications WO2005/118071, WO2005/118592 and WO2005/120642 describe tetrahydropyridothiophenes with anti-proliferative and/or apoptosis inducing activity for use in the treatment of cancer.

DESCRIPTION OF THE INVENTION

It has now been found that the tetrahydropyridothiophene derivatives, which are described in greater details below, differ from prior art compounds by unanticipated and originative structural alterations and have surprising and particularly advantageous properties.

Thus, for example, the compounds according to this invention are potent and highly efficacious inhibitors of cellular (hyper)proliferation and/or cell-cycle specific inducers of apoptosis in cancer cells.

Therefore, unanticipatedly, these compounds can be useful for treating (hyper)proliferative diseases and/or disorders responsive to the induction of apoptosis, in particular cancer. By having a cell-cycle specific mode of action, these derivates should have a higher therapeutic index compared to standard chemotherapeutic drugs targeting basic cellular processes like DNA replication or interfering with basic cellular molecules like DNA.

Thus, for example, the compounds according to this invention are expected to be useful in targeted cancer therapy.

The invention thus relates, in a first aspect (aspect a), to compounds of formula I

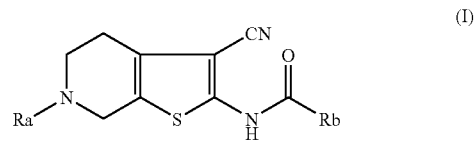

wherein
Ra is —C(O)R1, in which
R1 is 1-4C-alkyl, or 1-4C-alkyl substituted by one to four substituents independently selected from R2,
Rb is -T-Q, in which
T is 1-6C-alkylene or 3-7C-cycloalkylene, and
either
Q is optionally substituted by Rba and/or Rbb and/or Rbc, and is phenyl or naphthyl,
or
Q is optionally substituted by Rca and/or Rcb, and is Har,
or
Q is optionally substituted by Rda and/or Rdb, and is Het,
or
Q is optionally substituted by Rea and/or Reb, and is 3-7C-cycloalkyl, wherein
each R2 may be the same or different and is independently selected from the group consisting of:
3-7C-cycloalkyl, phenyl, Har, Het,
halogen, trifluoromethyl, nitro, cyano,
—C(O)R3, —C(O)OR4, —C(O)N(R5)R6, —S(O)$_2$R3, —S(O)$_2$N(R5)R6,
—N(R7)C(O)R3, —N(R7)C(O)OR4, —N(R7)C(O)N(R5)R6, guanidino,
—OC(O)R3,
completely or predominantly fluorine-substituted 1-4C-alkoxy,
—O[C(R8)R9]$_y$N(R5)R6, —O[C(R8)R9]$_y$C(O)N(R5)R6, —OR4, hydroxy-2-4C-alkoxy, 1-4C-alkoxy-2-4C-alkoxy, pyridyl-1-4C-alkoxy, (1-4C-alkoxy-2-4C-alkoxy-2-4C-alkoxy, —N(R5)R6, and —SR3,
wherein each of said 3-7C-cycloalkyl, phenyl, Har and Het is optionally substituted by one to four substituents independently selected from R10,
in which
each R3, R4, R5 and R6 may be the same or different and is each independently selected from the group consisting of:
hydrogen, 1-7C-alkyl, 3-7C-cycloalkyl, phenyl, and phenyl-1-4C-alkyl,
each R7 may be the same or different and is independently selected from the group consisting of:
hydrogen, 1-7C-alkyl, and 3-7C-cycloalkyl,
each R8 and R9 may be the same or different and is each independently selected from the group consisting of:
hydrogen, and 1-4C-alkyl,
each R10 may be the same or different is independently selected from the group consisting of:
1-4C-alkyl, phenyl,
halogen, trifluoromethyl, cyano,
1-4C-alkoxycarbonyl, carboxyl,
hydroxyl, and phenoxy,
wherein each of said phenyl and phenoxy radicals can be unsubstituted or optionally substituted by up to four halogen radicals and up to two 1-4C-alkyl, hydroxyl, trifluoromethyl or cyano radicals,
each y is 1, 2, 3 or 4,
each Rba, Rbb, Rbc, Rca, Rcb, Rda, Rdb, Rea and Reb may be the same or different and is each independently selected from the group consisting of:
1-4C-alkyl, phenyl,
halogen, trifluoromethyl, cyano,
1-4C-alkoxycarbonyl, carboxyl,
hydroxyl, and phenoxy,
wherein each of said phenyl and phenoxy can be unsubstituted or optionally substituted by up to four halogen radicals and up to two 1-4C-alkyl, hydroxyl, trifluoromethyl or cyano radicals,
each Har is the same or different and is independently any fully aromatic or partially aromatic mono- or fused bicyclic ring or ring system made up of
a first constituent being a 5- or 6-membered monocyclic unsaturated, aromatic heteroaryl ring A,
which heteroaryl ring A comprises one to four heteroatoms independently selected from nitrogen, oxygen and sulfur,
and, optionally, fused to said first constituent,
a second constituent being a benzene ring, a 5-6C-cycloalkane ring, an additional heteroaryl ring A as defined herein afore, or a heterocyclic ring B as defined herein below, whereby said Har ring or ring system is attached to the parent molecular group via a substitutable ring carbon or ring nitrogen atom,
each Het is the same or different and is independently any fully saturated or partially unsaturated mono- or fused bicyclic ring or ring system made up of
a first constituent being a 3- to 7-membered monocyclic fully saturated or partially unsaturated, non-aromatic heterocyclic ring B,
which heterocyclic ring B comprises one to three heteroatoms independently selected from nitrogen, oxygen and sulfur,
and which heterocyclic ring B is optionally substituted by one or two oxo groups,
and, optionally, fused to said first constituent,
a second constituent being a benzene ring, a 3-7C-cycloalkane ring, or an additional heterocyclic ring B as defined herein afore, whereby said Het ring or ring system is attached to the parent molecular group via a substitutable ring carbon or ring nitrogen atom;
under the proviso, that
(6-acetyl-3-cyano-4,5,6,7-tetrahydro-thieno[2,3-c]pyridin-2-yl)-3-phenyl-propionamide
is thereof disclaimed;
and the salts thereof.

1-4C-Alkyl is a straight-chain or branched alkyl radical having 1 to 4 carbon atoms. Examples are the butyl, isobutyl, sec-butyl, tert-butyl, propyl, isopropyl, and, particularly, the ethyl and methyl radicals.

1-6C-Alkylene is a straight chain or branched alkylene radical having 1 to 4 carbon atoms. Examples which may be mentioned in this context are the methylene (—CH$_2$—), ethylene (—CH$_2$—CH$_2$—), trimethylene (—CH$_2$—CH$_2$—CH$_2$—), tetramethylene (—CH$_2$—CH$_2$—CH$_2$—CH$_2$—), 1,2-dimethylethylene [—CH(CH$_3$)—CH(CH$_3$)—], 1,1-dimethylethylene [—C(CH$_3$)$_2$—CH$_2$—], 2,2-dimethylethylene [—CH$_2$—C(CH$_3$)$_2$—], isopropylidene [—C(CH$_3$)$_2$—], 1-methylethylene radical [—CH(CH$_3$)—CH$_2$—], 2-methylethylene radical [—CH$_2$—CH(CH$_3$)—], pentamethylene (—CH$_2$—CH$_2$—CH$_2$—CH$_2$—CH$_2$—) and the hexamethylene radicals (—CH$_2$—CH$_2$—CH$_2$—CH$_2$—CH$_2$—CH$_2$—), of which the 1-4C-alkylene radicals, in particular the ethylene, the 2,2-dimethylethylene, the 1-methylethylene and the 2-methylethylene radicals, are more worthy to be mentioned. In more particular worthy to be mentioned are the ethylene and the 2-methylethylene [—CH$_2$—CH(CH$_3$)—] radicals. It is to be understood, that, when T is one of those 1-6C-alkylene radicals drawn above, said radical is attached with its right terminus to the moiety Q.

3-7C-Cycloalkyl stands for cyclopropyl, cyclobutyl, cyclopentyl, cyclohexyl and cycloheptyl, of which cyclopropyl, cyclopentyl and cyclohexyl are to be emphasized.

3-7C-Cycloalkane stands for cyclopropane, cyclobutane, cyclopentane, cyclohexane and cycloheptane, of which cyclohexane and cyclopentane are to be emphasized.

5-6C-Cycloalkane stands for cyclohexane and cyclopentane.

3-7C-Cycloalkylene represents cycloalkylene radicals having 3 to 7 carbon atoms, such as cyclopropylene, cyclobutylene, cyclopentylene, cyclohexylene and cycloheptylene, of which cyclopropylene is more worthy to be mentioned, where the 1,2-cyclopropylene radical is to be emphasized.

Phenyl-1-4C-alkyl represents one of the abovementioned 1-4C-alkyl radicals, which is substituted by a phenyl radical. Examples which may be mentioned are the phenethyl and the benzyl radicals.

Halogen within the meaning of the present invention is iodine, or, particularly, bromine, chlorine and fluorine.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

2-4C-Alkoxy represents radicals which, in addition to the oxygen atom, contain a straight-chain or branched alkyl radical having 2 to 4 carbon atoms. Examples which may be mentioned are the butoxy, isobutoxy, sec-butoxy, tert-butoxy, propoxy, isopropoxy and preferably the ethoxy radical.

As completely or predominantly fluorine-substituted 1-4C-alkoxy, for example, the 2,2,3,3,3-penta-fluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals may be mentioned. "Predominantly" in this connection means that more than half of the hydrogen atoms of the 1-4C-alkoxy radicals are replaced by fluorine atoms.

1-4C-Alkoxy-2-4C-alkoxy represents 2-4C-alkoxy radicals, which are substituted by one of the abovementioned 1-4C-alkoxy radicals. Examples which may be mentioned are the methoxyethoxy, ethoxyethoxy and the isopropoxyethoxy radicals, particularly the 2-methoxyethoxy, 2-ethoxyethoxy and the 2-isopropoxyethoxy radicals.

Phenyl-1-4C-alkoxy represents one of the abovementioned 1-4C-alkoxy radicals, which is substituted by a phenyl radical. Examples which may be mentioned are the phenethoxy and the benzyloxy radicals.

Pyridyl-1-4C-alkoxy represents one of the abovementioned 1-4C-alkoxy radicals, which is substituted by a pyridyl radical. Examples which may be mentioned are the 2-pyridyl-ethoxy and the pyridylmethoxy radicals.

Pyridyl-1-4C-alkyl represents one of the abovementioned 1-4C-alkyl radicals, which is substituted by a pyridyl radical. Examples which may be mentioned are the 2-pyridyl-ethyl and the pyridylmethyl radicals.

Pyridyl includes pyridin-2-yl, pyridin-3-yl and pyridin-4-yl.

(1-4C-Alkoxy-2-4C-alkoxy)-2-4C-alkoxy represents 2-4C-alkoxy radicals, which are substituted by one of the abovementioned 1-4C-alkoxy-2-4C-alkoxy radicals. Examples which may be mentioned are the 2-(2-methoxyethoxy)-ethoxy and the 2-(2-ethoxyethoxy)-ethoxy radicals.

Hydroxy-2-4C-alkoxy represents 2-4C-alkoxy radicals, which are substituted by a hydroxyl group. Examples which may be mentioned are the 2-hydroxyethoxy and the 3-hydroxypropoxy radicals. 1-4C-Alkoxycarbonyl represents a radical which, in addition to the carbonyl group, contains one of the abovementioned 1-4C-alkoxy radicals. Examples which may be mentioned are the methoxycarbonyl, the ethoxycarbonyl and the tertbutoxycarbonyl radicals.

In addition to the nitrogen atom, mono- or di-1-4C-alkylamino radicals contain one or two of the abovementioned 1-4C-alkyl radicals. Di-1-4C-alkylamino is preferred and here, in particular, dimethyl-, diethyl- or diisopropylamino.

Mono- or Di-1-4C-alkylaminocarbonyl radicals contain in addition to the carbonyl group one of the abovementioned mono- or di-1-4C-alkylamino radicals. Examples which may be mentioned are the N-methyl- the N,N-dimethyl-, the N-ethyl-, the N-propyl-, the N,N-diethyl- and the N-isopropylaminocarbonyl radical.

An 1-4C-Alkylcarbonylamino radical is, for example, the propionylamino ($C_3H_7C(O)NH$—) and the acetylamino radical ($CH_3C(O)NH$—).

1-4C-Alkylcarbonyloxy stands for a carbonyloxy group to which one of the abovementioned 1-4C-alkyl radicals is bonded. An example is the acetoxy radical ($CH_3C(O)$—O—).

1-4C-Alkylcarbonyl is a carbonyl group to which one of the abovementioned 1-4C-alkyl radicals is bonded. An example is the acetyl radical ($CH_3CO$—).

Naphthyl includes naphthalen-1-yl and naphthalen-2-yl.

Har stands for a fully aromatic or partially aromatic mono- or fused bicyclic ring or ring system made up of a first constituent being a 5- or 6-membered monocyclic unsaturated, aromatic heteroaryl ring A, which heteroaryl ring A comprises one to four heteroatoms independently selected from nitrogen, oxygen and sulfur, and, optionally, fused to said first constituent, a second constituent being a benzene ring, a 5-6C-cycloalkane ring, an additional heteroaryl ring A as defined herein afore, or a heterocyclic ring B as defined herein below in the context of the definition of Het, whereby said Har ring or ring system is attached to the parent molecular group via a substitutable ring carbon or ring nitrogen atom.

It is to be understood, that, if a radical Har contains quaternizable imino-type ring nitrogen atoms (—N=), said Har radical is not attached via said quaternizable imino-type ring nitrogen atom to the parent molecular group.

Examples for Har may include, but are not limited to, 5-membered heteroaryl radicals, such as e.g. furanyl, thiophenyl, pyrrolyl, oxazolyl, isoxazolyl, thiazolyl, isothiazolyl, imidazolyl, pyrazolyl, triazolyl, thiadiazolyl or oxadiazolyl, and 6-membered heteroaryl radicals, such as e.g. pyridinyl, pyrimidinyl, pyrazinyl or pyridazinyl, and the benzo-fused derivatives thereof such as e.g. quinazolinyl, quinoxalinyl, cinnolinyl, quinolinyl, isoquinolinyl, indolyl, isoindolyl, indazolyl, phthalazinyl, benzothiophenyl, benzofuranyl, isobenzofuranyl, benzoxazolyl, benzothiazolyl or benzimidazolyl, as well as naphthyridinyl, indolizinyl or purinyl.

When R2 is Har, a more detailed example for Har includes imidazolyl.

When R2 is Har, a further more detailed example for Har includes imidazol-1-yl.

When R2 is Har, a further more detailed example for Har includes imidazol-4-yl and, particularly, imidazol-5-yl and imidazol-2-yl.

When R2 is Har, another more detailed example for Har includes pyridinyl.

When R2 is Har, a further more detailed example for Har includes pyridin-2-yl.

When R2 is Har, another further more detailed example for Har includes pyridin-3-yl.

When R2 is Har, another further more detailed example for Har includes pyridin-4-yl.

When Q is Har, a more detailed example for Har includes pyridinyl.

When Q is Har, a further more detailed example for Har includes pyridin-2-yl.

When Q is Har, another further more detailed example for Har includes pyridin-3-yl.

When Q is Har, another more detailed example for Har includes furanyl.

When Q is Har, a further more detailed example for Har includes furan-2-yl.

When Q is Har, another further more detailed example for Har includes furan-3-yl.

When Q is Har, another more detailed example for Har includes thiophenyl.

When Q is Har, a further more detailed example for Har includes thiophen-2-yl.

When Q is Har, another further more detailed example for Har includes thiophen-3-yl.

Het stands for a fully saturated or partially unsaturated mono- or fused bicyclic ring or ring system made up of a first constituent being a 3- to 7-membered monocyclic fully saturated or partially unsaturated, non-aromatic heterocyclic ring B, which heterocyclic ring B comprises one to three heteroatoms independently selected from nitrogen, oxygen and sulfur, and which heterocyclic ring B is optionally substituted by one or two oxo groups, and, optionally, fused to said first constituent, a second constituent being a benzene ring, a 3-7C-cycloalkane group, or an additional heterocyclic ring B as defined herein afore, whereby said Het ring or ring system is attached to the parent molecular group via a substitutable ring carbon or ring nitrogen atom.

Examples for Het may include, but are not limited to, aziridinyl, azetidinyl, pyrrolidinyl, piperidinyl, homopiperidinyl, pyrazolidinyl, imidazolidinyl, piperazinyl, homopiperazinyl, morpholinyl or thiomorpholinyl, or tetrahydrofuranyl, and the partially unsaturated derivatives thereof such as e.g. pyrrolinyl, imidazolinyl or pyrazolinyl, and the oxo substituted derivatives of the aforementioned examples such as e.g. 2-oxopyrrolidinyl, 2-oxoimidazolidinyl, 2-oxopiperidinyl, 2,5-dioxopyrrolidinyl, 2,5-dioxoimidazolidinyl, 2,6-dioxopiperidinyl, 2-oxopiperazinyl, or 5-oxo-1,4-diazepanyl, and the benzo-fused derivatives of the aforementioned examples such as e.g. indolinyl, isoindolinyl, 1,2,3,4-tetrahydroquinolinyl or 1,2,3,4-tetrahydroisoquinolinyl, as well as 1,3-benzodioxolyl, 2,3-dihydro-1,4-benzodioxinyl, 2,3-dihydrobenzothiophenyl, chromenyl, chromanyl, or 2,3-dihydrobenzofuranyl.

More detailed exemplary Het radicals include those isomers of the abovementioned examples which are attached via a ring nitrogen atom, such as e.g., without being limited to, aziridin-1-yl, azetidin-1-yl, pyrrolidin-1-yl, piperidin-1-yl, homopiperidin-1-yl, piperazin-1-yl, homopiperazin-1-yl, morpholin-4-yl or thiomorpholin-4-yl.

Other more detailed exemplary Het radicals include those isomers of the abovementioned examples which are attached via a ring carbon atom, such as e.g., without being limited to, pyrrolidin-2-yl, pyrrolidin-2-yl, piperidin-2-yl, piperidin-3-yl, piperidin-4-yl or piperazin-2-yl.

Other more detailed exemplary Het radicals include those benzo-fused derivatives which are attached via the benzene ring to the parent molecular group, such as e.g. 1,3-benzodioxol-5-yl, 2,3-dihydro-1,4-benzodioxin-6-yl, 2,3-dihydrobenzothiophen-5-yl, 2,3-dihydrobenzothiophen-6-yl, chromen-6-yl, chromen-7-yl, chroman-6-yl, chroman-7-yl, 2,3-dihydrobenzofuran-5-yl, or 2,3-dihydrobenzofuranyl-6-yl.

When R2 is Het, further more detailed exemplary Het radicals include morpholino (i.e. morpholin-4-yl).

As used herein, the term "oxo" forms a carbonyl moiety when attached at a carbon atom, a sulfoxide moiety when attached to a sulfur atom and a sulfonyl moiety when two of said terms are attached to a sulfur atom.

Mono- or di-(R201)-substituted imidazol-1-yl or pyrazol-1-yl stands for an imidazol-1-yl or pyrazol-1-yl radical, respectively, which is substituted by one or two radicals independently selected from R201, such as mono- or di-methyl-substituted imidazol-1-yl or pyrazol-1-yl, respectively, like 2-methyl-imidazol-1-yl, 4-methyl-imidazol-1-yl or 5-methyl-imidazol-1-yl, or 2,4-dimethyl-imidazol-1-yl; in particular 2-methyl-imidazol-1-yl, 4-methyl-imidazol-1-yl or 2,4-dimethyl-imidazol-1-yl.

R201- and/or R202-substituted pyridyl or pyrimidinyl, respectively, may include, for example, methyl-substituted pyridyl or pyrimidinyl, respectively, like 4-methyl-pyridin-2-yl or 4-methyl-pyridin-3-yl.

1N-(1-4C-alkyl)-imidazolyl or 1N-(1-4C-alkyl)-pyrazolyl, respectively, refers to imidazolyl or pyrazolyl, respectively, which is substituted by 1-4C-alkyl on the nitrogen atom in position 1, such as e.g. 1N-methyl-imidazolyl or 1N-ethyl-imidazolyl, e.g. 1-methyl-imidazol-2-yl, 1-methyl-imidazol-5-yl or 1-ethyl-imidazol-2-yl; in particular 1-methyl-imidazol-2-yl or 1-methyl-imidazol-5-yl. R201-substituted 1N-(1-4C-alkyl)-imidazolyl or R201-substituted 1N-(1-4C-alkyl)-pyrazolyl, respectively, may include, for example, methyl- or ethyl-substituted 1N-(1-4C-alkyl)-imidazolyl or 1N-(1-4C-alkyl)-pyrazolyl, respectively, like methyl-substituted 1N-methyl-imidazolyl, e.g. 1,4-dimethylimidazol-2-yl or 1,5-dimethylimidazol-2-yl.

1N—(H)-imidazolyl or 1N—(H)-pyrazolyl, respectively, refers to imidazolyl or pyrazolyl, respectively, which is substituted by hydrogen on the nitrogen atom in position 1, such as e.g. 1H-imidazol-2-yl or 1H-imidazol-5-yl. R201-substituted 1N—(H)-imidazolyl or R101-substituted 1N—(H)-pyrazolyl, respectively, may include, for example, methyl- or ethyl-substituted 1N—(H)-imidazolyl or 1N—(H)-pyrazolyl, respectively, like methyl-substituted 1N—(H)-imidazolyl, e.g. 4-methyl-1H-imidazol-2-yl or 5-methyl-1H-imidazol-2-yl.

The term (R2)-methyl stand for methyl which is substituted by R2. The term 2-(R2)-ethyl stands for ethyl which is substituted in 2-position by R2. The term 3-(R2)-propyl stands for propyl which is substituted in 3-position by R2.

The expression (Rba)-phenyl means that the phenyl radical is substituted by Rba, which is attached to any of the positions of the phenyl ring; the expression 2-(Rba)-phenyl means that the phenyl radical is substituted by Rba, which is attached in the 2-position to the phenyl radical (i.e. the ortho position with respect to the binding position in which the phenyl ring is bonded to the parent molecular group). The expression 5-(Rca)-furan-2-yl means that the furan-2-yl radical is substituted by Rca, which is attached in the 5-position to the furan-2-yl radical; the expression 5-(Rca)-4-(Rcb)-furan-2-yl means that the furan-2-yl radical is substituted by both Rca and Rcb, whereby the substituent Rca is bonded in the 5-position to the furan-2-yl radical, and the substituent Rcb is bonded in the 4-position to the furan-2-yl radical. In this connection, further similar expressions mentioned herein indicating in short form the positions in which substituents are bonded to a ring radical are to be understood similarly, mutatis mutandis, as specified exemplarily and representatively for the foregoing expressions.

In general, unless otherwise mentioned, the radicals Har and Het include all the possible isomeric forms thereof, particularly the positional isomers thereof. Thus, for example, the term pyridinyl or pyridyl includes pyridin-2-yl, pyridin-3-yl and pyridin-4-yl, or the term thiophenyl includes thiophen-2-yl and thiophen-3-yl.

Constituents which are optionally substituted as stated herein, may be substituted, unless otherwise noted, at any possible position.

Unless otherwise mentioned, the phenyl radical may be substituted by its substituents or parent molecular groups at any possible position.

The heterocyclic groups, alone or as part of other groups, mentioned herein may be substituted by their given substituents or parent molecular groups, unless otherwise noted, at any possible position, such as e.g. at any substitutable ring carbon or ring nitrogen atom.

Unless otherwise noted, rings containing quaternizable imino-type ring nitrogen atoms (—N═) may be preferably not quaternized on these imino-type ring nitrogen atoms by the mentioned substituents or parent molecular groups.

Unless otherwise noted, any heteroatom of a heterocyclic ring with unsatisfied valences mentioned herein is assumed to have the hydrogen atom(s) to satisfy the valences.

When any variable occurs more than one time in any constituent, each definition is independent.

Suitable salts for compounds of formula I according to this invention—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to this invention on an industrial scale, are converted into pharmacologically tolerable salts by processes known to the person skilled in the art.

According to expert's knowledge the compounds of formula I according to this invention as well as their salts may contain, e.g. when isolated in crystalline form, varying amounts of solvents. Included within the scope of the invention are therefore all solvates and in particular all hydrates of the compounds of formula I according to this invention as well as all solvates and in particular all hydrates of the salts of the compounds of formula I according to this invention.

In one embodiment of this invention, salts of compounds of formula I include a salt of a compound of formula I selected from the group consisting of a hydrochloride salt, a malonate salt, a tartrate salt, (such as e.g. a D-(−)-tartrate salt or a L-(+)-tartrate salt), a maleate salt, a methanesulfonate salt and an oxalate salt.

In the context of this invention, hyperproliferation and analogous terms are used to describe aberrant/dysregulated cellular growth, a hallmark of diseases like cancer. This hyperproliferation might be caused by single or multiple cellular/molecular alterations in respective cells and can be, in context of a whole organism, of benign or malignant behaviour. Inhibition of cell proliferation and analogous terms is used herein to denote an ability of the compound to retard the growth of and/or kill a cell contacted with that compound as compared to cells not contacted with that compound. Most preferable this inhibition of cell proliferation is 100%, meaning that proliferation of all cells is stopped and/or cells undergo programmed cell death. In some preferred embodiments the contacted cell is a neoplastic cell. A neoplastic cell is defined as a cell with aberrant cell proliferation and/or the potential to metastasize to different tissue or organs. A benign neoplasia is described by hyperproliferation of cells, incapable of forming an aggressive, metastasizing tumor in-vivo. In contrast, a malignant neoplasia is described by cells with different cellular and biochemical abnormalities, e.g. capable of forming tumor metastasis. The acquired functional abnormalities of malignant neoplastic cells (also defined as "hallmarks of cancer") are replicative potential ("hyperproliferation"), self-sufficiency in growth signals, insensitivity to anti-growth signals, evasion from apoptosis, sustained angiogenesis and tissue invasion and metastasis.

Inducer of apoptosis and analogous terms are used herein to identify a compound which executes programmed cell death in cells contacted with that compound. Apoptosis is defined by complex biochemical events within the contacted cell, such as the activation of cystein specific proteinases ("caspases") and the fragmentation of chromatin. Induction of apoptosis in cells contacted with the compound might not necessarily be coupled with inhibition of cell proliferation. Preferably, the inhibition of cell proliferation and/or induction of apoptosis is specific to cells with aberrant cell growth (hyperproliferation). Thus, compared to cells with aberrant cell growth, normal proliferating or arrested cells are less sensitive or even insensitive to the proliferation inhibiting or apoptosis inducing activity of the compound. Finally, cytotoxic is used in a more general sense to identify compounds which kill cells by various mechanisms, including the induction of apoptosis/programmed cell death in a cell cycle dependent or cell-cycle independent manner.

Cell cycle specific and analogous terms are used herein to identify a compound as inducing apoptosis only in continously proliferating cells actively passing a specific phase of the cell cycle, but not in resting, non-dividing cells. Continously proliferating cells are typical for diseases like cancer and characterized by cells in all phases of the cell division cycle, namely in the G ("gap") 1, S ("DNA synthesis"), G2 and M ("mitosis") phase.

Compounds according to aspect a of the present invention more worthy to be mentioned include those compounds of formula I as defined at the outset, or, particularly, of formulae Ia, Ib, Ic, Id or Id' as shown below wherein Ra is —C(O)R1, in which R1 is 1-4C-alkyl, or 1-C-alkyl substituted by one or two substituents independently selected from R2, Rb is -T-Q, in which T is 1-6C-alkylene or 3-7C-cycloalkylene, and either Q is optionally substituted by Rba and/or Rbb and/or Rbc, and is phenyl, or Q is optionally substituted by Rca and/or Rcb, and is Har, or Q is attached via a carbon atom of the benzene ring to the parent molecular group, and is 1,3-benzodioxolyl, 2,2-difluoro-1,3-benzodioxolyl, 2,3-dihydro-1,4-benzodioxinyl, 2,3-dihydrobenzofuranyl, chromenyl or chromanyl, or Q is attached via a carbon atom of the benzene ring to the parent molecular group, and is benzofuranyl, or Q is tetrahyrofuranyl, or Q is 3-7C-cycloalkyl, wherein each R2 may be the same or different and is independently selected from the group consisting of:

Har, Het,

—C(O)R3, —C(O)OR4, —C(O)N(R5)R6,

—N(R7)C(O)R3, —OC(O)R3,

—OR4, hydroxy-2-4C-alkoxy, 1-4C-alkoxy-2-4C-alkoxy, pyridyl-1-4C-alkoxy, (1-4C-alkoxy-2-4C-alkoxy)-2-4C-alkoxy, and phenyl-1-4C-alkoxy, wherein each of said Har and Het is optionally substituted by one or two substituents independently selected from R10, in which each R3, R4, R5 and R6 may be the same or different and is each independently selected from the group consisting of: hydrogen, and 1-4C-alkyl, each R7 may be the same or different and is independently selected from the group consisting of: hydrogen, and 1-4C-alkyl, each R10 may be the same or different is independently selected from the group consisting of:

1-4C-alkyl, halogen, trifluoromethyl, cyano, 1-4C-alkoxycarbonyl, carboxyl, and hydroxyl, each Rba, Rbb, Rbc, Rca and Rcb may be the same or different and is each independently selected from the group consisting of:

1-4C-alkyl, halogen, trifluoromethyl, cyano, 1-4C-alkoxycarbonyl, carboxyl, and hydroxyl, each Har is the same or different and is independently either a 5-membered monocyclic heteroaryl radical comprising one to four heteroatoms independently selected from nitrogen, oxygen and sulphur, such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl, whereby said Har radical is attached to the parent molecular group via a ring carbon or ring nitrogen atom, or a 6-membered monocyclic heteroaryl radical comprising one or two nitrogen atoms, such as e.g. any one selected from pyridinyl, pyrazinyl, pyridazinyl and pyrimidinyl, whereby said Har radical is attached to the parent molecular group via a ring carbon atom, Het is a 3- to 7-membered monocyclic fully saturated heterocyclic ring comprising one or two heteroatoms independently selected from nitrogen, oxygen and sulphur, such as e.g. any one selected from aziridinyl, azetidinyl, pyrrolidinyl, piperidinyl, homopiperidinyl, pyrazolidinyl, imidazolidinyl, piperazinyl, homopiperazinyl, morpholinyl and thiomorpholinyl, whereby said Het radical is attached to the parent molecular group via a ring carbon or ring nitrogen atom;

under the proviso, that (6-acetyl-3-cyano-4,5,6,7-tetrahydro-thieno[2,3-c]pyridin-2-yl)-3-phenyl-propionamide is thereof disclaimed;

and the salts thereof.

In another embodiment, compounds according to aspect a of the present invention more worthy to be mentioned include those compounds of formula I as defined at the outset, or, particularly, of formulae Ia, Ib, Ic or Id as shown below, wherein Ra is —C(O)R1, in which R1 is 1-4C-alkyl, or 1-C-alkyl substituted by one or two substituents independently selected from R2, Rb is -T-Q, in which T is 1-6C-alkylene or 3-7C-cycloalkylene, and either Q is optionally substituted by Rba and/or Rbb and/or Rbc, and is phenyl, or Q is optionally substituted by Rca and/or Rcb, and is Har, or Q is attached via a carbon atom of the benzene ring to the parent molecular group, and is 1,3-benzodioxolyl, 2,2-difluoro-1,3-benzodioxolyl, 2,3-dihydro-1,4-benzodioxinyl, 2,3-dihydrobenzofuranyl, chromenyl or chromanyl, or Q is tetrahyrofuranyl, or Q is 3-7C-cycloalkyl, wherein each R2 may be the same or different and is independently selected from the group consisting of:

Har, Het,

—C(O)R3, —C(O)OR4, —C(O)N(R5)R6,

—N(R7)C(O)R3, —OC(O)R3,

—OR4, hydroxy-2-4C-alkoxy, 1-4C-alkoxy-2-4C-alkoxy, pyridyl-1-4C-alkoxy, (1-4C-alkoxy-2-4C-alkoxy)-2-4C-alkoxy, and phenyl-1-4C-alkoxy, wherein said Har is optionally substituted by one or two substituents independently selected from R10, in which each R3, R4, R5 and R6 may be the same or different and is each independently selected from the group consisting of: hydrogen, and 1-4C-alkyl, each R7 may be the same or different and is independently selected from the group consisting of: hydrogen, and 1-4C-alkyl, each R10 may be the same or different is independently selected from the group consisting of:

1-4C-alkyl, halogen, trifluoromethyl, cyano, 1-4C-alkoxycarbonyl, carboxyl, and hydroxyl, each Rba, Rbb, Rbc, Rca and Rcb may be the same or different and is each independently selected from the group consisting of:
  1-4C-alkyl, halogen, trifluoromethyl, cyano, 1-4C-alkoxycarbonyl, carboxyl, and hydroxyl,
each Har is the same or different and is independently either
  a 5-membered monocyclic heteroaryl radical comprising one to four heteroatoms independently selected from nitrogen, oxygen and sulphur,
    such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl,
  whereby said Har radical is attached to the parent molecular group via a ring carbon or ring nitrogen atom,
or
  a 6-membered monocyclic heteroaryl radical comprising one or two nitrogen atoms, such as e.g. any one selected from pyridinyl, pyrazinyl, pyridazinyl and pyrimidinyl,
  whereby said Har radical is attached to the parent molecular group via a ring carbon atom,
Het is a 3- to 7-membered monocyclic fully saturated heterocyclic ring comprising one or two heteroatoms independently selected from nitrogen, oxygen and sulphur,
  such as e.g. any one selected from aziridinyl, azetidinyl, pyrrolidinyl, piperidinyl,
homopiperidinyl,
  pyrazolidinyl, imidazolidinyl, piperazinyl, homopiperazinyl, morpholinyl and thiomorpholinyl,
  whereby said Het radical is attached to the parent molecular group via a ring carbon or ring nitrogen atom;
under the proviso, that
(6-acetyl-3-cyano-4,5,6,7-tetrahydro-thieno[2,3-c]pyridin-2-yl)-3-phenyl-propionamide
is thereof disclaimed;
and the salts thereof.

Compounds according to aspect a of the present invention in particular worthy to be mentioned include those compounds of formulae Ia, Ib, Ic, Id or Id' as shown below wherein
Ra is —C(O)R1, in which
R1 is 1-4C-alkyl, 1-4C-alkyl substituted by one substituent selected from R2, or 3-4C-alkyl substituted by two hydroxyl radicals on different carbon atoms, and
either
Q is optionally substituted by Rba and/or Rbb, and is phenyl,
or
Q is optionally substituted by Rca and/or Rcb, and is pyridinyl, furanyl, thiophenyl, pyrrolyl, pyrazolyl, thiazolyl, oxazolyl or imidazolyl,
or
Q is attached via a carbon atom of the benzene ring to the parent molecular group, and is 1,3-benzodioxolyl, 2,2-difluoro-1,3-benzodioxolyl, 2,3-dihydro-1,4-benzodioxinyl, 2,3-dihydrobenzofuranyl, chromenyl or chromanyl,
or
Q is attached via a carbon atom of the benzene ring to the parent molecular group, and is benzofuranyl,
or
Q is tetrahyrofuranyl,
or
Q is 3-7C-cycloalkyl, wherein
each R2 may be the same or different and is independently selected from the group consisting of:
  Har, morpholino, 4-methyl-piperazin-1-yl,
  —C(O)R3, —C(O)OR4, —C(O)N(R5)R6, —N(R7)C(O)R3, —OC(O)R3,
  —OR4, hydroxy-2-4C-alkoxy, 1-4C-alkoxy-2-4C-alkoxy, pyridyl-1-4C-alkoxy, phenyl-1-4C-alkoxy, and (1-4C-alkoxy-2-4C-alkoxy)-2-4C-alkoxy,
  wherein said Har may be optionally substituted by one or two substituents independently selected from R10,
in which
each R3, R4, R5 and R6 may be the same or different and is each independently selected from the group consisting of:
  hydrogen, and 1-4C-alkyl,
R7 is hydrogen,
either
Har is bonded to the parent molecular group via a ring carbon atom or a ring nitrogen atom, and is imidazolyl, pyrazolyl or triazolyl,
or
Har is bonded to the parent molecular group via a ring carbon atom, and is pyridinyl, pyrazinyl or pyrimidinyl,
R10 is 1-4C-alkyl,
each Rba and Rbb may be the same or different and is each independently selected from the group consisting of:
  1-4C-alkyl, fluorine, chlorine, bromine, trifluoromethyl, cyano, and hydroxyl,
each Rca and Rcb may be the same or different and is each independently selected from the group consisting of:
  1-4C-alkyl, fluorine, chlorine, trifluoromethyl, and cyano;
under the proviso, that
(6-acetyl-3-cyano-4,5,6,7-tetrahydro-thieno[2,3-c]pyridin-2-yl)-3-phenyl-propionamide
is thereof disclaimed;
and the salts thereof.

In another embodiment, compounds according to aspect a of the present invention in particular worthy to be mentioned include those compounds of formulae Ia, Ib, Ic or Id as shown below wherein
Ra is —C(O)R1, in which
R1 is 1-4C-alkyl, 1-4C-alkyl substituted by one substituent selected from R2, or 3-4C-alkyl substituted by two hydroxyl radicals on different carbon atoms, and
either
Q is optionally substituted by Rba and/or Rbb, and is phenyl,
or
Q is optionally substituted by Rca and/or Rcb, and is pyridinyl, furanyl, thiophenyl, pyrrolyl, pyrazolyl, thiazolyl, oxazolyl or imidazolyl,
or
Q is attached via a carbon atom of the benzene ring to the parent molecular group, and is 1,3-benzodioxolyl, 2,2-difluoro-1,3-benzodioxolyl, 2,3-dihydro-1,4-benzodioxinyl, 2,3-dihydrobenzofuranyl, chromenyl or chromanyl,
or
Q is tetrahyrofuranyl,
or
Q is 3-7C-cycloalkyl, wherein
each R2 may be the same or different and is independently selected from the group consisting of:
  pyridinyl, pyrimidinyl, pyrazinyl, triazol-1-yl, imidazol-1-yl, pyrazol-1-yl, morpholino, 1N-(1-4C-alkyl)-imidazolyl, 1N-(1-4C-alkyl)-pyrazolyl, —C(O)R3, —C(O)OR4, —C(O)N(R5)R6,
—N(R7)C(O)R3, —OC(O)R3,
—OR4, hydroxy-2-4C-alkoxy, 1-4C-alkoxy-2-4C-alkoxy, pyridyl-1-4C-alkoxy, and (1-4C-alkoxy-2-4C-alkoxy)-2-4C-alkoxy,
in which
each R3, R4, R5 and R6 may be the same or different and is each independently selected from the group consisting of: hydrogen, and 1-4C-alkyl,
R7 is hydrogen,
each Rba and Rbb may be the same or different and is each independently selected from the group consisting of:
    1-4C-alkyl, fluorine, chlorine, bromine, trifluoromethyl, cyano, and hydroxyl,
each Rca and Rcb may be the same or different and is each independently selected from the group consisting of:
    1-4C-alkyl, fluorine, chlorine, trifluoromethyl, and cyano;
under the proviso, that
(6-acetyl-3-cyano-4,5,6,7-tetrahydro-thieno[2,3-c]pyridin-2-yl)-3-phenyl-propionamide
is thereof disclaimed;
and the salts thereof.

In one embodiment of aspect a (embodiment a1), compounds according to aspect a of the present invention in more particular worthy to be mentioned include those compounds of formula Ia, Ib or Ic as shown below
wherein
Ra is —C(O)R1, in which
R1 is 1-4C-alkyl, such as e.g. methyl, ethyl or propyl,
    or
    1-4C-alkyl, such as e.g. methyl, ethyl or propyl, which is substituted by one substituent selected from R2,
    or
    1-2C-alkyl, such as e.g. methyl or ethyl, which is substituted by 2,2-dimethyl-[1,3]dioxolan-4-yl,
    or
    3-4C-alkyl, such as e.g. propyl or butyl, which is substituted by two hydroxyl radicals on different carbon atoms, and
either
Q is optionally substituted by Rba and/or Rbb, and is phenyl,
or
Q is optionally substituted by Rca and/or Rcb, and is pyridinyl, furanyl, thiophenyl or pyrazol-1-yl,
or
Q is 1,3-benzodioxol-5-yl, 2,3-dihydro-1,4-benzodioxin-6-yl, 2,2-difluoro-1,3-benzodioxol-5-yl, chromen-6-yl, chromen-7-yl, chroman-6-yl, chroman-7-yl, 2,3-dihydrobenzofuran-5-yl, or 2,3-dihydrobenzofuran-6-yl,
or
Q is benzofuran-5-yl, or benzofuran-6-yl,
or
Q is tetrahydrofuranyl,
or
Q is 5-6C-cycloalkyl,
wherein
each R2 may be the same or different and is independently selected from the group consisting of:
    pyridyl, pyrimidinyl, R201- and/or R202-substituted pyridyl, R201- and/or R202-substituted pyrimidinyl, morpholino, imidazol-1-yl, pyrazol-1-yl, mono- or di-(R201)-substituted imidazol-1-yl, mono- or di-(R201)-substituted pyrazol-1-yl, 1N-(1-4C-alkyl)-imidazolyl, 1N-(1-4C-alkyl)-pyrazol-1-yl, R201-substituted 1N-(1-4C-alkyl)-imidazolyl, R201-substituted 1N-(1-4C-alkyl)-pyrazol-1-yl, 1N—(H)-imidazolyl, 1N—(H)-pyrazol-1-yl, R201-substituted 1N—(H)-imidazolyl, R201-substituted 1N—(H)-pyrazol-1-yl, —C(O)OR4, —OC(O)R3,
    —OR4,
    phenyl-1-2C-alkoxy such as e.g. benzyloxy,
    1-2C-alkoxy-2-3C-alkoxy such as e.g. 2-methoxyethoxy, and
    (1-2C-alkoxy-2-3C-alkoxy)-2-3C-alkoxy such as e.g. 2-(2-methoxyethoxy)-ethoxy,
    in which
R3 is 1-4C-alkyl such as e.g. methyl,
each R4 may be the same or different and is independently selected from the group consisting of:
    hydrogen, and 1-4C-alkyl such as e.g. methyl or ethyl,
R201 is 1-4C-alkyl such as e.g. methyl or ethyl,
R202 is 1-4C-alkyl such as e.g. methyl or ethyl,
each Rba and Rbb may be the same or different and is each independently selected from the group consisting of:
    methyl, ethyl, fluorine, chlorine, bromine, and trifluoromethyl,
each Rca and Rcb may be the same or different and is each independently selected from the group consisting of:
    methyl, ethyl, fluorine, chlorine, and trifluoromethyl;
in a particular subembodiment
Q is unsubstituted, and is pyridinyl, e.g. pyridin-2-yl, pyridin-3-yl or pyridin-4-yl, especially pyridin-2-yl or pyridin-3-yl,
in another particular subembodiment
Q is unsubstituted, and is furanyl, e.g. furan-2-yl or furan-3-yl, especially furan-2-yl,
in another particular subembodiment
Q is unsubstituted, and is thiophenyl, e.g. thiophen-2-yl or thiophen-3-yl, especially thiophen-2-yl,
in another particular subembodiment
Q is 2-(Rba)-phenyl, in which
Rba is methyl, ethyl, chlorine or fluorine,
in another particular subembodiment
Q is 3-(Rba)-phenyl, in which
Rba is methyl, ethyl, chlorine or fluorine,
in another particular subembodiment
Q is 2-(Rca)-furan-3-yl, 5-(Rca)-furan-3-yl, or, especially, 5-(Rca)-furan-2-yl, in which
Rca is methyl or chlorine,
in another particular subembodiment
Q is 5-(Rca)-3-(Rcb)-furan-2-yl, 2-(Rca)-4-(Rcb)-furan-3-yl, 2-(Rca)-5-(Rcb)-furan-3-yl, 2-(Rcb)-5-(Rca)-furan-3-yl, 5-(Rca)-4-(Rcb)-furan-3-yl, or, especially, 5-(Rca)-4-(Rcb)-furan-2-yl, in which
Rca is methyl or chlorine,
Rcb is methyl,
in another particular subembodiment
Q is 2-(Rca)-thiophen-3-yl, 5-(Rca)-thiophen-3-yl, or, especially, 5-(Rca)-thiophen-2-yl, in which
Rca is methyl or chlorine,
in another particular subembodiment
Q is 5-(Rca)-3-(Rcb)-thiophen-2-yl, 2-(Rca)-4-(Rcb)-thiophen-3-yl, 2-(Rca)-5-(Rcb)-thiophen-3-yl, 2-(Rcb)-5-(Rca)-thiophen-3-yl, 5-(Rca)-4-(Rcb)-thiophen-3-yl, or, especially, 5-(Rca)-4-(Rcb)-thiophen-2-yl, in which
Rca is methyl or chlorine,
Rcb is methyl;
in a more particular subembodiment
Q is unsubstituted, and is pyridin-2-yl or pyridin-3-yl,
in another more particular subembodiment
Q is unsubstituted, and is furan-2-yl,
in another more particular subembodiment Q is unsubstituted, and is thiophen-2-yl,
in another more particular subembodiment
Q is 2-(Rba)-phenyl, in which
Rba is methyl, chlorine or fluorine,
in another more particular subembodiment
Q is 3-(Rba)-phenyl, in which
Rba is methyl, chlorine or fluorine;
under theproviso, that
(6-acetyl-3-cyano-4,5,6,7-tetrahydro-thieno[2,3-c]pyridin-2-yl)-3-phenyl-propionamide
is thereof disclaimed;
and the salts thereof.

In another embodiment of aspect a (embodiment a2), compounds according to aspect a of the present invention in more particular worthy to be mentioned include those compounds of formula Ia as shown below wherein
Ra is —C(O)R1, in which
R1 is 1-4C-alkyl, such as e.g. methyl, ethyl or propyl,
or
1-4C-alkyl, such as e.g. methyl, ethyl or propyl, which is substituted by one substituent selected from R2,
or
3-4C-alkyl, such as e.g. propyl or butyl, which is substituted by two hydroxyl radicals on different carbon atoms, and
either
Q is optionally substituted by Rba and/or Rbb, and is phenyl,
or
Q is optionally substituted by Rca and/or Rcb, and is pyridinyl, furanyl, thiophenyl or pyrazol-1-yl,
or
Q is 1,3-benzodioxol-5-yl, 2,3-dihydro-1,4-benzodioxin-6-yl, 2,2-difluoro-1,3-benzodioxol-5-yl, chromen-6-yl, chromen-7-yl, chroman-yl, chroman-7-yl, 2,3-dihydrobenzofuran-5-yl, or 2,3-dihydrobenzofuran-6-yl,
or
Q is tetrahydrofuranyl,
or
Q is 5-6C-cycloalkyl,
wherein
each R2 may be the same or different and is independently selected from the group consisting of:
pyridinyl, morpholino, imidazol-1-yl, pyrazol-1-yl,
—C(O)OR4, —OC(O)R3,
—OR4,
1-2C-alkoxy-2-3C-alkoxy such as e.g. 2-methoxyethoxy, and
(1-2C-alkoxy-2-3C-alkoxy)-2-3C-alkoxy such as e.g. 2-(2-methoxyethoxy)-ethoxy,
in which
R3 is 1-4C-alkyl such as e.g. methyl,
each R4 may be the same or different and is independently selected from the group consisting of:
hydrogen, and 1-4C-alkyl such as e.g. methyl or ethyl,
each Rba and Rbb may be the same or different and is each independently selected from the group consisting of:
methyl, ethyl, fluorine, chlorine, bromine, and trifluoromethyl,
Rca is methyl,
Rcb is methyl;
in a particular subembodiment
Q is unsubstituted, and is pyridinyl, e.g. pyridin-2-yl, pyridin-3-yl or pyridin-4-yl, especially pyridin-2-yl or pyridin-3-yl,
in another particular subembodiment
Q is unsubstituted, and is furanyl, e.g. furan-2-yl or furan-3-yl, especially furan-2-yl,
in another particular subembodiment
Q is unsubstituted, and is thiophenyl, e.g. thiophen-2-yl or thiophen-3-yl, especially thiophen-2-yl,
in another particular subembodiment
Q is 2-(Rba)-phenyl, in which
Rba is methyl, ethyl, chlorine or fluorine,
in another particular subembodiment
Q is 3-(Rba)-phenyl, in which
Rba is methyl, ethyl, chlorine or fluorine,
in another particular subembodiment
Q is 2-(Rca)-furan-3-yl, 5-(Rca)-furan-3-yl, or, especially, 5-(Rca)-furan-2-yl, in which
Rca is methyl,
in another particular subembodiment
Q is 5-(Rca)-3-(Rcb)-furan-2-yl, 2-(Rca)-4-(Rcb)-furan-3-yl, 2-(Rca)-5-(Rcb)-furan-3-yl, 2-(Rcb)-5-(Rca)-furan-3-yl, 5-(Rca)-4-(Rcb)-furan-3-yl, or, especially, 5-(Rca)-4-(Rcb)-furan-2-yl, in which
Rca is methyl,
Rcb is methyl,
in another particular subembodiment
Q is 2-(Rca)-thiophen-3-yl, 5-(Rca)-thiophen-3-yl, or, especially, 5-(Rca)-thiophen-2-yl, in which
Rca is methyl,
in another particular subembodiment
Q is 5-(Rca)-3-(Rcb)-thiophen-2-yl, 2-(Rca)-4-(Rcb)-thiophen-3-yl, 2-(Rca)-5-(Rcb)-thiophen-3-yl, 2-(Rcb)-5-(Rca)-thiophen-3-yl, 5-(Rca)-4-(Rcb)-thiophen-3-yl, or, especially, 5-(Rca)-4-(Rcb)-thiophen-2-yl, in which
Rca is methyl,
Rcb is methyl;
in a more particular subembodiment
Q is unsubstituted, and is pyridin-2-yl or pyridin-3-yl,
in another more particular subembodiment
Q is unsubstituted, and is furan-2-yl,
in another more particular subembodiment
Q is unsubstituted, and is thiophen-2-yl,
in another more particular subembodiment
Q is 2-(Rba)-phenyl, in which
Rba is methyl, chlorine or fluorine,
in another more particular subembodiment
Q is 3-(Rba)-phenyl, in which
Rba is methyl, chlorine or fluorine;
under theproviso, that
(6-acetyl-3-cyano-4,5,6,7-tetrahydro-thieno[2,3-c]pyridin-2-yl)-3-phenyl-propionamide
is thereof disclaimed;
and the salts thereof.

In a more detailed embodiment of aspect a (aspect a1'i), compounds according to aspect a of the present invention in further more particular worthy to be mentioned include those compounds of formula Ia, Ib or Ic as shown below wherein
Ra is —C(O)R1, in which
either
R1 is methyl, ethyl or propyl,
or
R1 is (R2)-methyl, 2-(R2)-ethyl, or 3-(R2)-propyl,
or
R1 is 2,3-dihydroxypropyl, and
either
Q is unsubstituted, and is phenyl,
or
Q is unsubstituted, and is pyridinyl, furanyl or thiophenyl, or Q is substituted by Rba and/or Rbb, and is phenyl, or Q is substituted by Rca and/or Rcb, and is pyridinyl, furanyl or thiophenyl, wherein each R2 may be the same or different and is independently selected from the group consisting of:
pyridyl, pyrimidinyl, methyl-substituted pyridyl, imidazol-1-yl, mono- or di-methyl-substituted imidazol-1-yl, carboxyl, methoxycarbonyl, hydroxyl, methylcarbonyloxy, methoxy, ethoxy, benzyloxy, and 2-methoxyethoxy, each Rba and Rbb may be the same or different and is each independently selected from the group consisting of:
methyl, ethyl, fluorine and chlorine, each Rca and Rcb may be the same or different and is each independently selected from the group consisting of:
methyl, ethyl and chlorine;

in a particular subembodiment

Q is unsubstituted, and is pyridinyl, e.g. pyridin-2-yl, pyridin-3-yl or pyridin-4-yl, especially pyridin-2-yl or pyridin-3-yl, in another particular subembodiment Q is unsubstituted, and is furanyl, e.g. furan-2-yl or furan-3-yl, especially furan-2-yl, in another particular subembodiment Q is unsubstituted, and is thiophenyl, e.g. thiophen-2-yl or thiophen-3-yl, especially thiophen-2-yl, in another particular subembodiment Q is 2-(Rba)-phenyl, in which Rba is methyl, ethyl, chlorine or fluorine, in another particular subembodiment Q is 3-(Rba)-phenyl, in which Rba is methyl, ethyl, chlorine or fluorine, in another particular subembodiment Q is 5-(Rca)-furan-3-yl, or, especially, 5-(Rca)-furan-2-yl, in which Rca is methyl or chlorine, in another particular subembodiment Q is 5-(Rca)-4-(Rcb)-furan-3-yl, or, especially, 5-(Rca)-4-(Rcb)-furan-2-yl, in which Rca is methyl or chlorine, Rcb is methyl, in another particular subembodiment Q is 5-(Rca)-thiophen-3-yl, or, especially, 5-(Rca)-thiophen-2-yl, in which Rca is methyl or chlorine;

in a more particular subembodiment

Q is unsubstituted, and is pyridin-2-yl or pyridin-3-yl, in another more particular subembodiment Q is unsubstituted, and is furan-2-yl, in another more particular subembodiment Q is unsubstituted, and is thiophen-2-yl, in another more particular subembodiment Q is 2-(Rba)-phenyl, in which Rba is methyl, chlorine or fluorine, in another more particular subembodiment Q is 3-(Rba)-phenyl, in which Rba is methyl, chlorine or fluorine;

in a further more particular subembodiment

Q is unsubstituted, and is pyridin-2-yl, in another further more particular subembodiment Q is unsubstituted, and is pyridin-3-yl, in another further more particular subembodiment Q is unsubstituted, and is furan-2-yl, in another further more particular subembodiment Q is unsubstituted, and is thiophen-2-yl;

under theproviso, that (6-acetyl-3-cyano-4,5,6,7-tetrahydro-thieno[2,3-c]pyridin-2-yl)-3-phenyl-propionamide is thereof disclaimed;

and the salts thereof.

Yet in a more detailed embodiment of aspect a (aspect a1'ii), compounds according to aspect a of the present invention in further more particular worthy to be mentioned include those compounds of formula Ia, Ib or Ic as shown below wherein Ra is —C(O)R1, in which either R1 is methyl, ethyl or propyl, or R1 is (R2)-methyl, 2-(R2)-ethyl, or 3-(R2)-propyl, or R1 is 2,3-dihydroxypropyl, and either Q is unsubstituted, and is phenyl, or Q is unsubstituted, and is pyridinyl, furanyl or thiophenyl, or Q is substituted by Rba and/or Rbb, and is phenyl, or Q is substituted by Rca and/or Rcb, and is pyridinyl, furanyl or thiophenyl, or Q is cyclohexyl or cyclopentyl, wherein each R2 may be the same or different and is independently selected from the group consisting of:
pyridyl, pyrimidinyl, methyl-substituted pyridyl, imidazol-1-yl, mono- or di-methyl-substituted imidazol-1-yl, 1N-methyl-imidazolyl, carboxyl, methoxycarbonyl, hydroxyl, methylcarbonyloxy, methoxy, ethoxy, benzyloxy, and 2-methoxyethoxy, each Rba and Rbb may be the same or different and is each independently selected from the group consisting of:
methyl, ethyl, fluorine and chlorine, each Rca and Rcb may be the same or different and is each independently selected from the group consisting of:
methyl, ethyl and chlorine;

in a particular subembodiment

Q is unsubstituted, and is phenyl, in another particular subembodiment

Q is unsubstituted, and is pyridinyl, e.g. pyridin-2-yl, pyridin-3-yl or pyridin-4-yl, especially pyridin-2-yl or pyridin-3-yl, in another particular subembodiment Q is unsubstituted, and is furanyl, e.g. furan-2-yl or furan-3-yl, especially furan-2-yl, in another particular subembodiment Q is unsubstituted, and is thiophenyl, e.g. thiophen-2-yl or thiophen-3-yl, especially thiophen-2-yl, in another particular subembodiment Q is 2-(Rba)-phenyl, in which Rba is methyl, ethyl, chlorine or fluorine, in another particular subembodiment Q is 3-(Rba)-phenyl, in which Rba is methyl, ethyl, chlorine or fluorine, in another particular subembodiment Q is 5-(Rca)-furan-3-yl, or, especially, 5-(Rca)-furan-2-yl, in which Rca is methyl or chlorine, in another particular subembodiment
Q is 5-(Rca)-4-(Rcb)-furan-3-yl, or, especially, 5-(Rca)-4-(Rcb)-furan-2-yl, in which
Rca is methyl or chlorine,
Rcb is methyl,
in another particular subembodiment
Q is 5-(Rca)-thiophen-3-yl, or, especially, 5-(Rca)-thiophen-2-yl, in which
Rca is methyl or chlorine,
in another particular subembodiment
Q is cyclohexyl or cyclopentyl;
in a more particular subembodiment
Q is unsubstituted, and is phenyl,
in another more particular subembodiment
Q is unsubstituted, and is pyridin-2-yl or pyridin-3-yl,
in another more particular subembodiment
Q is unsubstituted, and is furan-2-yl,
in another more particular subembodiment
Q is unsubstituted, and is thiophen-2-yl,
in another more particular subembodiment
Q is 2-(Rba)-phenyl, in which
Rba is methyl, chlorine or fluorine,
in another more particular subembodiment
Q is 3-(Rba)-phenyl, in which
Rba is methyl, chlorine or fluorine,
in another more particular subembodiment
Q is cyclohexyl or cyclopentyl;
in a further more particular subembodiment
Q is unsubstituted, and is phenyl,
in another further more particular subembodiment
Q is unsubstituted, and is pyridin-2-yl,
in another further more particular subembodiment
Q is unsubstituted, and is pyridin-3-yl,
in another further more particular subembodiment
Q is unsubstituted, and is furan-2-yl,
in another further more particular subembodiment
Q is unsubstituted, and is thiophen-2-yl,
in another further more particular subembodiment
Q is cyclohexyl;
under theproviso, that
(6-acetyl-3-cyano-4,5,6,7-tetrahydro-thieno[2,3-c]pyridin-2-yl)-3-phenyl-propionamide
is thereof disclaimed;
and the salts thereof.

In another more detailed embodiment of aspect a (aspect a2'), compounds according to aspect a of the present invention in further more particular worthy to be mentioned include those compounds of formula Ia as shown below wherein
Ra is —C(O)R1, in which
either
R1 is methyl, ethyl or propyl,
or
R1 is (R2)-methyl, 2-(R2)-ethyl, or 3-(R2)-propyl,
or
R1 is 2,3-dihydroxypropyl, and
either
Q is unsubstituted, and is phenyl,
or
Q is unsubstituted, and is pyridinyl, furanyl or thiophenyl,
or
Q is substituted by Rba and/or Rbb, and is phenyl,
wherein
each R2 may be the same or different and is independently selected from the group consisting of:
pyridinyl, methoxycarbonyl, methylcarbonyloxy, methoxy, ethoxy, and 2-methoxyethoxy,
each Rba and Rbb may be the same or different and is each independently selected from the group consisting of:
methyl, ethyl, fluorine, bromine, and chlorine;
in a particular subembodiment
Q is unsubstituted, and is pyridinyl, e.g. pyridin-2-yl, pyridin-3-yl or pyridin-4-yl, especially pyridin-2-yl or pyridin-3-yl,
in another particular subembodiment
Q is unsubstituted, and is furanyl, e.g. furan-2-yl or furan-3-yl, especially furan-2-yl,
in another particular subembodiment
Q is unsubstituted, and is thiophenyl, e.g. thiophen-2-yl or thiophen-3-yl, especially thiophen-2-yl,
in another particular subembodiment
Q is 2-(Rba)-phenyl, in which
Rba is methyl, ethyl, chlorine or fluorine,
in another particular subembodiment
Q is 3-(Rba)-phenyl, in which
Rba is methyl, ethyl, chlorine or fluorine;
in a more particular subembodiment
Q is unsubstituted, and is pyridin-2-yl or pyridin-3-yl,
in another more particular subembodiment
Q is unsubstituted, and is furan-2-yl,
in another more particular subembodiment
Q is unsubstituted, and is thiophen-2-yl,
in another more particular subembodiment
Q is 2-(Rba)-phenyl, in which
Rba is methyl, chlorine or fluorine,
in another more particular subembodiment
Q is 3-(Rba)-phenyl, in which
Rba is methyl, chlorine or fluorine;
in a further more particular subembodiment
Q is unsubstituted, and is pyridin-2-yl,
in another further more particular subembodiment
Q is unsubstituted, and is pyridin-3-yl,
in another further more particular subembodiment
Q is unsubstituted, and is furan-2-yl,
in another further more particular subembodiment
Q is unsubstituted, and is thiophen-2-yl;
under theproviso, that
(6-acetyl-3-cyano-4,5,6,7-tetrahydro-thieno[2,3-c]pyridin-2-yl)-3-phenyl-propionamide
is thereof disclaimed;
and the salts thereof.

Compounds according to aspect a of the present invention to be emphasized include those compounds of formula Ia or Ic as shown below wherein
Ra is —C(O)R1, in which
either
R1 is (R2)-methyl, or 2-(R2)-ethyl, in which
R2 is pyridyl,
or
R1 is (R2)-methyl, or 2-(R2)-ethyl, in which
R2 is methoxy,
or
R1 is (2-methoxyethoxy)-methyl,
or
R1 is (R2)-methyl, or 2-(R2)-ethyl, in which
R2 is imidazol-1-yl;

and wherein
either
Q is unsubstituted, and is pyridinyl, e.g. pyridin-2-yl, pyridin-3-yl or pyridin-4-yl, especially pyridin-2-yl or pyridin-3-yl,
or
Q is unsubstituted, and is furanyl, e.g. furan-2-yl or furan-3-yl, especially furan-2-yl,
or
Q is unsubstituted, and is thiophenyl, e.g. thiophen-2-yl or thiophen-3-yl, especially thiophen-2-yl,
or
Q is 2-(Rba)-phenyl, in which
Rba is methyl, ethyl, chlorine or fluorine,
or
Q is 3-(Rba)-phenyl, in which
Rba is methyl, ethyl, chlorine or fluorine,
or
Q is 5-(Rca)-furan-2-yl, in which
Rca is methyl or chlorine,
or
Q 5-(Rca)-4-(Rcb)-furan-2-yl, in which
Rca is methyl or chlorine,
Rcb is methyl,
or
Q is 5-(Rca)-thiophen-2-yl, in which
Rca is methyl or chlorine;
in a particular subembodiment
Q is unsubstituted, and is pyridin-2-yl,
in another particular subembodiment
Q is unsubstituted, and is pyridin-3-yl,
in another particular subembodiment
Q is unsubstituted, and is furan-2-yl,
in another particular subembodiment
Q is unsubstituted, and is thiophen-2-yl,
in another particular subembodiment
Q is 2-(Rba)-phenyl, in which
Rba is methyl, chlorine or fluorine,
in another particular subembodiment
Q is 3-(Rba)-phenyl, in which
Rba is methyl, chlorine or fluorine;
in a more particular subembodiment
Q is unsubstituted, and is pyridin-2-yl,
in another more particular subembodiment
Q is unsubstituted, and is pyridin-3-yl,
in another more particular subembodiment
Q is unsubstituted, and is furan-2-yl,
in another more particular subembodiment
Q is unsubstituted, and is thiophen-2-yl;
and the salts thereof.

Yet compounds according to aspect a of the present invention to be emphasized include those compounds of formula Ia, Ib or Ic as shown below
wherein
Ra is —C(O)R1, in which
either
R1 is (R2)-methyl, or 2-(R2)-ethyl, in which
R2 is pyridyl,
or
R1 is (R2)-methyl, in which
R2 is 1N-methyl-imidazolyl,
or
R1 is (R2)-methyl, or 2-(R2)-ethyl, in which
R2 is hydroxyl or methoxy,
or
R1 is (2-methoxyethoxy)-methyl,
or
R1 is (R2)-methyl, or 2-(R2)-ethyl, in which
R2 is imidazol-1-yl, or mono- or di-methyl-substituted imidazol-1-yl;
and wherein
either
Q is unsubstituted, and is phenyl,
or
Q is unsubstituted, and is pyridinyl, e.g. pyridin-2-yl, pyridin-3-yl or pyridin-4-yl, especially pyridin-2-yl or pyridin-3-yl,
or
Q is unsubstituted, and is furanyl, e.g. furan-2-yl or furan-3-yl, especially furan-2-yl,
or
Q is unsubstituted, and is thiophenyl, e.g. thiophen-2-yl or thiophen-3-yl, especially thiophen-2-yl,
or
Q is 2-(Rba)-phenyl, in which
Rba is methyl, ethyl, chlorine or fluorine,
or
Q is 3-(Rba)-phenyl, in which
Rba is methyl, ethyl, chlorine or fluorine,
or
Q is 5-(Rca)-furan-2-yl, in which
Rca is methyl or chlorine,
or
Q 5-(Rca)-4-(Rcb)-furan-2-yl, in which
Rca is methyl or chlorine,
Rcb is methyl,
or
Q is 5-(Rca)-thiophen-2-yl, in which
Rca is methyl or chlorine,
or
Q is cyclohexyl or cyclopentyl;
in a particular subembodiment
Q is unsubstituted, and is phenyl,
in another particular subembodiment
Q is unsubstituted, and is pyridin-2-yl,
in another particular subembodiment
Q is unsubstituted, and is pyridin-3-yl,
in another particular subembodiment
Q is unsubstituted, and is furan-2-yl,
in another particular subembodiment
Q is unsubstituted, and is thiophen-2-yl,
in another particular subembodiment
Q is 2-(Rba)-phenyl, in which
Rba is methyl, chlorine or fluorine,
in another particular subembodiment
Q is 3-(Rba)-phenyl, in which
Rba is methyl, chlorine or fluorine,
in another particular subembodiment
Q is cyclohexyl or cyclopentyl;
in a more particular subembodiment
Q is unsubstituted, and is phenyl,
in another more particular subembodiment
Q is unsubstituted, and is pyridin-2-yl,
in another more particular subembodiment
Q is unsubstituted, and is pyridin-3-yl,
in another more particular subembodiment
Q is unsubstituted, and is furan-2-yl,
in another more particular subembodiment
Q is unsubstituted, and is thiophen-2-yl,
in another more particular subembodiment
Q is cyclohexyl;
and the salts thereof.

Compounds according to aspect a of the present invention to be more emphasized include those compounds of formula Ia or Ic as shown below
wherein
Ra is —C(O)R1, in which
either
R1 is (R2)-methyl, or 2-(R2)-ethyl, in which
R2 is pyridyl,
or
R1 is 2-(R2)-ethyl, in which
R2 is imidazol-1-yl;

and wherein
either
Q is unsubstituted, and is pyridinyl, e.g. pyridin-2-yl, pyridin-3-yl or pyridin-4-yl, especially pyridin-2-yl or pyridin-3-yl,
or
Q is unsubstituted, and is furanyl, e.g. furan-2-yl or furan-3-yl, especially furan-2-yl,
or
Q is unsubstituted, and is thiophenyl, e.g. thiophen-2-yl or thiophen-3-yl, especially thiophen-2-yl,
or
Q is 2-(Rba)-phenyl, in which
Rba is methyl, ethyl, chlorine or fluorine,
or
Q is 3-(Rba)-phenyl, in which
Rba is methyl, ethyl, chlorine or fluorine,
or
Q is 5-(Rca)-furan-2-yl, in which
Rca is methyl or chlorine,
or
Q is 5-(Rca)-4-(Rcb)-furan-2-yl, in which
Rca is methyl or chlorine,
Rcb is methyl,
or
Q is 5-(Rca)-thiophen-2-yl, in which
Rca is methyl or chlorine;
in a particular subembodiment
Q is unsubstituted, and is pyridin-2-yl,
in another particular subembodiment
Q is unsubstituted, and is pyridin-3-yl,
in another particular subembodiment
Q is unsubstituted, and is furan-2-yl,
in another particular subembodiment
Q is unsubstituted, and is thiophen-2-yl,
in another particular subembodiment
Q is 2-(Rba)-phenyl, in which
Rba is methyl, chlorine or fluorine,
in another particular subembodiment
Q is 3-(Rba)-phenyl, in which
Rba is methyl, chlorine or fluorine;
in a more particular subembodiment
Q is unsubstituted, and is pyridin-2-yl,
in another more particular subembodiment
Q is unsubstituted, and is pyridin-3-yl,
in another more particular subembodiment
Q is unsubstituted, and is furan-2-yl;
and the salts thereof.

Yet compounds according to aspect a of the present invention to be more emphasized include those compounds of formula Ia, Ib or Ic as shown below
wherein
Ra is —C(O)R1, in which
either
R1 is (R2)-methyl, or 2-(R2)-ethyl, in which
R2 is pyridin-2-yl, pyridin-3-yl or pyridin-4-yl,
or
R1 is (R2)-methyl, in which
R2 is 1-methyl-imidazol-2-yl or 1-methyl-imidazol-5-yl,
or
R1 is (R2)-methyl, or 2-(R2)-ethyl, in which
R2 is hydroxyl,
or
R1 is (R2)-methyl, or 2-(R2)-ethyl, in which
R2 is imidazol-1-yl, 2-methyl-imidazol-1-yl, 4-methyl-imidazol-1-yl or 2,4-dimethyl-imidazol-1-yl;

and wherein
either
Q is unsubstituted, and is phenyl,
or
Q is unsubstituted, and is pyridinyl, e.g. pyridin-2-yl, pyridin-3-yl or pyridin-4-yl, especially pyridin-2-yl or pyridin-3-yl,
or
Q is unsubstituted, and is furanyl, e.g. furan-2-yl or furan-3-yl, especially furan-2-yl,
or
Q is unsubstituted, and is thiophenyl, e.g. thiophen-2-yl or thiophen-3-yl, especially thiophen-2-yl,
or
Q is 2-(Rba)-phenyl, in which
Rba is methyl, ethyl, chlorine or fluorine,
or
Q is 3-(Rba)-phenyl, in which
Rba is methyl, ethyl, chlorine or fluorine,
or
Q is 5-(Rca)-furan-2-yl, in which
Rca is methyl or chlorine,
or
Q is 5-(Rca)-4-(Rcb)-furan-2-yl, in which
Rca is methyl or chlorine,
Rcb is methyl,
or
Q is 5-(Rca)-thiophen-2-yl, in which
Rca is methyl or chlorine,
or
Q is cyclohexyl or cyclopentyl;
in a particular subembodiment
Q is unsubstituted, and is phenyl,
in another particular subembodiment
Q is unsubstituted, and is pyridin-2-yl,
in another particular subembodiment
Q is unsubstituted, and is pyridin-3-yl,
in another particular subembodiment
Q is unsubstituted, and is furan-2-yl,
in another particular subembodiment
Q is unsubstituted, and is thiophen-2-yl,
in another particular subembodiment
Q is 2-(Rba)-phenyl, in which
Rba is methyl, chlorine or fluorine,
in another particular subembodiment
Q is 3-(Rba)-phenyl, in which
Rba is methyl, chlorine or fluorine,
in another particular subembodiment
Q is cyclohexyl; in a more particular subembodiment
Q is unsubstituted, and is phenyl,
in another more particular subembodiment
Q is unsubstituted, and is pyridin-2-yl,
in another more particular subembodiment Q is unsubstituted, and is pyridin-3-yl,
in another more particular subembodiment
Q is unsubstituted, and is furan-2-yl,
in another more particular subembodiment
Q is cyclohexyl;
and the salts thereof.

Compounds according to aspect a of the present invention to be further more emphasized include those compounds of formula Ia, Ib or Ic as shown below wherein
Ra is —C(O)R1, in which
either
R1 is (R2)-methyl, or 2-(R2)-ethyl, in which
R2 is pyridin-2-yl, pyridin-3-yl or pyridin-4-yl,
or
R1 is (R2)-methyl, or 2-(R2)-ethyl, in which
R2 is hydroxyl,
or
R1 is (R2)-methyl, or 2-(R2)-ethyl, in which
R2 is imidazol-1-yl;

and wherein
either
Q is unsubstituted, and is phenyl,
or
Q is unsubstituted, and is pyridin-2-yl,
or
Q is unsubstituted, and is pyridin-3-yl,
or
Q is unsubstituted, and is furan-2-yl,
or
Q is cyclohexyl;

and the salts thereof.

Compounds according to aspect a of the present invention to be in particular emphasized include those compounds of formula Ia, Ib or Ic as shown below wherein
Ra is —C(O)R1, in which
either
R1 is (R2)-methyl, or 2-(R2)-ethyl, in which
R2 is pyridin-2-yl, pyridin-3-yl or pyridin-4-yl,
or
R1 is (R2)-methyl, or 2-(R2)-ethyl, in which
R2 is imidazol-1-yl;

and wherein
either
Q is unsubstituted, and is phenyl,
or
Q is unsubstituted, and is pyridin-2-yl,
or
  Q is unsubstituted, and is pyridin-3-yl,
or
Q is unsubstituted, and is furan-2-yl,
or
Q is cyclohexyl;

and the salts thereof.

Compounds according to aspect a of the present invention to be in more particular emphasized include those compounds of formula Ia, Ib or Ic as shown below wherein
Ra is —C(O)R1, in which
either
R1 is (R2)-methyl, or 2-(R2)-ethyl, in which
R2 is pyridin-2-yl, pyridin-3-yl or pyridin-4-yl;

and wherein
either
Q is unsubstituted, and is phenyl,
or
Q is unsubstituted, and is pyridin-2-yl,
or
Q is unsubstituted, and is pyridin-3-yl,
or
Q is unsubstituted, and is furan-2-yl,
or
Q is cyclohexyl;

and the salts thereof.

In the compounds of formula I according to the present invention, the significances mentioned in the following details/subdetails and/or variants/subvariants are of concern individually or in any possible single or multiple combination thereof:

A first embodimental detail (detail a) of the compounds of formula I according to this invention includes those compounds of formula I, in which
Ra is —C(O)R1, in which
R1 is 1-4C-alkyl, such as e.g. methyl, ethyl, propyl or butyl.

A second embodimental detail (detail b) of the compounds of formula I according to this invention includes those compounds of formula I, in which
Ra is —C(O)R1, in which
R1 is 1-4C-alkyl, such as e.g. methyl, ethyl or propyl, which is mono-substituted by R2, in which
R2 has one of the meanings as defined in the compounds mentioned above.

A subdetail (detail b1) of the compounds according to detail b of this invention include those compounds of formula I, in which
R1 is 1-4C-alkyl, such as e.g. methyl, ethyl or propyl, which is mono-substituted by R2, in which
R2 is 1-4C-alkoxy, 1-4C-alkoxy-2-4C-alkoxy, (1-4C-alkoxy-2-4C-alkoxy)-2-4C-alkoxy, hydroxyl, 1-4C-alkoxycarbonyl, phenyl-1-4C-alkoxy, 1-4C-alkylcarbonyloxy, carboxyl, mono- or di-1-4C-alkylaminocarbonyl, carbamoyl, 1-4C-alkylcarbonylamino, 1-4C-alkylcarbonyl, or Har, in which
Har has one of the meanings as defined in the compounds mentioned above.

A further subdetail (detail b2) of the compounds according to detail b of this invention include those compounds of formula I, in which
R1 is 1-4C-alkyl, such as e.g. methyl, ethyl or propyl, which is mono-substituted by R2, in which
R2 is 1-4C-alkoxy, 1-4C-alkoxy-2-4C-alkoxy, (1-4C-alkoxy-2-4C-alkoxy)-2-4C-alkoxy, hydroxyl, 1-4C-alkoxycarbonyl, phenyl-1-4C-alkoxy, 1-4C-alkylcarbonyloxy, carboxyl, mono- or di-1-4C-alkylaminocarbonyl, carbamoyl, or 1-4C-alkylcarbonylamino.

A further subdetail (detail b3) of the compounds according to detail b of this invention include those compounds of formula I, in which
R1 is 1-4C-alkyl, such as e.g. methyl, ethyl or propyl, which is mono-substituted by R2, in which R2 is 1-4C-alkoxy, 1-4C-alkoxy-2-4C-alkoxy, (1-4C-alkoxy-2-4C-alkoxy)-2-4C-alkoxy, hydroxyl, 1-4C-alkoxycarbonyl, phenyl-1-4C-alkoxy, 1-4C-alkylcarbonyloxy, or carboxyl.

A further subdetail (detail b4) of the compounds according to detail b of this invention include those compounds of formula I, in which R1 is 1-4C-alkyl, such as e.g. methyl, ethyl or propyl, which is mono-substituted by R2, in which R2 is 1-2C-alkoxy, 1-2C-alkoxy-ethoxy, (1-2C-alkoxy-ethoxy)-ethoxy, hydroxyl, 1-2C-alkoxycarbonyl, 1-2C-alkylcarbonyloxy, or carboxyl.

A further subdetail (detail b5) of the compounds according to detail b of this invention include those compounds of formula I, in which R1 is 1-4C-alkyl, such as e.g. methyl, ethyl or propyl, which is mono-substituted by R2, in which R2 is Har, in which Har is optionally substituted by one or two substituents independently selected from R10 as defined in the compounds mentioned above, and is
 a 5-membered monocyclic heteroaryl radical comprising one to four heteroatoms independently selected from nitrogen, oxygen and sulphur, such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl,
whereby said Har radical is attached to the adjacent 1-4C-alkyl radical via a ring carbon or ring nitrogen atom.

A further subdetail (detail b6) of the compounds according to detail b of this invention include those compounds of formula I, in which R1 is 1-4C-alkyl, such as e.g. methyl, ethyl or propyl, which is mono-substituted by R2, in which R2 is Har, in which Har is optionally substituted by one or two substituents independently selected from R10 as defined in the compounds mentioned above, and is
 a 6-membered monocyclic heteroaryl radical comprising one or two nitrogen atoms, such as e.g. any one selected from pyridinyl, pyrazinyl, pyridazinyl and pyrimidinyl,
whereby said Har radical is attached to the adjacent 1-4C-alkyl radical via a ring carbon atom.

A further subdetail (detail b7) of the compounds according to detail b of this invention include those compounds of formula I, in which R1 is 1-4C-alkyl, such as e.g. methyl, ethyl or propyl, which is mono-substituted by R2, in which R2 is morpholino.

A further subdetail (detail b8) of the compounds according to detail b of this invention include those compounds of formula I, in which R1 is 1-4C-alkyl, such as e.g. methyl, ethyl or propyl, which is mono-substituted by R2, in which R2 is Har, in which Har is optionally substituted by one or two substituents independently selected from R10 as defined in the compounds mentioned above, and is pyridinyl.

A further subdetail (detail b9) of the compounds according to detail b of this invention include those compounds of formula I, in which R1 is 1-4C-alkyl, such as e.g. methyl, ethyl or propyl, which is mono-substituted by R2, in which R2 is Har, in which Har is optionally mono-substituted by R10, and is pyridinyl, imidazolyl (e.g. imidazol-1-yl) or pyrazolyl (e.g. pyrazol-1-yl), in which R10 is 1-4C-alkyl, such as e.g.

Har is pyridinyl, imidazol-1-yl, pyrazol-1-yl, 1N-(methyl)-imidazolyl or 1N-(methyl)-pyrazolyl.

A further subdetail (detail b10) of the compounds according to detail b of this invention include those compounds of formula I, in which R1 is 1-4C-alkyl, such as e.g. methyl, ethyl or propyl, which is mono-substituted by R2, in which R2 is Har, in which Har is unsubstituted, and is pyridinyl.

A further subdetail (detail b11) of the compounds according to detail b of this invention include those compounds of formula I, in which R1 is 1-4C-alkyl, such as e.g. methyl, ethyl or propyl, which is mono-substituted by R2, in which R2 is methoxy, ethoxy, hydroxyl, methoxycarbonyl, methylcarbonyloxy, or 2-methoxyethoxy.

A further subdetail (detail b12) of the compounds according to detail b of this invention include those compounds of formula I, in which R1 is 1-4C-alkyl, such as e.g. methyl, ethyl or propyl, which is mono-substituted by R2, in which R2 is 1-4C-alkoxy, such as e.g. methoxy or ethoxy, or hydroxyl.

Another subdetail (detail b12') of the compounds according to detail b of this invention include those compounds of formula I, in which R1 is 1-4C-alkyl, such as e.g. methyl, ethyl or propyl, which is mono-substituted by R2, in which R2 is 2-methoxyethoxy.

A further subdetail (detail b13) of the compounds according to detail b of this invention include those compounds of formula I, in which R1 is (R2)-methyl, 2-(R2)-ethyl, or 3-(R2)-propyl, in which R2 is methoxy, ethoxy, hydroxyl, methylcarbonyloxy, or 2-methoxyethoxy.

A further subdetail (detail b14) of the compounds according to detail b of this invention include those compounds of formula I, in which R1 is (R2>methyl, or 2-(R2)-ethyl, in which R2 is methoxy, hydroxyl, or 2-methoxyethoxy.

A further subdetail (detail b15) of the compounds according to detail b of this invention include those compounds of formula I, in which
R1 is propyl or butyl, each of which is bisubstituted by hydroxyl on different carbon atoms, such as e.g. 2,3-dihydroxy-propyl.

A further subdetail (detail b16) of the compounds according to detail b of this invention include those compounds of formula I, in which
R1 is (2-methoxyethoxy)methyl.

A further subdetail (detail b17) of the compounds according to detail b of this invention include those compounds of formula I, in which
R1 is methoxymethyl.

A further subdetail (detail b18) of the compounds according to detail b of this invention include those compounds of formula I, in which
R1 is 2-methoxyethyl.

A further subdetail (detail b19) of the compounds according to detail b of this invention include those compounds of formula I, in which
R1 is hydroxymethyl.

A further subdetail (detail b20) of the compounds according to detail b of this invention include those compounds of formula I, in which
R1 is 2-hydroxyethyl.

A further subdetail (detail b21) of the compounds according to detail b of this invention include those compounds of formula I, in which
R1 is pyridylmethyl, 2-pyridylethyl, or 3-pyridylpropyl, such as e.g. pyridin-2-yl-methyl, pyridin-3-yl-methyl, pyridin-4-yl-methyl, 2-(pyridin-2-yl)-ethyl, 2-(pyridin-3-yl)-ethyl or 2-(pyridin-4-yl)-ethyl.

A further subdetail (detail b22) of the compounds according to detail b of this invention include those compounds of formula I, in which
R1 is (Raa)-methyl, or 2-(Raa)-ethyl, in which
either
Raa is pyridinyl,
or
Raa is methoxy, hydroxyl or 2-methoxyethoxy; especially, methoxy or 2-methoxyethoxy.

A further subdetail (detail b23) of the compounds according to detail b of this invention include those compounds of formula I, in which
R1 is pyridylmethyl, such as e.g. pyridin-2-yl-methyl, pyridin-3-yl-methyl or pyridin-4-yl-methyl.

A further subdetail (detail b24) of the compounds according to detail b of this invention include those compounds of formula I, in which
R1 is 2-pyridylethyl, such as e.g. 2-(pyridin-2-yl)-ethyl, 2-(pyridin-3-yl)-ethyl or 2-(pyridin-4-yl)-ethyl.

A further subdetail (detail b25) of the compounds according to detail b of this invention include those compounds of formula I, in which
R1 is (R2)-methyl, 2-(R2)-ethyl or 3-(R2)-propyl, in which
R2 is R201- and/or R202-substituted pyridyl, in which
R201 is methyl,
R202 is methyl.

A further subdetail (detail b26) of the compounds according to detail b of this invention include those compounds of formula I, in which
R1 is (R2)-methyl, 2-(R2)-ethyl or 3-(R2)-propyl, in which
R2 is imidazol-1-yl.

A further subdetail (detail b27) of the compounds according to detail b of this invention include those compounds of formula I, in which
R1 is (R2)-methyl, 2-(R2)-ethyl or 3-(R2)-propyl, in which
R2 is mono- or di-methyl-substituted imidazol-1-yl.

A further subdetail (detail b28) of the compounds according to detail b of this invention include those compounds of formula I, in which
R1 is (Raa)-methyl, 2-(Raa)-ethyl or 3-(Raa)-propyl, in which
Raa is 1N-methyl-imidazolyl.

A further subdetail (detail b29) of the compounds according to detail b of this invention include those compounds of formula I, in which
R1 is (Raa)-methyl or 2-(Raa)-ethyl, in which
Raa is mono- or di-methyl-substituted imidazol-1-yl, such as e.g. 2-methyl-imidazol-1-yl, 4-methyl-imidazol-1-yl or 2,4-dimethyl-imidazol-1-yl.

A further subdetail (detail b30) of the compounds according to detail b of this invention include those compounds of formula I, in which
R1 is 2-(2-methyl-imidazol-1-yl)-ethyl, 2-(4-methyl-imidazol-1-yl)-ethyl or 2-(2,4-dimethylimidazol-1-yl)-ethyl.

A further subdetail (detail b31) of the compounds according to detail b of this invention include those compounds of formula I, in which
R1 is (2-methyl-imidazol-1-yl)-methyl, (4-methyl-imidazol-1-yl)-methyl or (2,4-dimethylimidazol-1-yl)-methyl.

A further subdetail (detail b32) of the compounds according to detail b of this invention include those compounds of formula I, in which
R1 is (Raa)-methyl or 2-(Raa)-ethyl, in which
Raa is 1N-methyl-imidazolyl, such as e.g. 1-methyl-imidazol-2-yl or 1-methyl-imidazol-5-yl.

A further subdetail (detail b33) of the compounds according to detail b of this invention include those compounds of formula I, in which
R1 is (1-methyl-imidazol-2-yl)-methyl or (1-methyl-imidazol-5-yl)-methyl.

A further subdetail (detail b34) of the compounds according to detail b of this invention include those compounds of formula I, in which
R1 is imidazol-1-yl-methyl.

A further subdetail (detail b35) of the compounds according to detail b of this invention include those compounds of formula I, in which
R1 is 2-(imidazol-1-yl)-ethyl.

A third embodimental detail (detail c) of the compounds of formula I according to this invention includes those compounds of formula Ia, in which R1 is any one of the meanings indicated in Table 1 given below.

A fourth embodimental detail (detail d) of the compounds of formula I according to this invention includes those compounds of formula Ic*, in which R1 is any one of the meanings indicated in Table 1 given below.

A fifth embodimental detail (detail e) of the compounds of formula I according to this invention includes those compounds of formula Ic**, in which R1 is any one of the meanings indicated in Table 1 given below.

A sixth embodimental detail (detail f) of the compounds of formula I according to this invention includes those compounds of formula Ib*, in which R1 is any one of the meanings indicated in Table 1 given below.

A seventh embodimental detail (detail g) of the compounds of formula I according to this invention includes those compounds of formula Ib**, in which R1 is any one of the meanings indicated in Table 1 given below.

A first embodimental variant (variant a) of the compounds of formula I according to this invention includes those compounds of formula I, which are from formula Ia

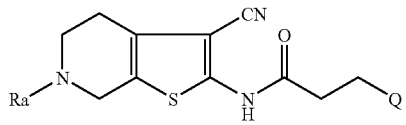
(Ia)

A second embodimental variant (variant b) of the compounds of formula I according to this invention includes those compounds of formula I, which are from formula Ib

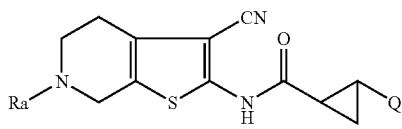
(Ib)

In the context of variant b, one subvariant of variant b includes compounds of formula Ib, in which the radicals —N(H)—C(O)— and Q are located at the opposite side of the plane defined by the cyclopropane ring. A more precise subvariant of variant b includes compounds of formula Ib*, another more precise subvariant of variant b includes compounds of formula Ib**

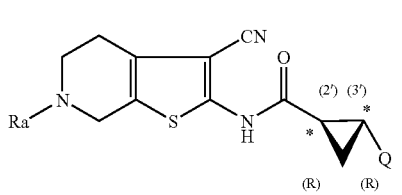
(Ib*)

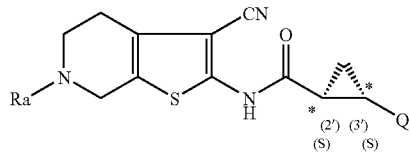
(Ib**)

If, for example, in compounds of formula Ib* Q has one of the meanings given above, then the configuration—according the rules of Cahn, Ingold and Prelog—is R in the position 2' and R in the position 3' as indicated in formula Ib* above.

If, for example, in compounds of formula Ib Q has one of the meanings given above, then the configuration—according the rules of Cahn, Ingold and Prelog—is S in the position 2' and S in the position 3' as indicated in formula Ib above.

A third embodimental variant (variant c) of the compounds of formula I according to this invention includes those compounds of formula I, which are from formula Ic

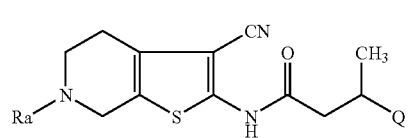
(Ic)

In the context of variant c, one subvariant of variant c includes compounds of formula Ic*, another subvariant of variant c includes compounds of formula Ic**

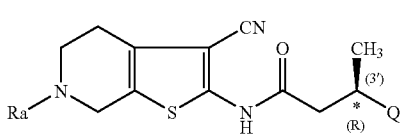
(Ic*)

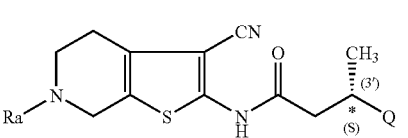
(Ic**)

If, for example, in compounds of formula Ic* Q has the meaning phenyl or Har given above, then the configuration—according the rules of Cahn, Ingold and Prelog—is R in the position 3' indicated in formula Ic* above.

If, for example, in compounds of formula Ic Q has the meaning phenyl or Har given above, then the configuration—according the rules of Cahn, Ingold and Prelog—is S in the position 3' indicated in formula Ic above.

A fourth embodimental variant (variant d) of the compounds of formula I according to this invention includes those compounds of formula I, which are from formulae Id or Id'

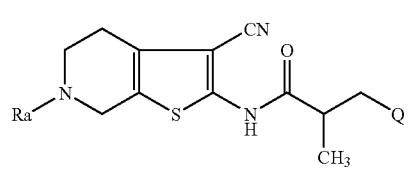
(Id)

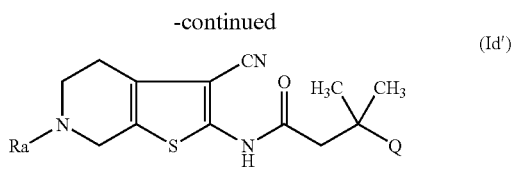

(Id')

In one embodiment, in the meaning of this invention, among the variants a to d, the variants a and c are to be emphasized.

In another embodiment, in the meaning of this invention, among the variants a to d, the variant b is to be emphasized.

A fifth embodimental variant (variant e) of the compounds of formula I according to this invention includes those compounds of any of the formulae Ia, Ib, Ic, Id and Id', in which
Q is optionally substituted by Rba and/or Rbb and/or Rbc, and is phenyl, in which
Rba has one of the meanings as defined in the compounds mentioned above,
Rbb has one of the meanings as defined in the compounds mentioned above,
Rbc has one of the meanings as defined in the compounds mentioned above.

A subvariant (variant e1) of the compounds according to variant e of this invention includes those compounds of any of the formulae Ia, Ib, Ic, Id and Id', in which
Q is optionally substituted by Rba and/or Rbb, and is phenyl, in which
Rba is 1-4C-alkyl, halogen, trifluoromethyl, or hydroxyl,
Rbb is 1-4C-alkyl, halogen, trifluoromethyl, or hydroxyl.

A further subvariant (variant e2) of the compounds according to variant e of this invention includes those compounds of any of the formulae Ia, Ib, Ic, Id and Id', in which
Q is optionally substituted by Rba, and is phenyl, in which
Rba is methyl, ethyl, fluorine or chlorine; especially, methyl, fluorine or chlorine.

A further subvariant (variant e3) of the compounds according to variant e of this invention includes those compounds of any of the formulae Ia, Ib, Ic, Id and Id', in which
Q is any one selected from the group consisting of phenyl, 2-chlorophenyl, 2-methylphenyl, 2-fluorophenyl, 3-chlorophenyl, 3-methylphenyl, 3-fluorophenyl, 4-chlorophenyl, 4-methylphenyl and 4-fluorophenyl; especially, 2-chlorophenyl, 2-methylphenyl, 2-fluorophenyl, 3-chlorophenyl, 3-methylphenyl and 3-fluorophenyl.

A further subvariant (variant e4) of the compounds according to variant e of this invention includes those compounds of any of the formulae Ia, Ib, Ic, Id and Id', in which
Q is unsubstituted, and is phenyl.

A further subvariant (variant e5) of the compounds according to variant e of this invention includes those compounds of any of the formulae Ia, Ib, Ic, Id and Id', in which
Q is 2-(Rba)-phenyl, in which
Rba is methyl, ethyl, fluorine or chlorine.

A further subvariant (variant e6) of the compounds according to variant e of this invention includes those compounds of any of the formulae Ia, Ib, Ic, Id and Id', in which
Q is 3-(Rba)-phenyl, in which
Rba is methyl, ethyl, fluorine or chlorine.

A further subvariant (variant e7) of the compounds according to variant e of this invention includes those compounds of formula Ia, Ib or Ic, in which
Q is 2-(Rba)-phenyl, in which
Rba is chlorine, methyl or ethyl.

A further subvariant (variant e8) of the compounds according to variant e of this invention includes those compounds of formula Ia, Ib or Ic, in which
Q is (Rbb)-substituted 2-(Rba)-phenyl, in which
Rba is chlorine, methyl or ethyl,
Rbb is fluorine, chlorine or methyl.

A further subvariant (variant e9) of the compounds according to variant e of this invention includes those compounds of any of the formulae Ia, Ib and Ic, in which
Q is 2-(Rba)-phenyl, in which
Rba is methyl, ethyl, fluorine or chlorine; especially, methyl, fluorine or chlorine.

A further subvariant (variant e10) of the compounds according to variant e of this invention includes those compounds of any of the formulae Ia, Ib and Ic, in which
Q is 3-(Rba)-phenyl, in which
Rba is methyl, ethyl, fluorine or chlorine; especially, methyl, fluorine or chlorine.

A further subvariant (variant e11) of the compounds according to variant e of this invention includes those compounds of any of the formulae Ia, Ib and Ic, in which
Q is unsubstituted, and is phenyl.

A further subvariant (variant e12) of the compounds according to variant e of this invention includes those compounds of formula Ia, in which
Q is unsubstituted, and is phenyl.

A further subvariant (variant e13) of the compounds according to variant e of this invention includes those compounds of formula Ib, in which
Q is unsubstituted, and is phenyl.

A further subvariant (variant e14) of the compounds according to variant e of this invention includes those compounds of formula Ic, in which
Q is unsubstituted, and is phenyl.

A sixth embodimental variant (variant f of the compounds of formula I according to this invention includes those compounds of any of the formulae Ia, Ib, Ic, Id and Id', in which
Q is optionally substituted by Rca and/or Rcb, and is Har, in which
Har is a 5-membered monocyclic heteroaryl radical comprising one to four heteroatoms independently selected from nitrogen, oxygen and sulphur, such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl, whereby said Har radical is attached to the parent molecular group via a ring carbon or ring nitrogen atom, Rca has one of the meanings as defined in the compounds mentioned above, Rcb has one of the meanings as defined in the compounds mentioned above.

A subvariant (variant f1) of the compounds according to variant f of this invention include those compounds of any of the formulae Ia, Ib, Ic, Id and Id', in which Q is optionally substituted by Rca and/or Rcb, and is Har, in which Har is furanyl, thiophenyl, imidazol-1-yl or pyrazol-1-yl, Rca is 1-4C-alkyl, Rcb is 1-4C-alkyl.

A further subvariant (variant f2) of the compounds according to variant f of this invention include those compounds of any of the formulae Ia, Ib, Ic, Id and Id', in which Q is furanyl, thiophenyl or dimethylfuranyl, such as e.g. furan-2-yl, thiophen-2-yl or 3,4-dimethylfuran-2-yl.

A further subvariant (variant f3) of the compounds according to variant f of this invention include those compounds of any of the formulae Ia, Ib, Ic, Id and Id', in which Q is methyl-pyrazol-1-yl, such as e.g. 5-methyl-pyrazol-1-yl.

A further subvariant (variant f4) of the compounds according to variant f of this invention include those compounds of any of the formulae Ia, Ib, Ic, Id and Id', in which Q is furanyl, such as e.g. furan-3-yl or, especially, furan-2-yl.

A further subvariant (variant f5) of the compounds according to variant f of this invention include those compounds of any of the formulae Ia, Ib, Ic, Id and Id', in which Q is thiophenyl, such as e.g. thiophen-3-yl or, especially, thiophen-2-yl.

A further subvariant (variant f6) of the compounds according to variant f of this invention include those compounds of any of the formulae Ia, Ib, Ic, Id and Id', in which Q is a radical of the following formula

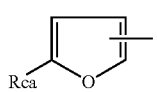

which is attached to the parent molecular group via any possible ring carbon atom, and in which Rca is methyl or chlorine.

A further subvariant (variant f7) of the compounds according to variant f of this invention include those compounds of any of the formulae Ia, Ib, Ic, Id and Id', in which Q is a radical of the following formula

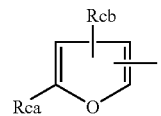

which is attached to the parent molecular group via any possible ring carbon atom, and in which Rca is methyl or chlorine, and Rcb is attached to any possible ring carbon atom, and is methyl.

A further subvariant (variant f8) of the compounds according to variant f of this invention include those compounds of any of the formulae Ia, Ib, Ic, Id and Id', in which Q is a radical of the following formula

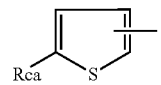

which is attached to the parent molecular group via any possible ring carbon atom, and in which Rca is methyl or chlorine.

A further subvariant (variant f9) of the compounds according to variant f of this invention include those compounds of any of the formulae Ia, Ib, Ic, Id and Id', in which Q is a radical of the following formula

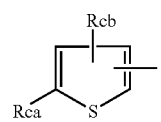

which is attached to the parent molecular group via any possible ring carbon atom, and in which Rca is methyl or chlorine, and Rcb is attached to any possible ring carbon atom, and is methyl.

A further subvariant (variant f10) of the compounds according to variant f of this invention include those compounds of any of the formulae Ia, Ib and Ic, in which Q is 5-(Rca)-furan-2-yl, in which Rca is methyl or chlorine.

A further subvariant (variant f11) of the compounds according to variant f of this invention include those compounds of any of the formulae Ia, Ib and Ic, in which Q is 5-(Rca)-thiophen-2-yl, in which Rca is methyl or chlorine.

A further subvariant (variant f12) of the compounds according to variant f of this invention include those compounds of any of the formulae Ia, Ib and Ic, in which Q is furan-2-yl.

A further subvariant (variant f13) of the compounds according to variant f of this invention include those compounds of any of the formulae Ia, Ib and Ic, in which
Q is thiophen-2-yl.

A seventh embodimental variant (variant g) of the compounds of formula I according to this invention includes those compounds of any of the formulae Ia, Ib, Ic, Id and Id', in which
Q is optionally substituted by Rca and/or Rcb, and is Har, in which
Har is a 6-membered monocyclic heteroaryl radical comprising one or two nitrogen atoms, such as e.g. any one selected from pyridinyl, pyrazinyl, pyridazinyl and pyrimidinyl, whereby said Har radical is attached to the parent molecular group via a ring carbon atom,
Rca has one of the meanings as defined in the compounds mentioned above,
Rcb has one of the meanings as defined in the compounds mentioned above.

A subvariant (variant g1) of the compounds according to variant g of this invention include those compounds of any of the formulae Ia, Ib, Ic, Id and Id', in which
Q is optionally substituted by Rca and/or Rcb, and is Har, in which
Har is pyridinyl,
Rca has one of the meanings as defined in the compounds mentioned above,
Rcb has one of the meanings as defined in the compounds mentioned above.

A further subvariant (variant g2) of the compounds according to variant g of this invention include those compounds of any of the formulae Ia, Ib, Ic, Id and Id', in which
Q is unsubstituted Har, in which
Har is pyridinyl.

A further subvariant (variant g3) of the compounds according to variant g of this invention include those compounds of any of the formulae Ia, Ib, Ic, Id and Id', in which
Q is pyridin-3-yl.

A further subvariant (variant g4) of the compounds according to variant g of this invention include those compounds of any of the formulae Ia, Ib, Ic, Id and Id', in which
Q is pyridin-2-yl.

A further subvariant (variant g5) of the compounds according to variant g of this invention include those compounds of any of the formulae Ia, Ib and Ic, in which
Q is unsubstituted Har, in which
Har is pyridin-2-yl.

A further subvariant (variant g6) of the compounds according to variant g of this invention include those compounds of any of the formulae Ia, Ib and Ic, in which
Q is unsubstituted Har, in which
Har is pyridin-3-yl.

A further subvariant (variant g7) of the compounds according to variant g of this invention include those compounds of formula Ia, in which
Q is unsubstituted Har, in which
Har is pyridin-2-yl.

A further subvariant (variant g8) of the compounds according to variant g of this invention include those compounds of formula Ib, in which
Q is unsubstituted Har, in which
Har is pyridin-2-yl.

A further subvariant (variant g9) of the compounds according to variant g of this invention include those compounds of formula Ic, in which
Q is unsubstituted Har, in which
Har is pyridin-2-yl.

A further subvariant (variant g10) of the compounds according to variant 9 of this invention include those compounds of formula Ia, in which
Q is unsubstituted Har, in which
Har is pyridin-3-yl.

A further subvariant (variant g11) of the compounds according to variant g of this invention include those compounds of formula Ib, in which
Q is unsubstituted Har, in which
Har is pyridin-3-yl.

A further subvariant (variant g12) of the compounds according to variant g of this invention include those compounds of formula Ic, in which
Q is unsubstituted Har, in which
Har is pyridin-3-yl.

An eighth embodimental variant (variant h) of the compounds of formula I according to this invention includes those compounds of any of the formulae Ia, Ib, Ic, Id and Id', in which
Q is optionally substituted by Rda, and is Het, in which
Het is a 3- to 7-membered monocyclic fully saturated heterocyclic ring comprising one or two heteroatoms independently selected from nitrogen, oxygen and sulphur,
such as e.g. any one selected from aziridinyl, azetidinyl, pyrrolidinyl, piperidinyl,
homopiperidinyl,
pyrazolidinyl, imidazolidinyl, piperazinyl, homopiperazinyl, morpholinyl and thiomorpholinyl, whereby said Het radical is attached to the parent molecular group via a ring carbon or ring nitrogen atom,
Rda has one of the meanings as defined in the compounds mentioned above.

A subvariant (variant h1) of the compounds according to variant h of this invention include those compounds of any of the formulae Ia, Ib, Ic, Id and Id', in which
Q is unsubstituted, and is Het, in which
Het is tetrahydrofuranyl, such as e.g. tetrahydrofuran-2-yl.

A ninth embodimental variant (variant i) of the compounds of formula I according to this invention includes those compounds of any of the formulae Ia, Ib, Ic, Id and Id', in which
Q is unsubstituted, and is 3-7C-cycloalkyl, such as e.g. cyclohexyl.

A subvariant (variant i1) of the compounds according to variant i of this invention include those compounds of any of the formulae Ia, Ib and Ic, in which
Q is unsubstituted, and is cyclohexyl or cyclopentyl.

A further subvariant (variant i2) of the compounds according to variant I of this invention include those compounds of formula Ia, in which
Q is unsubstituted, and is cyclohexyl.

A further subvariant (variant i3) of the compounds according to variant i of this invention include those compounds of formula Ib, in which
Q is unsubstituted, and is cyclohexyl.

A further subvariant (variant i4) of the compounds according to variant i of this invention include those compounds of formula Ic, in which
Q is unsubstituted, and is cyclohexyl.

A tenth embodimental variant (variant j) of the compounds of formula I according to this invention includes those compounds of any of the formulae Ia, Ib, Ic, Id and Id', in which
Q is attached via a carbon atom of the benzene ring to the parent molecular group, and is 1,3-benzodioxolyl, 2,2-difluoro-1,3-benzodioxolyl, 2,3-dihydro-1,4-benzodioxinyl, 2,3-dihydrobenzofuranyl, chromenyl or chromanyl.

An eleventh embodimental variant (variant k) of the compounds of formula I according to this invention includes those compounds of any of the formulae Ia, Ib, Ic, Id and Id', in which
Q is any one selected from the group consisting of phenyl, 2-chlorophenyl, 2-methylphenyl, 2-fluorophenyl, 3-chlorophenyl, 3-methylphenyl, 3-fluorophenyl, 4-chlorophenyl, 4-methylphenyl, 4-fluorophenyl,
furanyl, thiophenyl or dimethylfuranyl, such as e.g. furan-2-yl, thiophen-2-yl or 3,4-dimethylfuran-2-yl,
methyl-pyrazol-1-yl, such as e.g. 5-methyl-pyrazol-1-yl,
pyridinyl, such as e.g. pyridin-3-yl,
tetrahydrofuranyl, such as e.g. tetrahydrofuran-2-yl, and cyclohexyl.

A twelfth embodimental variant (variant l) of the compounds of formula I according to this invention includes those compounds of any of the formulae Ia, Ib and Ic, in which
Q is any one selected from the group consisting of 2-chlorophenyl, 2-methylphenyl, 2-fluorophenyl, 3-chlorophenyl, 3-methylphenyl, 3-fluorophenyl,
furanyl, thiophenyl, such as e.g. furan-2-yl or thiophen-2-yl, and
pyridinyl, such as e.g. pyridin-2-yl or pyridin-3-yl.

A thirteenth embodimental variant (variant m) of the compounds of formula I according to this invention includes those compounds of formula Ia, in which Q is any one of the meanings indicated in Table 1 given below.

A fourteenth embodimental variant (variant n) of the compounds of formula I according to this invention includes those compounds of formula Ic*, in which Q is any one of the meanings indicated in Table 1 given below.

A fifteenth embodimental variant (variant o) of the compounds of formula I according to this invention includes those compounds of formula Ic**, in which Q is any one of the meanings indicated in Table 1 given below.

A sixteenth embodimental variant (variant p) of the compounds of formula I according to this invention includes those compounds of formula Ib*, in which Q is any one of the meanings indicated in Table 1 given below.

A seventeenth embodimental variant (variant q) of the compounds of formula I according to this invention includes those compounds of formula Ia, in which R1 is any one of the meanings indicated in Table 1 given below.

An eighteenth embodimental variant (variant r) of the compounds of formula I according to this invention includes those compounds of formula Ic*, in which R1 is any one of the meanings indicated in Table 1 given below.

A nineteenth embodimental variant (variant s) of the compounds of formula I according to this invention includes those compounds of formula Ic**, in which R1 is any one of the meanings indicated in Table 1 given below.

A twentieth embodimental variant (variant t) of the compounds of formula I according to this invention includes those compounds of formula Ib*, in which R1 is any one of the meanings indicated in Table 1 given below.

It is to be understood that the present invention includes any or all possible combinations and subsets of the details, variants, subdetails and subvariants defined hereinabove.

When the compounds of formula I are chiral compounds (e.g. by having one or more chiral centers), the invention refers to all conceivable stereoisomers, like e.g. diastereomers and enantiomers, in substantially pure form as well as in any mixing ratio, including the racemates, as well as the salts thereof.

Accordingly, the stereoisomers of formula Ic* and of formula Ic** and the salts thereof are part of the invention. Likewise, the stereoisomers of formula Ib* and of formula Ib** and the salts thereof are part of the invention.

In general, enantiomerically pure compounds of this invention may be prepared according to art-known processes, such as e.g. via asymmetric syntheses, for example, by preparation and separation of appropriate diastereoisomeric compounds/intermediates, which can be separated by known methods (e.g. by chromatographic separation or (fractional) crystallization from a suitable solvent), or by using chiral synthons or chiral reagents; by chromatographic separation on chiral separating columns; by means of salt formation of the racemic compounds with optically active acids or bases, subsequent resolution of the salts and release of the desired compound from the salt; by derivatization with chiral auxiliary reagents, subsequent diastereomer separation and removal of the chiral auxiliary group; by resolution via diastereomeric inclusion compounds (e.g. complexes or clathrates); by kinetic resolution of a racemate (e.g. by enzymatic resolution); by enantioselective (preferential) crystallization (or crystallization by entrainment) from a conglomerate of enantiomorphous crystals under suitable conditions; or by (fractional) crystallization from a suitable solvent e.g. in the presence of a chiral auxiliary.

Exemplary compounds according to the present invention may include, without being restricted thereto, any compound selected from those compounds of formula I mentioned in the following examples, the enantiomers (e.g., when the compound is from formula Ic, in one special embodiment, the enantiomer having the formula Ic* and, in another special embodiment, the enantiomer having the formula Ic**, or when the compound is from formula Ib, in one special embodiment, the enantiomer having the formula Ib* and, in another special embodiment, the enantiomer having the formula Ib**) as well as the salts of these compounds and enantiomers.

As interesting exemplary compounds according to this invention any or all of the following compounds of formula Ia, in which Ra is —C(O)R1, are more worthy to be mentioned by means of the substituent meanings for R1 and Q in the Table 1 given below, as well as the salts thereof.

As other interesting exemplary compounds according to this invention any or all of the following compounds of formula Ic, in which Ra is —C(O)R1, are more worthy to be mentioned by means of the substituent meanings for R1 and Q in the Table 1 given below, as well as the enantiomers and the salts of these compounds and enantiomers.

As other interesting exemplary compounds according to this invention any or all of the following compounds of formula Ic*, in which Ra is —C(O)R1, are more worthy to be mentioned by means of the substituent meanings for R1 and Q in the Table 1 given below, as well as the salts thereof.

As other interesting exemplary compounds according to this invention any or all of the following compounds of formula Ic**, in which Ra is —C(O)R1, are more worthy to be mentioned by means of the substituent meanings for R1 and Q in the Table 1 given below, as well as the salts thereof.

As other interesting exemplary compounds according to this invention any or all of the following compounds of formula Ib, in which Ra is —C(O)R1, are more worthy to be mentioned by means of the substituent meanings for R1 and Q in the Table 1 given below, as well as the enantiomers and the salts of these compounds and enantiomers.

As other interesting exemplary compounds according to this invention any or all of the following compounds of formula Ib*, in which Ra is —C(O)R1, are more worthy to be mentioned by means of the substituent meanings for R1 and Q in the Table 1 given below, as well as the salts thereof.

As other interesting exemplary compounds according to this invention any or all of the following compounds of formula Ib**, in which Ra is —C(O)R1, are more worthy to be mentioned by means of the substituent meanings for R1 and Q in the Table 1 given below, as well as the salts thereof.

TABLE 1

|  | R1 | Q |
|---|---|---|
| 1.) | 2-(imidazol-1-yl)-ethyl | pyridin-2-yl |
| 2.) | pyridin-2-yl-methyl | pyridin-2-yl |
| 3.) | pyridin-3-yl-methyl | pyridin-2-yl |
| 4.) | pyridin-4-yl-methyl | pyridin-2-yl |
| 5.) | 2-(pyridin-2-yl)-ethyl | pyridin-2-yl |
| 6.) | 2-(pyridin-3-yl)-ethyl | pyridin-2-yl |
| 7.) | 2-(pyridin-4-yl)-ethyl | pyridin-2-yl |
| 8.) | 2-(imidazol-1-yl)-ethyl | pyridin-3-yl |
| 9.) | pyridin-2-yl-methyl | pyridin-3-yl |
| 10.) | pyridin-3-yl-methyl | pyridin-3-yl |
| 11.) | pyridin-4-yl-methyl | pyridin-3-yl |
| 12.) | 2-(pyridin-2-yl)-ethyl | pyridin-3-yl |
| 13.) | 2-(pyridin-3-yl)-ethyl | pyridin-3-yl |
| 14.) | 2-(pyridin-4-yl)-ethyl | pyridin-3-yl |
| 15.) | 2-(imidazol-1-yl)-ethyl | furan-2-yl |
| 16.) | pyridin-2-yl-methyl | furan-2-yl |
| 17.) | pyridin-3-yl-methyl | furan-2-yl |
| 18.) | pyridin-4-yl-methyl | furan-2-yl |
| 19.) | 2-(pyridin-2-yl)-ethyl | furan-2-yl |
| 20.) | 2-(pyridin-3-yl)-ethyl | furan-2-yl |
| 21.) | 2-(pyridin-4-yl)-ethyl | furan-2-yl |
| 22.) | 2-(imidazol-1-yl)-ethyl | thiophen-2-yl |
| 23.) | pyridin-2-yl-methyl | thiophen-2-yl |
| 24.) | pyridin-3-yl-methyl | thiophen-2-yl |
| 25.) | pyridin-4-yl-methyl | thiophen-2-yl |
| 26.) | 2-(pyridin-2-yl)-ethyl | thiophen-2-yl |
| 27.) | 2-(pyridin-3-yl)-ethyl | thiophen-2-yl |

TABLE 1-continued

|  | R1 | Q |
|---|---|---|
| 28.) | 2-(pyridin-4-yl)-ethyl | thiophen-2-yl |
| 29.) | imidazol-1-yl-methyl | pyridin-2-yl |
| 30.) | hydroxymethyl | pyridin-2-yl |
| 31.) | 2-hydroxyethyl | pyridin-2-yl |
| 32.) | imidazol-1-yl-methyl | pyridin-3-yl |
| 33.) | hydroxymethyl | pyridin-3-yl |
| 34.) | 2-hydroxyethyl | pyridin-3-yl |
| 35.) | imidazol-1-yl-methyl | furan-2-yl |
| 36.) | hydroxymethyl | furan-2-yl |
| 37.) | 2-hydroxyethyl | furan-2-yl |
| 38.) | imidazol-1-yl-methyl | thiophen-2-yl |
| 39.) | hydroxymethyl | thiophen-2-yl |
| 40.) | 2-hydroxyethyl | thiophen-2-yl |
| 41.) | 2-(imidazol-1-yl)-ethyl | phenyl |
| 42.) | pyridin-2-yl-methyl | phenyl |
| 43.) | pyridin-3-yl-methyl | phenyl |
| 44.) | pyridin-4-yl-methyl | phenyl |
| 45.) | 2-(pyridin-2-yl)-ethyl | phenyl |
| 46.) | 2-(pyridin-3-yl)-ethyl | phenyl |
| 47.) | 2-(pyridin-4-yl)-ethyl | phenyl |
| 48.) | imidazol-1-yl-methyl | phenyl |
| 49.) | hydroxymethyl | phenyl |
| 50.) | 2-hydroxyethyl | phenyl |
| 51.) | 2-(imidazol-1-yl)-ethyl | cyclohexyl |
| 52.) | pyridin-2-yl-methyl | cyclohexyl |
| 53.) | pyridin-3-yl-methyl | cyclohexyl |
| 54.) | pyridin-4-yl-methyl | cyclohexyl |
| 55.) | 2-(pyridin-2-yl)-ethyl | cyclohexyl |
| 56.) | 2-(pyridin-3-yl)-ethyl | cyclohexyl |
| 57.) | 2-(pyridin-4-yl)-ethyl | cyclohexyl |
| 58.) | imidazol-1-yl-methyl | cyclohexyl |
| 59.) | hydroxymethyl | cyclohexyl |
| 60.) | 2-hydroxyethyl | cyclohexyl |

In the context of Table 1 above, one embodiment refers to any of the substituent meanings 1.) to 28.) given in the Table 1 above; another embodiment refers to any of the substituent meanings 29.) to 60.) given in the Table 1 above.

Among the substituent meanings 1.) to 60.) given in the Table 1 above, the substituents meanings 1.) to 14.), 29.) to 34.), and 41.) to 60.) are to be emphasized.

Among the substituent meanings 1.) to 60.) given in the Table 1 above, the substituents meanings 2.) to 7.), 9.) to 14.), 42.) to 47.), and 52.) to 57.) are to be in particular emphasized.

Compounds of formula I according to the present invention can be prepared as described below or as shown in the following reaction schemes, or as disclosed in WO2004/024066 or, particularly, WO2004/024065, the disclosure of which is incorporated herein, or similarly or analogously thereto according to preparation procedures or synthesis strategies known to the person skilled in the art.

Accordingly, compounds of formula I according to the present invention can be obtained as specified by way of example in the following examples, or similarly or analogously thereto.

Thus, as shown in reaction scheme below, a compound of formula III, in which Ra has the meanings given above, can be condensed with malonitrile in the presence of sulfur and a suitable base, such as for example an amine (e.g. diethyl amine or morpholine) to give corresponding compounds of formula II in a manner known to the person skilled in the art (e.g. according to a Gewald reaction) or as described in the following examples.

Compounds of formula III are known or can be obtained in an art-known manner, or analogously or similarly thereto.

Compounds of formula II can be reacted with compounds of formula Rb—C(O)—X, in which Rb has the meanings mentioned above and X is a suitable leaving group, preferably a chlorine atom, in an acylation reaction under conditions habitual per se to give the desired compounds of formula I, in which Ra and Rb have the meanings given above.

Alternatively, compounds of the formula I can also be prepared from the corresponding compounds of formula II and corresponding compounds of formula Rb—C(O)—X, in which X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N', N'-tetramethyluronium tetrafluoroborate or O-(benzotriazol-1-yl)-N,N,N',N'-tetramethyl-uronium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride (EDC).

respectively, by Horner-Wadsworth-Emmons reaction, and then hydration reaction and, if necessary, hydrolysis of the corresponding esters obtained.

β-Methyl-propionic acids can be also obtained as given in J. Org. Chem. 61, 16, 1996, 5510-5516 and Tetrahedron Lett. 37, 10, 1996, 1683-1686 and subsequent hydration, such as e.g. described in the following examples, or analogously or similarly thereto.

In this context, there are several options for the synthesis of enantomerically pure β-methyl-propionic acids known in literature, e.g.:

asymmetric addition of phenylboronic acids to α-,β-unsaturated esters using chiral catalysts (see e.g. S. Sakuma, M. Sakai, R. Itooka, N. Miyaura J. Org. Chem. 2000, 65, 5951-5955), asymmetric Michael addition to α-,β-unsaturated esters using chiral auxiliaries (see e.g. J. Ezquerra, L. Prieto, C. Avendano, J. L. Martos, E. dela Cuesta, Tetrahedr. Lett. 1999, 40, 1575-1578),

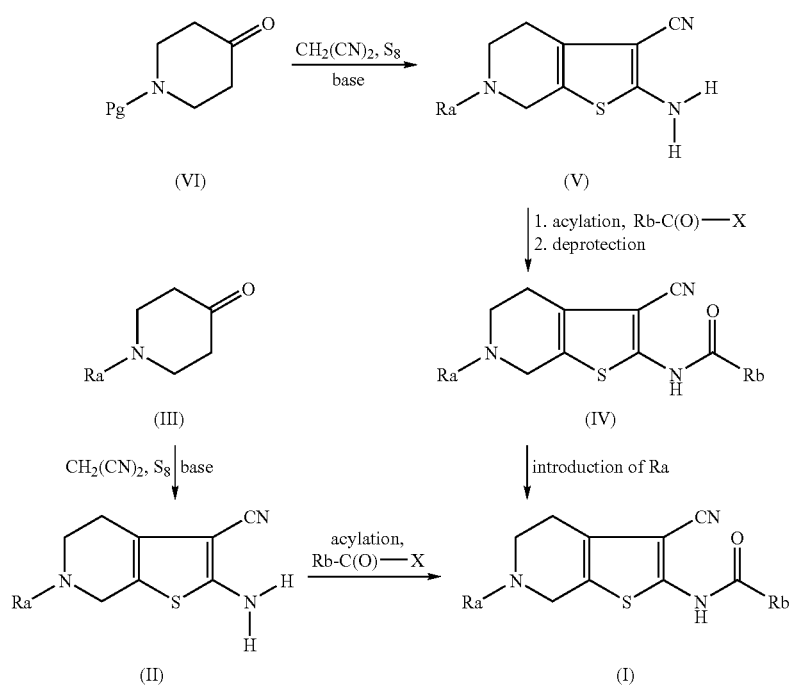

Acid derivatives of formula Rb—C(O)—X are known, commercially available or can be prepared as it is known for the skilled person, e.g. from the corresponding carboxylic acids.

Carboxylic acids of formula Rb—C(O)—OH are known, commercially available or can be obtained as it is habitual for the skilled person, e.g. analogously or similarly to standard procedures.

Thus, for example, carboxylic acids of formula Rb—C(O)—OH, in which Rb is -T-Q, in which T is 1-6C-alkylene, as defined above, especially those, in which Rb is —CH₂—CH₂-Q or —CH₂—CH(CH₃)-Q, in which Q has the meanings given above, can be obtained via CC-coupling reactions, such as e.g. by Heck or Knoevenagel reaction or, in particular, starting from aldehydes of the formula Q-CHO or ketones, especially methylketones, of the formula Q-C(O)CH₃, asymmetric hydrogenation of α-,β-unsaturated esters and acids (see e.g. T. Uemura, X. Zhang, K. Matsumura, et al., J. Org. Chem. 1996, 61, 5510-5516; or W. Tang, W. Wang, X. Zhang Angew. Chem. Int. Ed 2003, 42(8), 943-946), or asymmetric hydrosilylation of α-,β-unsaturated esters (see e.g. B. Lipshutz, J. M. Servesko, B. R. Taft: J. Am. Chem. Soc. 2004, 126(27), 8352-8353).

Further on, for example, carboxylic acids of formula Rb—C(O)—OH, in which Rb is -T-Q, in which T is 1,2-cyclopropylene and Q has the meanings given above, can be obtained, starting from aldehydes of the formula Q-CHO, via Knoevenagel or Horner-Wadsworth-Emmons reaction, and then cyclopropanation reaction of the double bond (e.g. by Simmons-Smith reaction or, in particular, by Corey-Chaykovsky cyclopropanation reaction using dimethylsulfoxonium methylide) and, if necessary, hydrolysis of the corresponding esters obtained.

In this context, there are several options for asymmetric cyclopropanation known in literature, which may be used for the synthesis of enantiomerically pure cyclopropanecarboxylic acids, e.g.:

- asymmetric addition of a metal (e.g. Cu, Rh, Ru, Co) carbene or carbenoid complex to an alkene (see e.g. Organic Letters 2004 Vol. 6, No. 5, 855-857),
- catalytic asymmetric cyclopropanation using diazomethane or a derivative thereof and a chiral transition metal (e.g. Cu) complex (see e.g. Tetrahedron Asymmetry 2003, 14, 867-872),
- asymmetric Simmons-Smith cyclopropanation, or
- asymmetric Michael-initiated ring closure (MIRC) using ylides, e.g. reaction of chiral sulfonium ylides with acrylic acid derivatives (see e.g. Synlett 2005, 10, 1621-1623).

Aldehydes of formula Q-CHO and methylketones of formula Q-C(O)CH$_3$, in which Q has the meanings given above, are known or can be obtained in a manner customary for the skilled person analogously or similarly to known compounds.

In an alternative synthesis route, compounds of formula VI, in which PG is a suitable temporary protective group, such as for example tertbutoxycarbonyl (Boc) or one of those mentioned in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000), can be condensed with malononitrile in the presence of sulfur and a suitable base as described above to give corresponding compounds of formula V.

Compounds of formula VI are known or can be obtained in an art-known manner.

Compounds of formula V can be acylated with compounds of formula Rb—C(O)—X analogously as mentioned above. Optionally, said amide bond formation can be obtained under microwave assistance. Subsequential deprotection of the protective group PG in a manner customary per se for the skilled person gives compounds of formula IV, in which Rb has the meanings as mentioned above.

Compounds of formula IV can be converted into desired compounds of formula I by introduction of the group Ra via amide bond formation reaction. This amide bond formation reaction can be carried out in a manner as described afore, or analogously to the methods known to the person skilled in the art, or as described by way of example in the following examples. The appropriate starting compounds of formula R1—C(O)—X, in which R1 and X have the meanings given above, are art-known or can be obtained according to art-known procedures or analogously or similarly as disclosed for known compounds.

When Har-substituted carboxylic acids, in which Har has the meanings given above (e.g. substituted or unsubstituted pyridyl or imidazolyl), are used as starting compounds in an amide formation reaction according to this invention, these carboxylic acids can be obtained via CC-coupling reaction or nucleophilic substitution reaction of appropriate building blocks.

Thus, e.g. Har-substituted propionic acids, in which Har has the meanings given above (e.g. substituted or unsubstituted pyridyl or 1-methyl-imidazolyl) can be obtained by Heck or Knoevenagel reaction or, in particular, starting from aldehydes of the formula Har-CHO by Horner-Wadsworth-Emmons reaction, and then hydration reaction and, if necessary, hydrolysis of the corresponding esters obtained.

Aldehydes of the formula Har-CHO are known or can be obtained as it is known for the skilled person, such as e.g. from the corresponding heteroaromatic compounds by formylation reaction.

Some aldehydes can be obtained as described e.g. for 4-methoxy-pyridin-2-carbaldehyde in Ashimori et al, Chem Pharm Bull 38, 2446-2458 (1990) or analogously or similarly thereto.

Har-substituted carboxylic acids (e.g. propionic acids), in which Har has the meanings given above (e.g. substituted or unsubstituted pyridyl), can be also obtained as described in WO03080607 or WO2005/030770 or analogously or similarly thereto, such as e.g. 3-(4-methoxypyridin-2-yl)propionic acid is described as compound A1 in WO03080607, or analogously or similarly thereto.

It is to be understood for the skilled worker, that certain compounds according to this invention can be converted into further compounds of this invention by art-known synthesis strategies and reactions habitual per se to a person of ordinary skill in the art.

Therefore, optionally, compounds of formula I can be also converted into further compounds of formula I by methods known to one of ordinary skill in the art. More specifically, for example, from compounds of the formula I in which a) R2 is acyloxy, such as e.g. acetoxy, the corresponding free hydroxyl compounds can be obtained by removal of the acyl group, such as e.g. by saponification reaction;
b) Het is a cyclic acetal or ketal, such as e.g. the 2,2-dimethyl-[1,3]dioxolan acetal, the corresponding free dihydroxy compounds can be obtained by cleavage of the acetal or ketal, such as e.g. by deacetalization reaction;
c) R2 is an ester group, such as e.g. methoxycarbonyl, the corresponding free carboxyl compounds can be obtained by deesterification, such as e.g. by saponification reaction.

The methods mentioned under a) to c) can be expediently carried out analogously to the methods known to the person skilled in the art or as described by way of example in the following examples.

Optionally, compounds of the formula I can be converted into their salts, or, optionally, salts of the compounds of the formula I can be converted into the free compounds. Corresponding processes are habitual per se to the skilled person.

When one of the final steps or purification is carried out under the presence of an inorganic or organic acid (e.g. hydrochloric, trifluoroacetic, acetic or formic acid or the like), the compounds of formula I may be obtained—depending on their individual chemical nature and the individual nature of the acid used—as free base or containing said acid in an stoechiometric or non-stoechiometric quantity. The amount of the acid contained can be determined according to art-known procedures, e.g. by titration.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as methanol, ethanol or isopropanol) which contains the desired add or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds of formula I. All these other possible synthesis routes are also part of this invention.

The present invention also relates to intermediates, including their salts, methods and processes useful in synthesizing compounds according to this invention.

Having described the invention in detail, the scope of the present invention is not limited only to those described characteristics or embodiments. As will be apparent to persons skilled in the art, modifications, analogies, variations, derivations, homologisations, alternatives and adaptations to the described invention can be made on the base of art-known knowledge and/or, particularly, on the base of the disclosure (e.g. the explicite, implicate or inherent disclosure) of the present invention without departing from the spirit and scope of this invention as defined by the scope of the appended claims.

The following examples serve to illustrate the invention further without restricting it. Likewise, further compounds of formula I including their salts, whose preparation is not explicitly described, can be prepared in an analogous or similar manner or in a manner familiar per se to the person skilled in the art using customary process techniques.

Any or all of the compounds of formula I according to the present invention which are mentioned in the following examples, particularly those which are mentioned as final compounds, as well as their salts, stereoisomers and salts of the stereoisomers are a preferred subject of the present invention.

In the examples, MS stands for mass spectrum, M is the molecular ion in mass spectroscopy, calc. for calculated, fnd. for found, Boc for the tertbutoxycarbonyl group, EDC or EDCI for 1-ethyl-3-(3-dimethylaminopropyl)carbodiimide hydrochloride and other abbreviations have their meanings customary per se to the skilled person.

Further on, according to common practice in stereochemistry, the term "(RS)" characterizes a racemate comprising the one enantiomer having the configuration R and the other enantiomer having the configuration S; each of these enantiomers in pure form as well as their mixtures including the racemic mixtures is part of this invention.

Yet further on, according to common practice in stereochemistry, when more than one chiral center is present in a molecule, the symbols RS and SR are used to denote the specific configuration of each of the chiral centers of a racemate. In more detail, for example, the term "(1RS,2RS)" stands for a racemate (racemic mixture) comprising the one enantiomer having the configuration (1R,2R) and the other enantiomer having the configuration (1S,2S); each of these enantiomers in pure form as well as their mixtures including the racemic mixtures is part of this invention.

EXAMPLES

Final Compounds

A. General Procedure for Amide Bond Formation a) Starting from the Trifluoroacetate Salt of the Respective Free Amine:

To a solution of the appropriate acid (1.5 mmol) in dichloromethane (5 ml), carbonyldiimidazole (CDI, 1.78 mmol) is added. The reaction vessel is equipped with a bubbler, the mixture is stirred until the gas evolution is completed (30 min, approximately). Then, a mixture of the suspension of the appropriate starting trifluoroacetate salt of the free amine in dichloromethane (10 ml) and triethylamine (0.2 g, 2 mmole) is added to the reaction mixture. Stirring is continued for 18 to 24 hours at room temperature, the reaction is monitored by TLC.

Work up a1: if the reaction mixture is a solution, it is extracted by three portions of 5% sodium hydrogencarbonate (10 ml each) and once by water (10 ml), the organic layer is evaporated and the residue subjected to purification.

Work up a2: if the reaction mixture is a suspension, the solid product is filtered off. If the amount of this solid product is not sufficient, the mother liquour is further worked up as procedure A.

Purification: The majority of the products can be recrystallized from acetonitrile or ethanol, in some cases by simple trituration of the organic residue with acetonitrile or ethanol. After filtration, the crystals are washed with diethyl ether. In case this procedure does not yield clean products, flash chromatography is performed using mixtures of dichloromethane and methanol as eluent.

b) Starting from the Respective Free Amine Using EDCI

A mixture of the appropriate starting base (1 mmol), the appropriate acid (1.5 mmol), ethyl-dimethylaminopropylcarbodiimide (EDCI, 0.29 g, 1.5 mmol), 4-dimethylaminopyridine (DMAP, 0.25 g, 0.2 mmol) and water-free dichloromethane (10 ml) are stirred at room temperature for 18 to 24 hours. The reaction mixture is monitored by TLC. The reaction mixture is worked up as in the reactions carried out with CDI.

c) Using Acid Chlorides

To a suspension of the appropriate starting trifluoroacetate salt (1 mmol) in dichloromethane (10 ml) triethylamine (0.4 g, 4 mmol) is added. The formed solution is added to a solution of the appropriate acid chloride (1.2 mmol) in dichloromethane (10 ml) dropwise at 0° C. with stirring and, then, stirring is continued for 24 h at room temperature. The mixture is evaporated and the residue dissolved in dichloromethane. This solution is extracted twice by water (15 ml) and once by saturated sodium chloride solution (15 ml). Purification is carried out as described in procedures a) and b).

d) Using CDI Under Microwave Assistance 3.5 eq of the appropriate acid are dissolved in dichloromethane and 2.5 eq CDI is added. After the gas evolution has subsided, a solution of the appropriate amino building block in dichloromethane containing 5 eq triethylamine is added. The reaction mixture is heated in a sealed tube for 3 hours at 75° C. under microwave assistance. Purification is carried out as described in procedures a) and b).

The following compounds can be prepared according to general procedure A starting from N-(3-cyano-4,5,6,7-tetrahydro-thieno[2,3-c]pyridin-2-yl)-3-phenyl-propionamide (compound A1) and the appropriate art-known carboxylic acid derivative.

1. N-[3-Cyano-6-(3-pyridin-3-yl-propanoyl)-4,5,6,7-tetrahydro-thieno[2,3c]pyridin-2-yl]-3-phenyl-propionamide

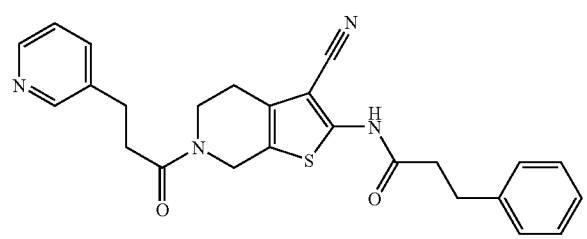

MS: calc.: C, 25; H, 24; N, 4; O, 2; S, (444.56). fnd.: 445.2 [M+H].

2. N-[3-Cyano-6-(2-pyridin-3-yl-ethanoyl)-4,5,6,7-tetrahydro-thieno[2,3-]pyridin-2-yl]-3-phenyl-propionamide

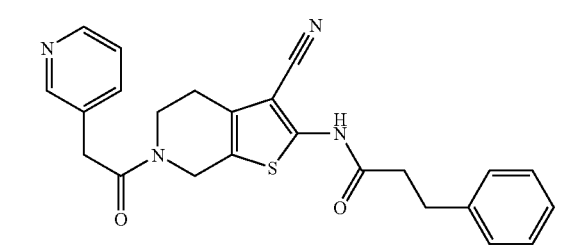

MS: calc.: C, 24; H, 22; N, 4; O, 2; S, (430.53). fnd.: 431.1 [M+H].

3. N-[3-Cyano-6-(2-pyridin-2-yl-ethanoyl)-4,5,6,7-tetrahydro-thieno[2,3c]pyridin-2-yl]-3-phenyl-propionamide

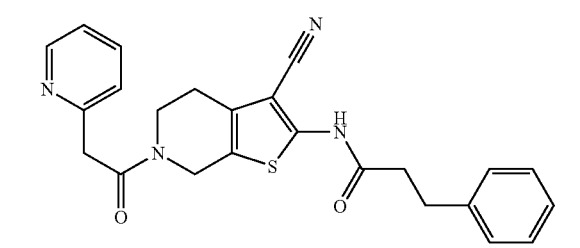

MS: calc.: C, 24; H, 22; N, 4; O, 2; S, (430.53). fnd.: 431.1 [M+H]. -4. N-[3-Cyano-6-(2-methoxy-ethanoyl)-4,5,6,7-tetrahydro-thieno[2,3-]pyridin-2-yl]-3-phenyl-propionamide

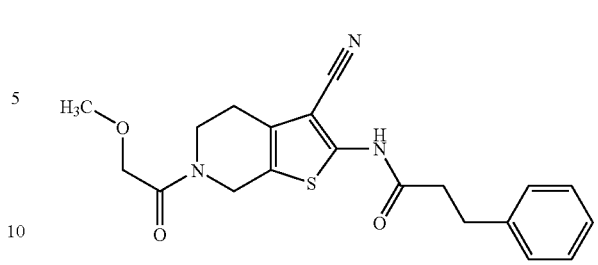

MS: calc.: C, 20; H, 21; N, 3; O, 3; S, (383.47). fnd.: 384.1 [M+H].

5. N-{3-Cyano-6-[2-(2-methoxy-ethoxy)-ethanoyl]-4,5,6,7-tetrahydro-thieno[2,3-c]pyridin-2-yl}-3-phenyl-propionamide

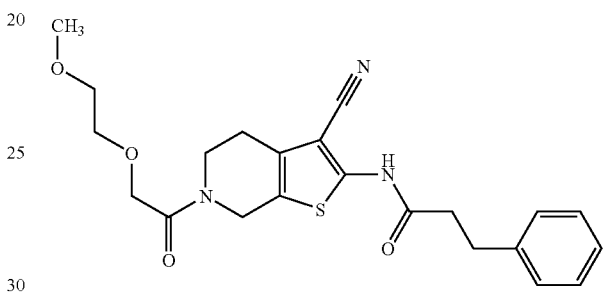

MS: calc.: C, 22; H, 25; N, 3; O, 4; S, (427.53). fnd.: 428.1 [M+H].

6. 4-[3-Cyano-2-(3-phenyl-propanoylamino)-4,7-dihydro-5H-thieno[2,3-c]pyridin-6-yl]-4-oxo-butyric acid methyl ester

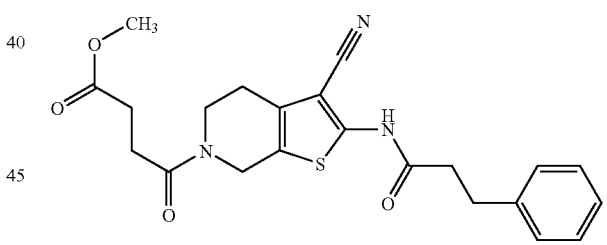

MS: calc.: C, 22; H, 23; N, 3; O, 4; S, (425.51). fnd.: 426 [M+H].

7. Acetic acid 2-[3-cyano-2-(3-phenyl-propanoylamino)-4,7-dihydro-5H-thieno[2,3-c]pyridin-6-yl]-2-oxo-ethyl ester

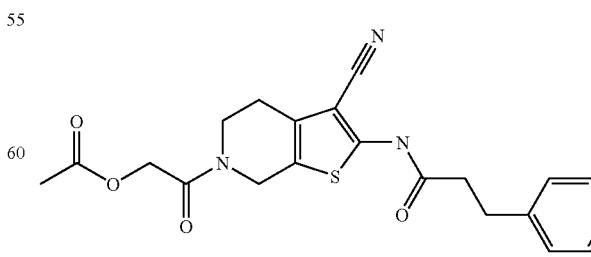

MS: calc.: C, 21; H, 21; N, 3; O, 4; S, (411.48). fnd.: 412 [M+H].

8. N-[3-Cyano-6-(2-hydroxy-ethanoyl)-4,5,6,7-tetrahydro-thieno[2,3-c]pyridin-2-yl]-3-phenyl-propionamide

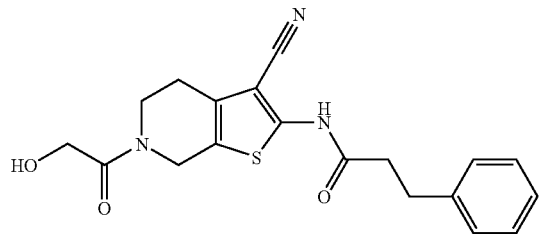

The title compound is prepared from Example 7 by art-known saponification reaction (e.g. using 1N NaOH).

MS: calc.: C, 19; H, 19; N, 3; O, 3; S, (369.45).

Using similar procedures to those described herein above but with suitable choice of starting materials (which are known or which can be obtained according to procedures customary to the skilled person or described herein, or analogously or similarly thereto), the following compounds can be prepared.

The following compounds 49, 61, 68, 69, 71 and 83 may be obtained from the corresponding acetates, which can be obtained using similar procedures to those described herein but with suitable choice of starting materials (e.g. similarly as to attain Example 7), by art-known removal of the acetyl function using for example LiOH or NaOH.

The following compounds 50, 60, 67, 70, 72 and 82 may be obtained from the corresponding amines and beta-propiolactone similarly to Example 48.

The following compounds 19 to 47, 51 to 59, 62 to 66, and 73 to 81 may prepared according to general procedure A' starting from the appropriate starting compounds A1 to A63 and the appropriate carboxylic acids, which are known or which can be obtained according to procedures customary to the skilled person or described herein, or analogously or similarly thereto.

9. N-{3-Cyano 6-[2-(2-methoxy-ethoxy)-ethanoyl]-4,5,6,7-tetrahydro-thieno[2,3-c]pyridin-2-yl}-3-furan-2-yl-propionamide

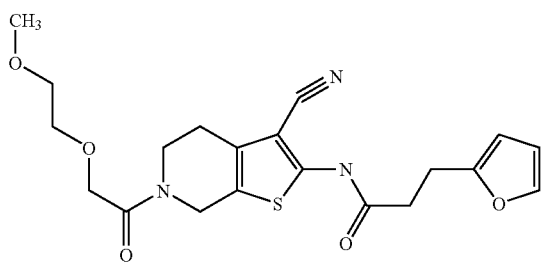

MS: calc.: C, 20; H, 23; N, 3; O, 5; S, (417.49). fnd.: 418.2.

10. N-[3-Cyano-6-(2-pyridin-2-yl-ethanoyl)-4,5,6,7-tetrahydro-thieno[2,3-]pyridin-2-yl]-3-furan-2-yl-propionamide

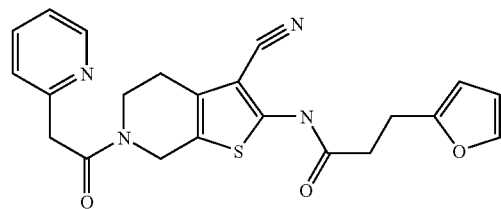

MS: calc.: C, 22; H, 20; N, 4; O, 3; S, (420.49). fnd.: 421.2.

11. N-[3-Cyano-6-(2-pyridin-3-yl-ethanoyl)-4,5,6,7-tetrahydro-thieno[2,3-]pyridin-2-yl]-3-furan-2-yl-propionamide

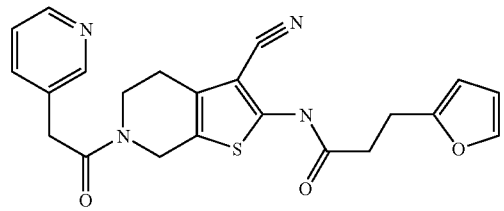

MS: calc.: C, 22; H, 20; N, 4; O, 3; S, (420.49). fnd.: 421.3.

12. N-[3-Cyano-6-(3-pyridin-3-yl-propanoyl)-4,5,6,7-tetrahydro-thieno[2,3-c]pyridin-2-yl]-3-furan-2-yl-propionamide

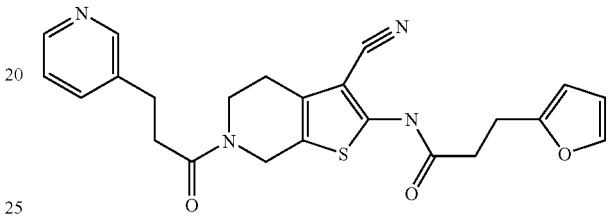

MS: calc.: C, 23; H, 22; N, 4; O, 3; S, (434.52). fnd.: 435.2.

13. N-[3-Cyano-6-(2-methoxy-ethanoyl)-4,5,6,7-tetrahydro-thieno[2,3-]pyridin-2-yl]-3-furan-2-yl-propionamide

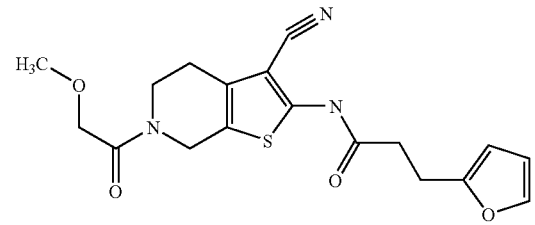

MS: calc.: C, 18; H, 19; N, 3; O, 4; S, (373.43). fnd.: 374.2.

14. N-(6-Butyryl-3-cyano-4,5,6,7-tetrahydro-thieno[2,3-]pyridin-2-yl)-3-furan-2-yl-propionamide

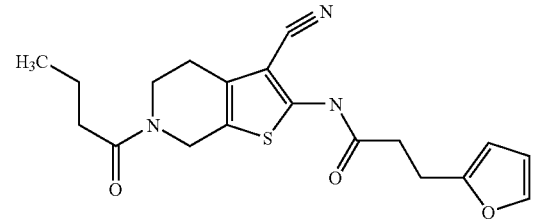

MS: calc.: C, 19; H, 21; N, 3; O, 3; S, (371.46). fnd.: 372.

15. N-[3-Cyano-6-(3-imidazol-1-yl-propanoyl)-4,5,6,7-tetrahydro-thieno[2,3-c]pyridin-2-yl]-3-furan-2-yl-propionamide

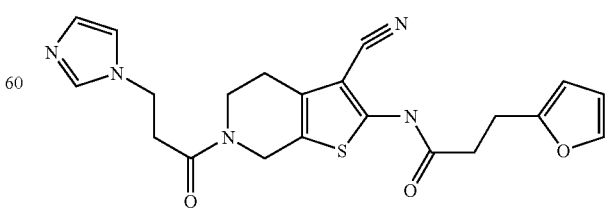

MS: calc.: C, 21; H, 21; N, 5; O, 3; S, (423.5). fnd.: 424.2.

16. N-[3-Cyano-6-(3-imidazol-1-yl-propanoyl)-4,5,6,7-tetrahydro-thieno[2,3-c]pyridin-2-yl]-3-phenyl-propionamide

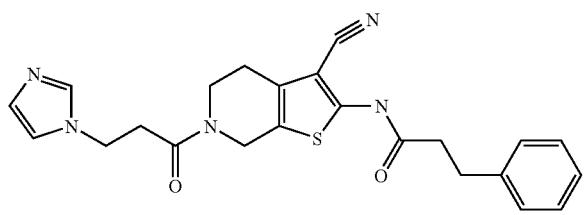

MS: calc.: C, 23; H, 23; N, 5; O, 2; S, (433.54). fnd.: 434.2.

17. N-3-Cyano-6-[3-(4-methyl-piperazin-1-yl)-propanoyl]-4,5,6,7-tetrahydro-thieno[2,3-c]pyridin-2-yl)-3-phenyl-propionamide

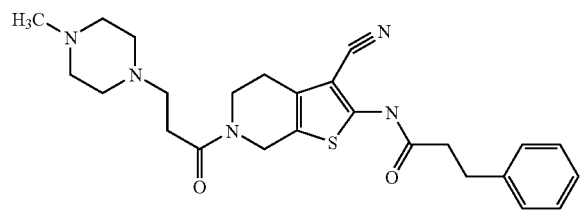

MS: calc.: C, 25; H, 31; N, 5; O, 2; S, (465.62). fnd.: 466.3.

18. N-[3-Cyano-6-(3-morpholin-4-yl-propanoyl)-4,5,6,7-tetrahydro-thieno[2,3-c]pyridin-2-yl]-3-phenyl-propionamide

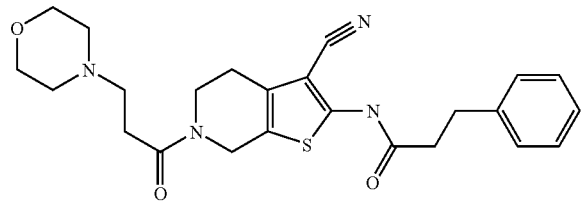

MS: calc.: C, 24; H, 28; N, 4; O, 3; S, (452.58). fnd.: 453.2.

19. N-[3-Cyano-6-(2-imidazol-1-yl-ethanoyl)-4,5,6,7-tetrahydro-thieno[2,3-c]pyridin-2-yl]-3-phenyl-propionamide

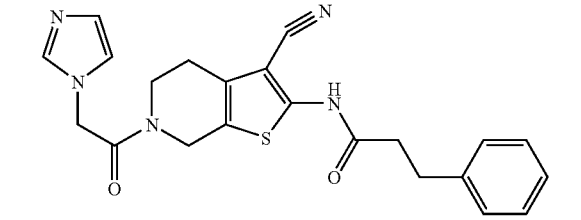

MS: calc.: C, 22; H, 21; N, 5; O, 2; S, (419.51). fnd.: 420.2 [M+H].

20. N-[3-Cyano-6-(2-pyridin-4-yl-ethanoyl)-4,5,6,7-tetrahydro-thieno[2,3-c]pyridin-2-yl]-3-phenyl-propionamide

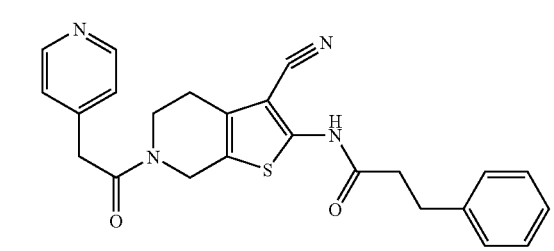

MS: calc.: C, 24; H, 22; N, 4; O, 2; S, (430.53). fnd.: 431.2 [M+H].

21. N-{3-Cyano-6-[3-(2-methyl-benzoimidazol-1-yl)-propanoyl]-4,5,6,7-tetrahydro-thieno[2,3-c]pyridin-2-yl}-3-phenyl-propionamide

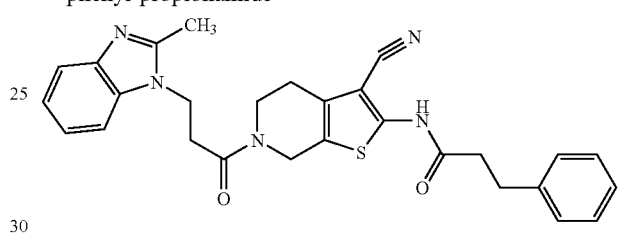

MS: calc.: C, 28; H, 27; N, 5; O, 2; S, (497.62). fnd.: 498.2 [M+H].

22. (RS)-N-[3-Cyano-6-(2-pyridin-2-yl-ethanoyl)-4,5,6,7-tetrahydro-thieno[2,3-c]pyridin-2-yl]-3-phenyl-butyramide

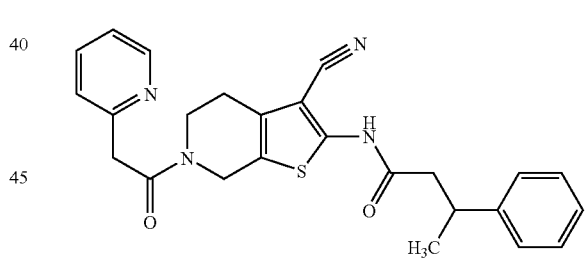

MS: calc.: C, 25; H, 24; N, 4; O, 2; S, (444.56). fnd.: 445.1 [M+H].

23. (RS)-N-[3-Cyano-6-(2-pyridin-3-yl-ethanoyl)-4,5,6,7-tetrahydro-thieno[2,3-c]pyridin-2-yl]-3-phenyl-butyramide

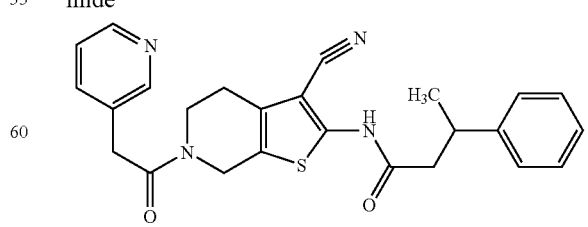

MS: calc.: C, 25; H, 24; N, 4; O, 2; S, (444.56). fnd.: 445.3 [M+H].

24. (RS)-N-[3-Cyano-6-(2-pyridin-4-yl-ethanoyl)-4,5,6,7-tetrahydro-thieno[2,3-c]pyridin-2-yl]-3-phenyl-butyramide

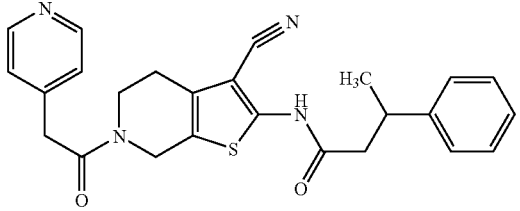

MS: calc.: C, 25; H, 24; N, 4; O, 2; S, (444.56). fnd.: 445.3 [M+H].

25. (RS)-N-[3-Cyano-6-(3-pyridin-3-yl-propanoyl)-4,5,6,7-tetrahydro-thieno[2,3-c]pyridin-2-yl]-3-phenyl-butyramide

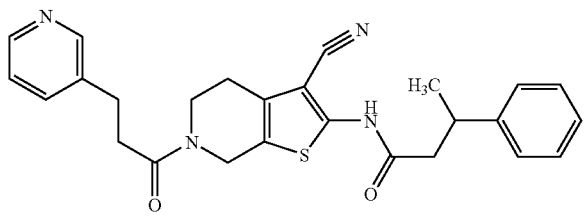

MS: calc.: C, 26; H, 26; N, 4; O, 2; S, (458.59). fnd.: 459.2 [M+H].

26. (RS)-N-[3-Cyano-6-(2-imidazol-1-yl-ethanoyl)-4,5,6,7-tetrahydro-thieno[2,3-]pyridin-2-yl]-3-phenyl-butyramide

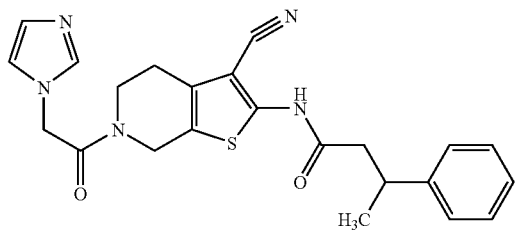

MS: calc.: C, 23; H, 23; N, 5; O, 2; S, (433.54). fnd.: 434.3 [M+H].

27. (RS)-N-(6-Butyryl-3-cyano-4,5,6,7-tetrahydro-thieno[2,3-c]pyridin-2-yl)-3-phenyl-butyramide

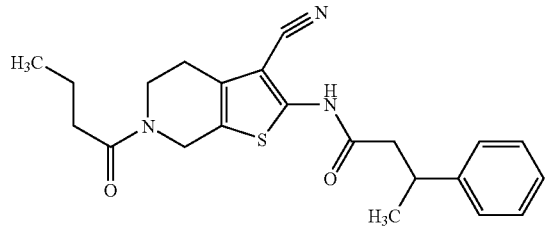

MS: calc.: C, 22; H, 25; N, 3; O, 2; S, (395.53). fnd.: 396.2 [M+H].

28. N-(6-Butyryl-3-cyano-4,5,6,7-tetrahydro-thieno[2,3-c]pyridin-2-yl)-3-phenyl-propionamide

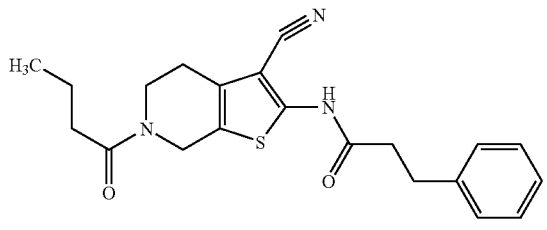

MS: calc.: C, 21; H, 23; N, 3; O, 2; S, (381.5). fnd.: 382.2 [M+H].

29. (RS)-N-[3-Cyano-6-(3-pyridin-2-yl-propanoyl)-4,5,6,7-tetrahydro-thieno[2,3-c]pyridin-2-yl]-3-phenyl-butyramide

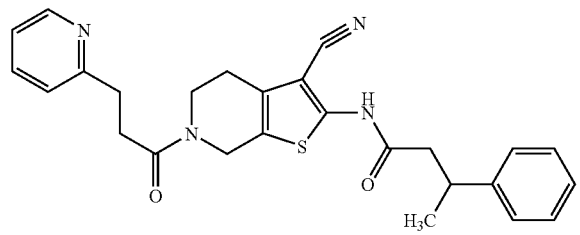

MS: calc.: C, 26; H, 26; N, 4; O, 2; S, (458.59). fnd.: 459.1 [M+H].

30. N-[3-Cyano-6-(3-pyridin-2-yl-propanoyl)-4,5,6,7-tetrahydro-thieno[2,3-c]pyridin-2-yl]-3-phenyl-propionamide

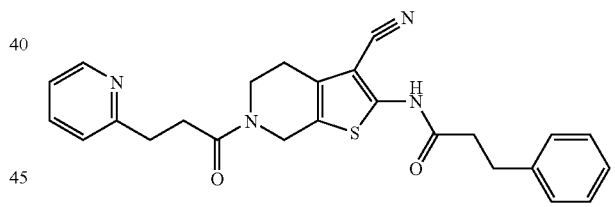

MS: calc.: C, 25; H, 24; N, 4; O, 2; S, (444.56). fnd.: 445.1 [M+H].

31. (RS)-N-[3-Cyano-6-(3-imidazol-1-yl-propanoyl)-4,5,6,7-tetrahydro-thieno[2,3-c]pyridin-2-yl]-3-phenyl-butyramide

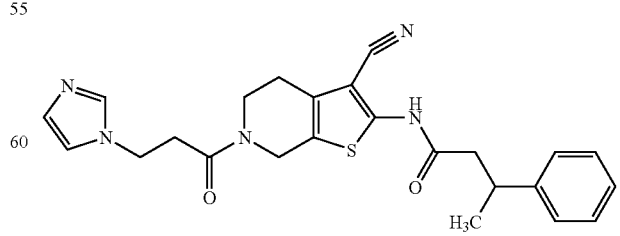

MS: calc.: C, 24; H, 25; N, 5; O, 2; S, (447.56). fnd.: 448.2 [M+H].

32. (RS)-N-{3-Cyano-6-[3-(2-methyl-imidazol-1-yl)-propanoyl]-4,5,6,7-tetrahydro-thieno[2,3-c]pyridin-2-yl}-3-phenyl-butyramide

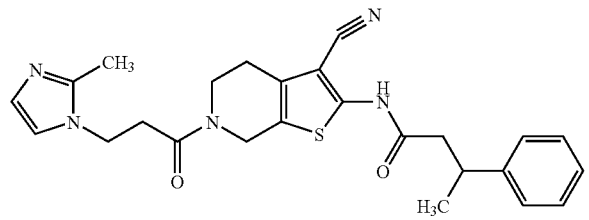

MS: calc.: C, 25; H, 27; N, 5; O, 2; S, (461.59). fnd.: 462.2 [M+H].

33. N-3-Cyano-6-[3-(2-methyl-imidazol-1-yl)-propanoyl]-4,5,6,7-tetrahydro-thieno[2,3-c]pyridin-2-yl)-3-phenyl-propionamide

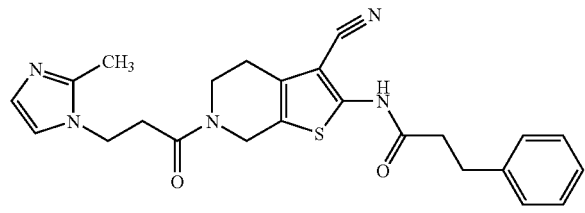

MS: calc.: C, 24; H, 25; N, 5; O, 2; S, (447.56). fnd.: 448.2 [M+H].

34. (RS)-N{3-Cyano-6-[3-(1-methyl-1H-imidazol-2-yl)-propanoyl]-4,5,6,7-tetrahydro-thieno[2,3-c]pyridin-2-yl}-3-phenyl-butyramide

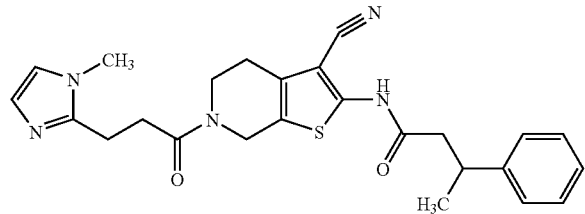

MS: calc.: C, 25; H, 27; N, 5; O, 2; S, (461.59). fnd.: 462.2 [M+H].

35. N-{3-Cyano-6-[3-(1-methyl-1H-imidazol-2-yl)-propanoyl]-4,5,6,7-tetrahydro-thieno[2,3-c]pyridin-2-yl}-3-phenyl-propionamide

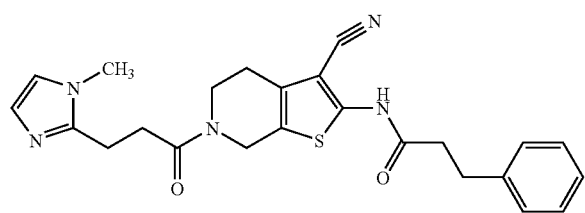

MS: calc.: C, 24; H, 25; N, 5; O, 2; S, (447.56). fnd.: 448.2 [M+H].

36. (RS)-N-[3-Cyano-6-(3-pyridin-4-yl-propanoyl)-4,5,6,7-tetrahydro-thieno[2,3-c]pyridin-2-yl]-3-phenyl-butyramide

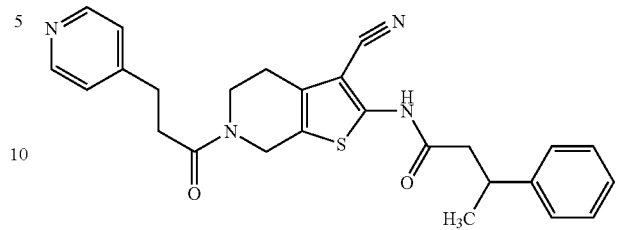

MS: calc.: C, 26; H, 26; N, 4; O, 2; S, (458.59). fnd.: 459.3 [M+H].

37. (RS)-N-{3-Cyano-6-[2-(2-methyl-imidazol-1-yl)-ethanoyl]-4,5,6,7-tetrahydro-thieno[2,3-c]pyridin-2-yl}-3-phenyl-butyramide

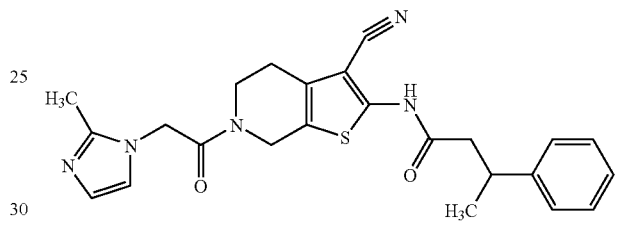

MS: calc.: C, 24; H, 25; N, 5; O, 2; S, (447.56). fnd.: 448.3 [M+H].

38. N-{3-Cyano-6-[2-(2-methyl-imidazol-1-yl)-ethanoyl]-4,5,6,7-tetrahydro-thieno[2,3-c]pyridin-2-yl}-3-phenyl-propionamide

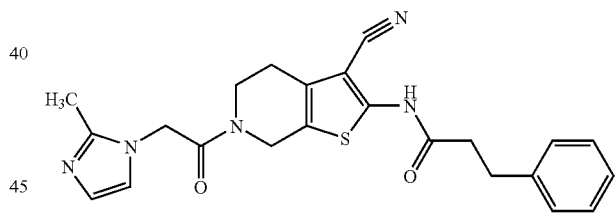

MS: calc.: C, 23; H, 23; N, 5; O, 2; S, (433.54). fnd.: 434.2 [M+H].

39. N-[3-Cyano-6-(3-pyridin-4-yl-propanoyl)-4,5,6,7-tetrahydro-thieno[2,3-c]pyridin-2-yl]-3-phenyl-propionamide

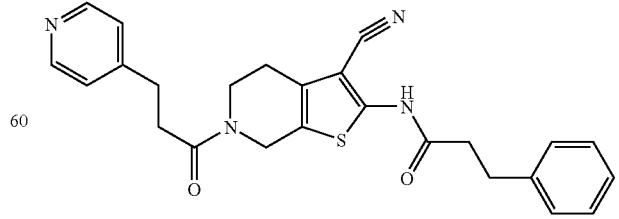

MS: calc.: C, 25; H, 24; N, 4; O, 2; S, (444.56). fnd.: 445.2 [M+H].

40. (RS)-N-{3-Cyano-6-[2-(4-methyl-Imidazol-1-yl)-ethanoyl]-4,5,6,7-tetrahydro-thieno[2,3-c]pyridin-2-yl}-3-phenyl-butyramide

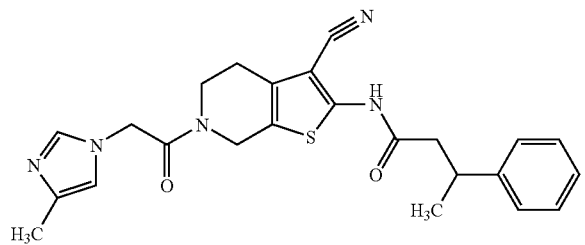

MS: calc.: C, 24; H, 25; N, 5; O, 2; S, (447.56). fnd.: 448.3 [M+H].

41. N-{3-Cyano-4-[2-(4-methyl-imidazol-1-yl)-ethanoyl]-4,5,6,7-tetrahydro-thieno[2,3-c]pyridin-2-yl}-3-phenyl-propionamide

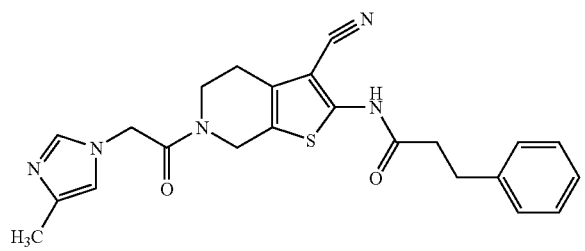

MS: calc.: C, 23; H, 23; N, 5; O, 2; S, (433.54). fnd.: 434.2 [M+H].

42. (RS)-N-{3-Cyano-6-[2-(2,4-dimethyl-imidazol-1-yl)-ethanoyl]-4,5,6,7-tetrahydro-thieno[2,3-c]pyridin-2-yl}-3-phenyl-butyramide

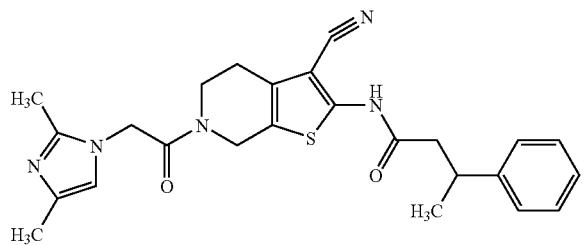

MS: calc.: (C, 25; H, 27; N, 5; O, 2; S, (461,59). fnd.: 462.3 [M+H].

43. N-{3-Cyano-6-[2-(2,4-dimethyl-imidazol-1-yl)-ethanoyl]-4,5,6,7-tetrahydro-thieno[2,3-c]pyridin-2-yl}-3-phenyl-propionamide

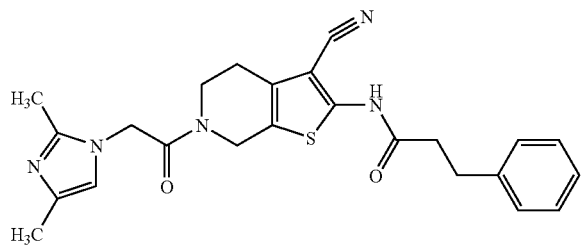

MS: calc.: C, 24; H, 25; N, 5; O, 2; S, (447.56). fnd.: 448.2 [M+H].

44. (RS)-N-(3-Cyano-6-[3-(4-methyl-imidazol-1-yl)-propanoyl]-4,5,6,7-tetrahydro-thieno[2,3-c]pyridin-2-yl)-3-phenyl-butyramide

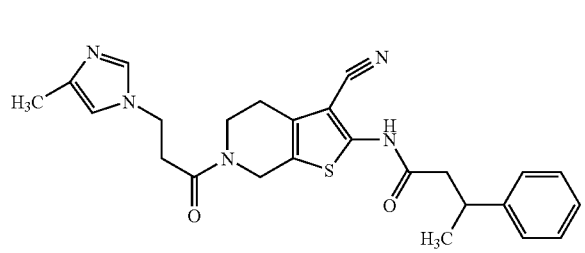

MS: calc.: C, 25; H, 27; N, 5; O, 2; S, (461.59). fnd.: 462.3 [M+H].

45. N-3-Cyano-6-[3-(4-methyl-imidazol-1-yl)-propanoyl]-4,5,6,7-tetrahydro-thieno[2,3-c]pyridin-2-yl)-3-phenyl-propionamide

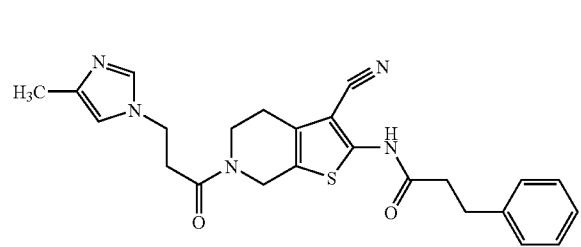

MS: calc.: C, 24; H, 25; N, 5; O, 2; S, (447.56). fnd.: 448.2 [M+H].

46. (RS)-N-{3-Cyano-6-[3-(2,4-dimethyl-imidazol-1-yl)-propanoyl]-4,5,6,7-tetrahydro-thieno[2,3-c]pyridin-2-yl}-3-phenyl-butyramide

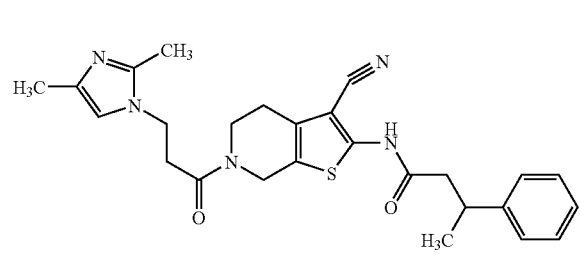

MS: calc.: C, 26; H, 29; N, 5; O, 2; S, (475.62). fnd.: 476.3 [M+H].

47. N-{3-Cyano-6-[3-(2,4-dimethyl-imidazol-1-yl)-propanoyl]-4,5,6,7-tetrahydro-4-thieno[2,3-c]pyridin-2-yl}-3-phenyl-propionamide

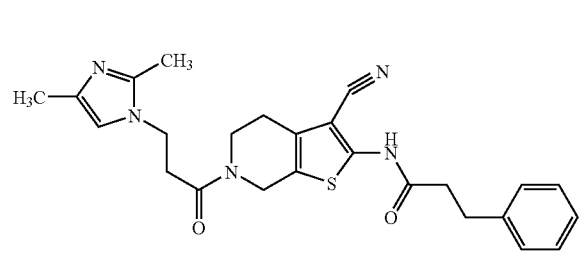

MS: calc.: C, 25; H, 27; N, 5; O, 2; S, (461.59). fnd.: 462.2 [M+H].

48. N-[3-Cyano-6-(3-hydroxy-propanoyl)-4,5,6,7-tetrahydro-thieno[2,3-c]pyridin-2-yl]-3-phenyl-propionamide

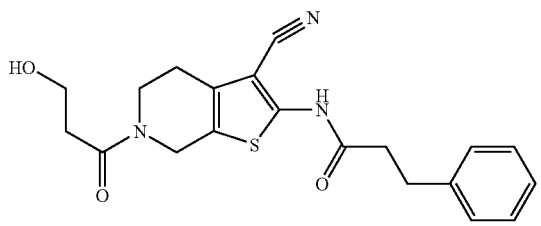

3 eq β-propiolactone and 1 eq of the corresponding amine (compound A1) are dissolved in pyridine and heated for 30 min under microwave assistance at 150° C. Evaporation of the solvent and subsequent preparative reversed phase HPLC affords the desired compound.

MS: calc.: C, 20; H, 21; N, 3; O, 3; S, (383.47). fnd.: 384.0 [M+H].

49. (RS)-N-[3-Cyano-6-(2-hydroxy-ethanoyl)-4,5,6,7-tetrahydro-thieno[2,3-c]pyridin-2-yl]-3-phenyl-butyramide

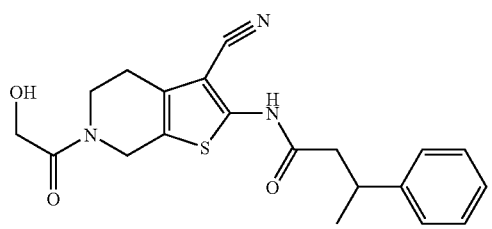

MS: calc.: C, 20; H, 21; N, 3; O, 3; S, (383.47). fnd.: 384.0 [M+H].

50. (RS)-N-[3-Cyano-6-(3-hydroxy-propanoyl)-4,5,6,7-tetrahydro-thieno[2,3-c]pyridin-2-yl]-3-phenyl-butyramide

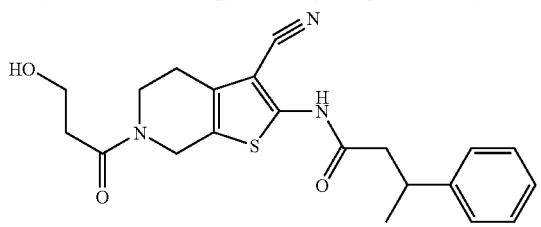

MS: calc.: C, 21; H, 23; N, 3; O, 3; S, (397.50). fnd.: 398.0 [M+H].

51. N-[3-Cyano-6-(2-pyridin-4-yl-ethanoyl)-4,5,6,7-tetrahydro-thieno[2,3-c]pyridin-2-yl]-3-cyclohexyl-propionamide

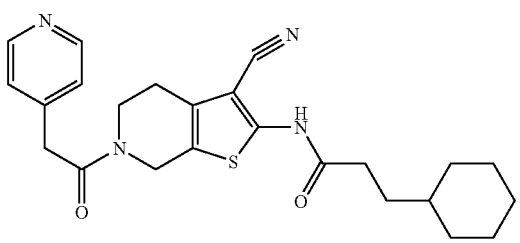

MS: calc.: C, 24; H, 28; N, 4; O, 2; S, (436.58).

52. N-[3-Cyano-6-(2-pyridin-3-yl-ethanoyl)-4,5,6,7-tetrahydro-thieno[2,3-c]pyridin-2-yl]-3-cyclohexyl-propionamide

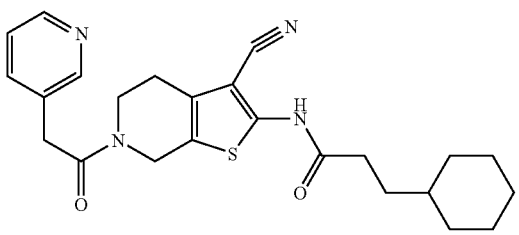

MS: calc.: C, 24; H, 28; N, 4; O, 2; S, (436.58).

53. N-[3-Cyano-6-(2-pyridin-2-yl-ethanoyl)-4,5,6,7-tetrahydro-thieno[2,3-c]pyridin-2-yl]-3-cyclohexyl-propionamide

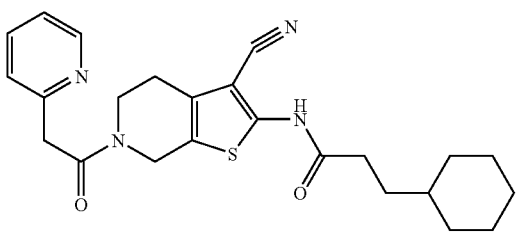

MS: calc.: C, 24; H, 28; N, 4; O, 2; S, (436.58). fnd.: 437.2 [M+H].

54. N-[3-Cyano-6-(3-pyridin-4-yl-propanoyl)-4,5,6,7-tetrahydro-thieno[2,3-c]pyridin-2-yl]-3-cyclohexyl-propionamide

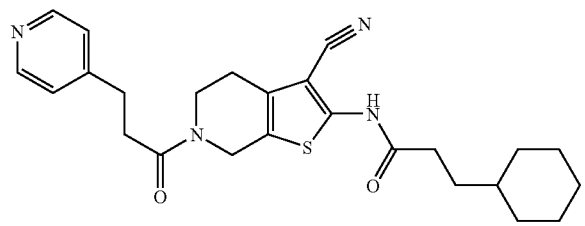

MS: calc.: C, 25; H, 30; N, 4; O, 2; S, (450.61).

55. N-[3-Cyano-6-(3-pyridin-3-yl-propanoyl)-4,5,6,7-tetrahydro-thieno[2,3-c]pyridin-2-yl]-3-cyclohexyl-propionamide

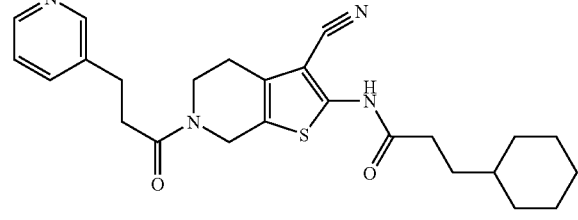

MS: calc.: C, 25; H, 30; N, 4; O, 2; S, (450.61). fnd.: 451.3 [M+H].

56. N-[3-Cyano-6-(3-pyridin-2-yl-propanoyl)-4,5,6,7-tetrahydro-thieno[2,3-c]pyridin-2-yl]-3-cyclohexyl-propionamide

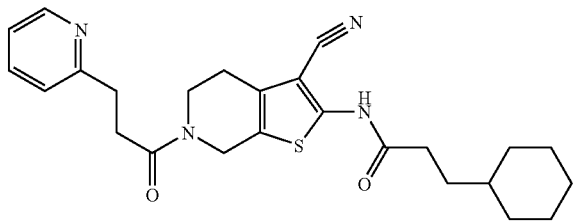

MS: calc.: C, 25; H, 30; N, 4; O, 2; S, (450.61).

57. N-[3-Cyano-6-(2-imidazol-1-yl-ethanoyl)-4,5,6,7-tetrahydro-thieno[2,3-c]pyridin-2-yl]-3-cyclohexyl-propionamide

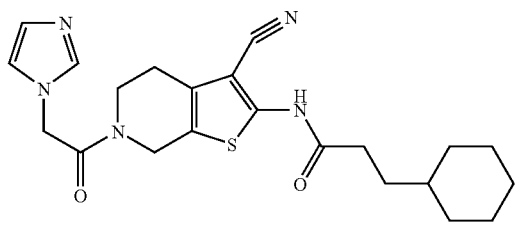

MS: calc.: C, 22; H, 27; N, 5; O, 2; S, (425.56).

58. N-[3-Cyano-6-(3-imidazol-1-yl-propanoyl)-4,5,6,7-tetrahydro-thieno[2,3-]pyridin-2-y]-3-cyclohexyl-propionamide

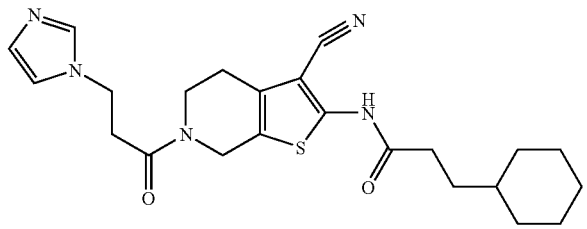

MS: calc.: C, 23; H, 29; N, 5; O, 2; S, (439.58). fnd.: 440.2 [M+H].

59. N-{3-Cyano-6-[3-(1-methyl-1H-imidazol-2-yl)-propanoyl]-4,5,6,7-tetrahydro-thieno[2,3-c]pyridin-2-yl}-3-cyclohexyl-propionamide

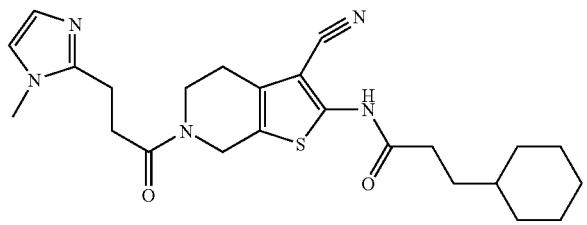

MS: calc.: C, 24; H, 31; N, 5; O, 2; S, (453.61).

60. N-[3-Cyano-6-(3-hydroxy-propanoyl)-4,5,6,7-tetrahydro-thieno[2,3-c]pyridin-2-yl]-3-cyclohexyl-propionamide

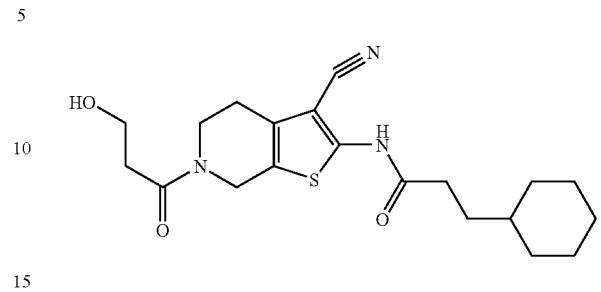

MS: calc.: C, 20; H, 27; N, 3; O, 3; S, (389.52).

61. N-[3-Cyano-6-(2-hydroxy-ethanoyl)-4,5,6,7-tetrahydrothieno[2,3-c]pyridin-2-yl]-3-cyclohexyl-propionamide

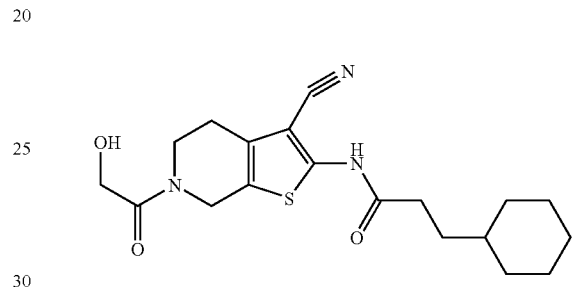

MS: calc.: C, 19; H, 25; N, 3; O, 3; S, (375.49).

62. N-[3-Cyano-6-(2-pyridin-4-yl-ethanoyl)-4,5,6,7-tetrahydro-thieno[2,3-c]pyridin-2-yl]-3-furan-2-yl-propionamide

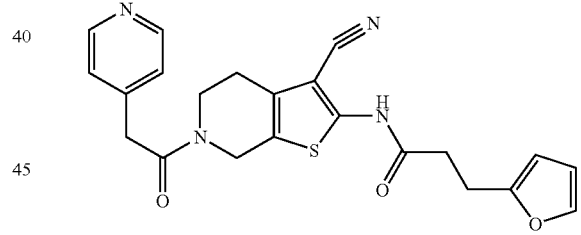

MS: calc.: C, 22; H, 20; N, 4; O, 3; S, (420.49).

63. N-[3-Cyano-6-(3-pyridin-4-yl-propanoyl)-4,5,6,7-tetrahydro-thieno[2,3-c]pyridin-2-yl]-3-furan-2-yl-propionamide

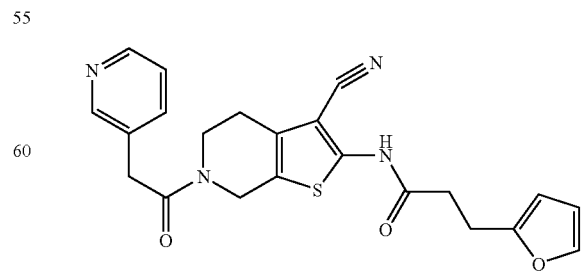

MS: calc.: C, 23; H, 22; N, 4; O, 3; S, (434.52).

64. N-[3-Cyano-6-(3-pyridin-2-yl-propanoyl)-4,5,6,7-tetrahydro-thieno[2,3-c]pyridin-2-yl]-3-furan-2-yl-propionamide

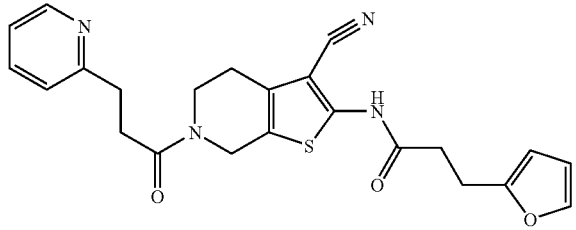

MS: calc.: C, 23; H, 22; N, 4; O, 3; S, (434.52).

65. N-[3-Cyano-6-(2-imidazol-1-yl-ethanoyl)-4,5,6,7-tetrahydro-thieno[2,3-c]pyridin-2-yl]-3-furan-2-yl-propionamide

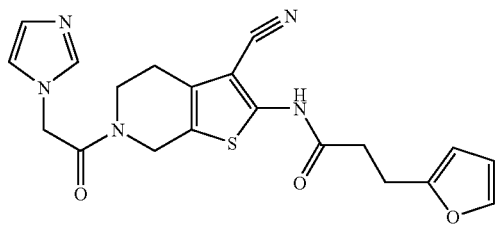

MS: calc.: C, 20; H, 19; N, 5; O, 3; S, (409.47).

66. N-{3-Cyano-6-[3-(1-methyl-1H-imidazol-2-yl)-propanoyl]-4,5,6,7-tetrahydro-thieno[2,3-c]pyridin-2-yl}-3-furan-2-yl-propionamide

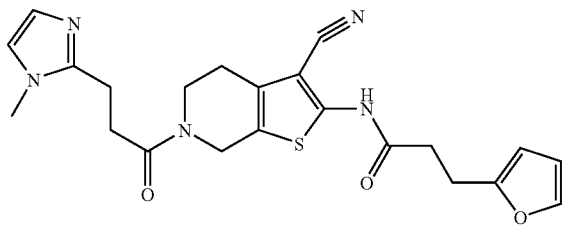

MS: calc.: C, 22; H, 23; N, 5; O, 3; S, (437.52).

67. N-[3-Cyano-6-(3-hydroxy-propanoyl)-4,5,6,7-tetrahydro-thieno[2,3-c]pyridin-2-yl]-3-furan-2-yl-propionamide

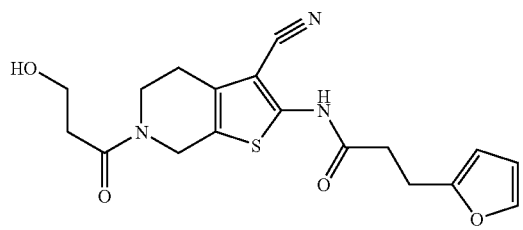

MS: calc.: C, 18; H, 19; N, 3; O, 4; S, (373.43).

68. N-[3-Cyano-6-(2-hydroxy-ethanoyl)-4,5,6,7-tetrahydro-thieno[2,3-c]pyridin-2-yl]-3-furan-2-yl-propionamide

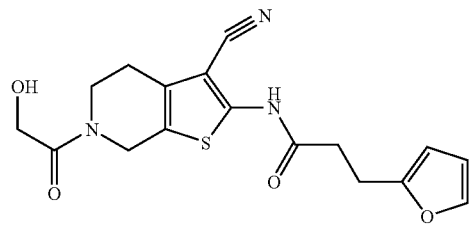

MS: calc.: C, 17; H, 17; N, 3; O, 4; S, (359.41).

69. N-[3-Cyano-6-(2-hydroxy-ethanoyl)-4,5,6,7-tetrahydro-thieno[2,3-c]pyridin-2-yl]-3-pyridin-3-yl-propionamide

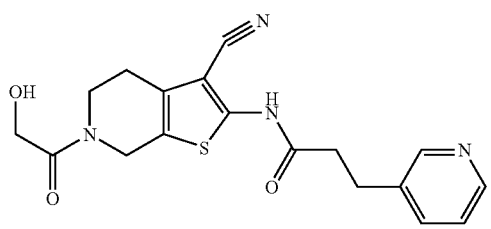

MS: calc.: C, 18; H, 18; N, 4; O, 3; S, (370.43).

70. N-[3-Cyano-6-(3-hydroxy-propanoyl)-4,5,6,7-tetrahydro-thieno[2,3-c]pyridin-2-yl]-3-pyridin-3-yl-propionamide

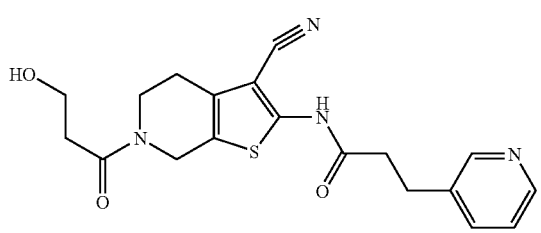

MS: calc.: C, 19; H, 20; N, 4; O, 3; S, (384.46).

71. N-[3-Cyano-6-(2-hydroxy-ethanoyl)-4,5,6,7-tetrahydro-thieno[2,3-c]pyridin-2-yl]-3-pyridin-2-yl-propionamide

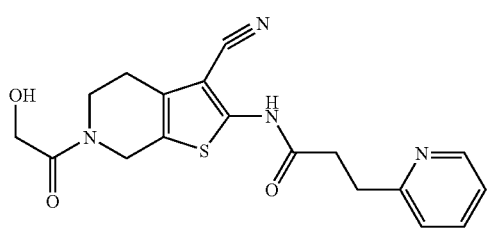

MS: calc.: C, 18; H, 18; N, 4; O, 3; S, (370.43).

72. N-[3-Cyano-6-(3-hydroxy-propanoyl)-4,5,6,7-tetrahydro-thieno[2,3-c]pyridin-2-yl]-3-pyridin-2-yl-propionamide

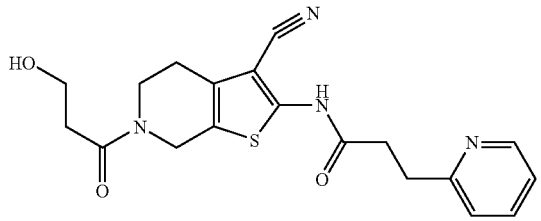

MS: calc.: C, 19; H, 20; N, 4; O, 3; S, (384.46).

73. (1RS,2RS)-2-Phenyl-cyclopropanecarboxylic acid [3-cyano-6-(2-pyridin yl-ethanoyl)-4,5,6,7-tetrahydro-thieno[2,3-c]pyridin-2-yl]-amide

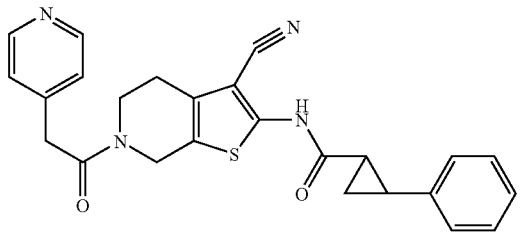

MS: calc.: C, 25; H, 22; N, 4; O, 2; S, (442.54).

74. (1RS,2RS)-2-Phenyl-cyclopropanecarboxylic acid [3-cyano-6-(2-pyridin-3-yl-ethanoyl)-4,5,6,7-tetrahydro-thieno[2,3-c]pyridin-2-yl]-amide

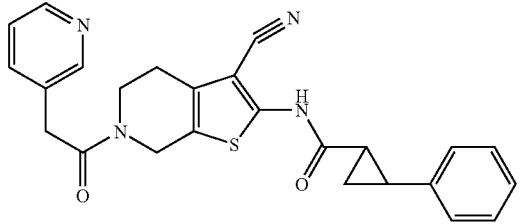

MS: calc.: C, 25; H, 22; N, 4; O, 2; S, (442.54).

75. (1RS,2RS)-2-Phenyl-cyclopropanecarboxylic acid [3-cyano-6-(2-pyridinyl-ethanoyl)-4,5,6,7-tetrahydro-thieno[2,3-c]pyridin-2-yl]-amide

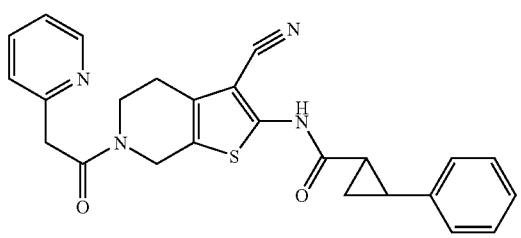

MS: calc.: C, 25; H, 22; N, 4; O, 2; S, (442.54).

76. (1RS,2RS)-2-Phenyl-cyclopropanecarboxylic acid [3-cyano-6-(3-pyridinyl-propanoyl)-4,5,6,7-tetrahydro-thieno[2,3-c]pyridin-2-yl]-amide

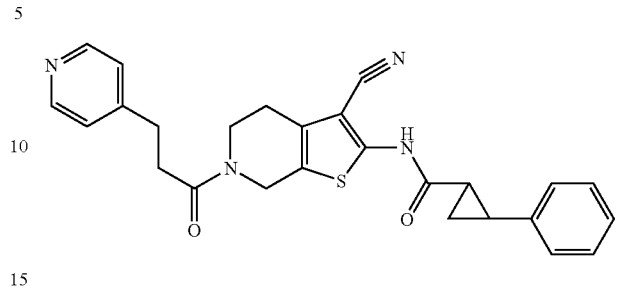

MS: calc.: C, 26; H, 24; N, 4; O, 2; S, (456.57).

77. (1RS,2RS)-2-Phenyl-cyclopropanecarboxylic acid [3-cyano-6-(3-pyridin-3-yl-propanoyl)-4,5,6,7-tetrahydro-thieno[2,3-c]pyridin-2-yl]-amide

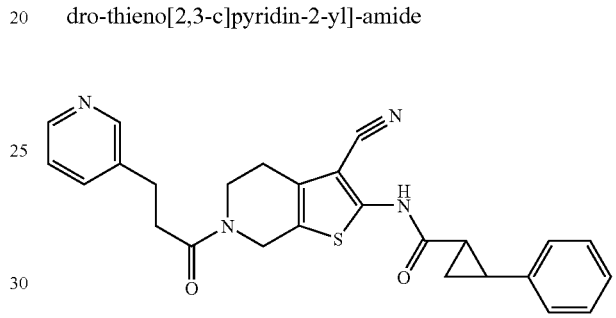

MS: calc.: C, 26; H, 24; N, 4; O, 2; S, (456.57).

78. (1RS,2RS)-2-Phenyl-cyclopropanecarboxylic acid [3-cyano-6-(3-pyridin-2-yl-propanoyl)-4,5,6,7-tetrahydro-thieno[2,3-c]pyridin-2-yl]-amide

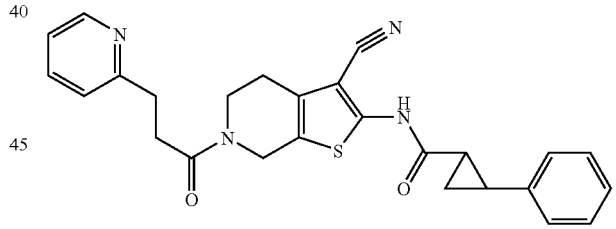

MS: calc.: C, 26; H, 24; N, 4; O, 2; S, (456.57).

79. (1RS,2RS)-2-Phenyl-cyclopropanecarboxylic acid [3-cyano-6-(2-imidazol-1-yl-ethanoyl)-4,5,6,7-tetrahydro-thieno[2,3-c]pyridin-2-yl]-amide

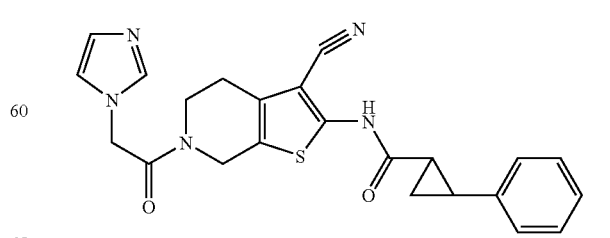

MS: calc.: C, 23; H, 21; N, 5; O, 2; S, (431.52).

80. (1RS,2RS)-2-Phenyl-cyclopropanecarboxylic acid [3-cyano-6-(3-imidazol-1-yl-propanoyl)-4,5,6,7-tetrahydro-thieno[2,3-c]pyridin-2-yl]-amide

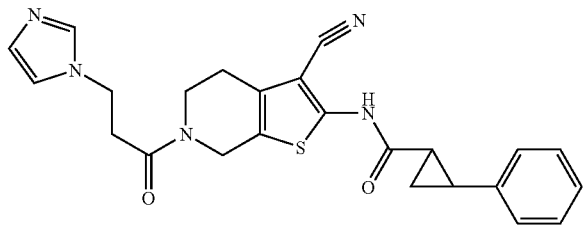

MS: calc.: C, 24; H, 23; N, 5; O, 2; S, (445.55).

81. (1RS,2RS)-2-Phenyl-cyclopropanecarboxylic acid {3-cyano-6-[3-(1-methyl-1H-imidazol-2-yl)-propanoyl]-4,5,6,7-tetrahydro-thieno[2,3-c]pyridin-2-yl}-amide

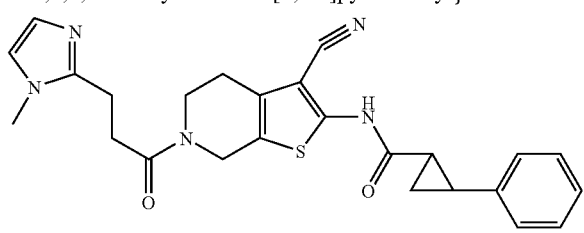

MS: calc.: C, 25; H, 25; N, 5; O, 2; S, (459.57).

82. (1RS,2RS)-2-Phenyl-cyclopropanecarboxylic acid [3-cyano-6-(3-hydroxy-propanoyl)-4,5,6,7-tetrahydro-thieno[2,3-c]pyridin-2-yl]-amide

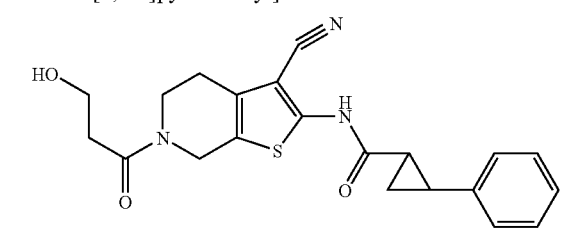

MS: calc.: C, 21; H, 21; N, 3; O, 3; S, (395.48).

83. (1RS,2RS)-2-Phenyl-cyclopropanecarboxylic acid [3-cyano-6-(2-hydroxy-ethanoyl)-4,5,6,7-tetrahydro-thieno[2,3-c]pyridin-2-yl]-amide

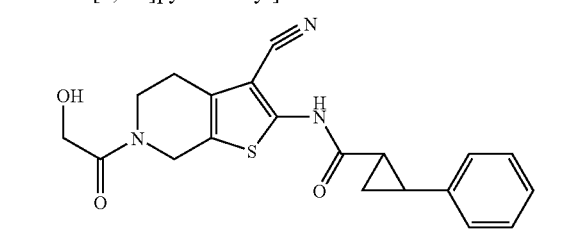

MS: calc.: C, 20; H, 19; N, 3; O, 3; S, (381.46).

The following salts are prepared according to general procedure E:

N-[3-cyano-6-(3-pyridin-3-yl-propanoyl)-4,5,6,7-tetrahydro-thieno[2,3-c]pyridin-2-yl]-3-phenyl-propionamide malonate, m.p.: 250° C.;

N-[3-cyano-6-(3-pyridin-3-yl-propanoyl)-4,5,6,7-tetrahydro-thieno[2,3-c]pyridin-2-yl]-3-phenyl-propionamide L-tartrate, m.p.: 252° C.;

N-[3-cyano-6-(3-pyridin-3-yl-propanoyl)-4,5,6,7-tetrahydro-thieno[2,3-c]pyridin-2-yl]-3-phenyl-propionamide maleate, m.p.: 240° C.;

N-[3-cyano-6-(3-pyridin-3-yl-propanoyl)-4,5,6,7-tetrahydro-thieno[2,3-c]pyridin-2-yl]-3-phenyl-propionamide mesylate, m.p.: 165° C.;

N-[3-cyano-6-(3-pyridin-3-yl-propanoyl)-4,5,6,7-tetrahydro-thieno[2,3-c]pyridin-2-yl]-3-phenyl-propionamide oxalate, m.p.: 236° C.

Starting Materials:

A1. N-(3-Cyano-4,5,6,7-tetrahydro-thieno[2,3c]pyridin-2-yl)-3-phenyl-propionamide

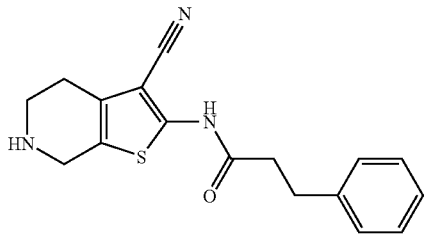

The title compound is prepared according to general procedure B starting from 3-cyano-2-(3-phenyl-propanoylamino)-4,7-dihydro-5H-thieno[2,3-c]pyridine-6-carboxylic acid tert-butyl ester (compound B1).

Using similar procedures as described to attain compound A1 or A20, but with suitable choice of starting materials, the following compounds may be prepared:

A2. N-(3-Cyano-4,5,6,7-tetrahydro-thieno[2,3-c]pyridin-2-yl)-3-(2-chlorophenyl)-propionamide A3. N-(3-Cyano-4,5,6,7-tetrahydro-thieno[2,3-c]pyridin-2-yl)-3-(2-methylphenyl)-propionamide A4. N-(3-Cyano-4,5,6,7-tetrahydro-thieno[2,3-c]pyridin-2-yl)-3-(2,3-dimethyl-phenyl)-propionamide A5. N-(3-Cyano-4,5,6,7-tetrahydro-thieno[2,3-c]pyridin-2-yl)-3-(2,3-dimethyl-phenyl)-propionamide A6. N-(3-Cyano-4,5,6,7-tetrahydro-thieno[2,3-c]pyridin-2-yl)-3-(2-chloro-3-methyl-phenyl)-propionamide A7. N-(3-Cyano-4,5,6,7-tetrahydro-thieno[2,3-c]pyridin-2-yl)-3-(2-chloro-5-methyl-phenyl)-propionamide A8. N-(3-Cyano-4,5,6,7-tetrahydro-thieno[2,3-c]pyridin-2-yl)-3-(2-fluorophenyl)-propionamide A9. N-(3-Cyano-4,5,6,7-tetrahydro-thieno[2,3-c]pyridin-2-yl)-3-(2-ethylphenyl)-propionamide A10. N-(3-Cyano-4,5,6,7-tetrahydro-thieno[2,3-c]pyridin-2-yl)-3-(3-chlorophenyl)-propionamide A11. N-(3-Cyano-4,5,6,7-tetrahydro-thieno[2,3-c]pyridin-2-yl)-3-(3-methylphenyl)-propionamide A12. N-(3-Cyano-4,5,6,7-tetrahydro-thieno[2,3-c]pyridin-2-yl)-3-(3-fluorophenyl)-propionamide A13. N-(3-Cyano-4,5,6,7-tetrahydro-thieno[2,3-c]pyridin-2-yl)-3-(3-ethylphenyl)-propionamide A14. N-(3-Cyano-4,5,6,7-tetrahydro-thieno[2,3-c]pyridin-2-yl)-3-(pyridin-2-yl)-propionamide A15. N-(3-Cyano-4,5,6,7-tetrahydro-thieno[2,3-c]pyridin-2-yl)-3-(pyridin-3-yl)-propionamide A16. N-(3-Cyano-4,5,6,7-tetrahydro-thieno[2,3-c]pyridin-2-yl)-3-(pyridin-4-yl)-propionamide A17. N-(3-Cyano-4,5,6,7-tetrahydro-thieno[2,3-c]pyridin-2-yl)-3-(thiophen-3-yl)-propionamide A18. N-(3-Cyano-4,5,6,7-tetrahydro-thieno[2,3-c]pyridin-2-yl)-3-(thiophen-2-yl)-propionamide A19. N-(3-Cyano-4,5,6,7-tetrahydro-thieno[2,3-c]pyridin-2-yl)-3-(furan-3-yl)-propionamide A20. N-(3-Cyano-4,5,6,7-tetrahydro-thieno[2,3-c]pyridin-2-yl)-3-(furan-2-yl)-propionamide 200 mg of 3-cyano-2-(3-furan-2-yl-propanoylamino)-4,7-dihydro-5H-thieno[2,3-c]pyridine-6-carboxylic acid tert-butyl ester are dissolved in 7 ml of a mixture of dichloromethane and TFA and stirred at room temperature for 3 h. Evaporation of the solvent gives 250 mg of the desired product as TFA salt in sufficient purity for the next steps.

Using similar procedures as described to attain compound A1 or A20, but with suitable choice of starting materials, the following compounds may be prepared:

A21. (RS)-N-(3-Cyano-4,5,6,7-tetrahydro-thieno[2,3-c]pyridin-2-yl)-3-phenyl-butyramide A22. (RS)-N-(3-Cyano-4,5,6,7-tetrahydro-thieno[2,3-c]pyridin-2-yl)-3-(2-chlorophenyl)-butyramide A23. (RS)-N-(3-Cyano-4,5,6,7-tetrahydro-thieno[2,3-c]pyridin-2-yl)-3-(2-methylphenyl)-butyramide A24. (RS)-N-(3-Cyano-4,5,6,7-tetrahydro-thieno[2,3-c]pyridin-2-yl)-3-(2,3-dimethyl-phenyl)-butyramide A25. (RS)-N-(3-Cyano-4,5,6,7-tetrahydro-thieno[2,3-c]pyridin-2-yl)-3-(2,5-dimethyl-phenyl)-butyramide A26. (RS)-N-(3-Cyano-4,5,6,7-tetrahydro-thieno[2,3-c]pyridin-2-yl)-3-(2-chloro-3-methyl-phenyl)-butyramide A27. (RS)-N-(3-Cyano-4,5,6,7-tetrahydro-thieno[2,3-c]pyridin-2-yl)-3-(2-chloro-5-methyl-phenyl)-butyramide A28. (RS)-N-(3-Cyano-4,5,6,7-tetrahydro-thieno[2,3-c]pyridin-2-yl)-3-(2-fluorophenyl)-butyramide A29. (RS)-N-(3-Cyano-4,5,6,7-tetrahydro-thieno[2,3-c]pyridin-2-yl)-3-(2-ethylphenyl)-butyramide A30. (RS)-N-(3-Cyano-4,5,6,7-tetrahydro-thieno[2,3-c]pyridin-2-yl)-3-(3-chlorophenyl)-butyramide A31. (RS)-N-(3-Cyano-4,5,6,7-tetrahydro-thieno[2,3-c]pyridin-2-yl)-3-(3-methylphenyl)-butyramide A32. (RS)-N-(3-Cyano-4,5,6,7-tetrahydro-thieno[2,3-c]pyridin-2-yl)-3-(3-fluorophenyl)-butyramide A33. (RS)-N-(3-Cyano-4,5,6,7-tetrahydro-thieno[2,3-c]pyridin-2-yl)-3-(3-ethylphenyl)-butyramide A34. (RS)-N-(3-Cyano-4,5,6,7-tetrahydro-thieno[2,3-c]pyridin-2-yl)-3-(pyridin-2-yl)-butyramide A35. (RS)-N-(3-Cyano-4,5,6,7-tetrahydro-thieno[2,3-c]pyridin-2-yl)-3-(pyridin-3-yl)-butyramide A36. (RS)-N-(3-Cyano-4,5,6,7-tetrahydro-thieno[2,3-c]pyridin-2-yl)-3-(pyridin-4-yl)-butyramide A37. (RS)-N-(3-Cyano-4,5,6,7-tetrahydro-thieno[2,3-c]pyridin-2-yl)-3-(thiophen-3-yl)-butyramide A38. (RS)-N-(3-Cyano-4,5,6,7-tetrahydro-thieno[2,3-c]pyridin-2-yl)-3-(thiophen-2-yl)-butyramide A39. (RS)-N-(3-Cyano-4,5,6,7-tetrahydro-thieno[2,3-c]pyridin-2-yl)-3-(furan-3-yl)-butyramide A40. (RS)-N-(3-Cyano-4,5,6,7-tetrahydro-thieno[2,3-c]pyridin-2-yl)-3-(furan-2-yl)-butyramide A41. N-(3-Cyano-4,5,6,7-tetrahydro-thieno[2,3-c]pyridin-2-yl)-3-cyclohexyl)-propionamide A42. (RS)-N-(3-Cyano-4,5,6,7-tetrahydro-thieno[2,3-c]pyridin-2-yl)-3-cyclohexyl-butyramide A43. (1RS,2RS)-2-Phenyl-cyclopropanecarboxylic acid (3-cyano-4,5,6,7-tetrahydro-thieno[2,3-c]pyridin-2-yl)-amide A44. (1RS,2RS)-2-(2-Chlorophenyl)-cyclopropanecarboxylic acid (3-cyano-4,5,6,7-tetrahydro-thieno[2,3-c]pyridin-2-yl)-amide A45. (1RS,2RS)-2-(2-Methylphenyl)-cyclopropanecarboxylic acid (3-cyano-4,5,6,7-tetrahydro-thieno[2,3-c]pyridin-2-yl)-amide A46. (1RS,2RS)-2-(2,3-Dimethylphenyl)-cyclopropanecarboxylic acid (3-cyano-4,5,6,7-tetrahydro-thieno[2,3-c]pyridin-2-yl)-amide A47. (1RS,2RS)-2-(2,5-Dimethylphenyl)-cyclopropanecarboxylic acid (3-cyano-4,5,6,7-tetrahydro-thieno[2,3-c]pyridin-2-yl)-amide A48. (1RS,2RS)-2-(2-Chloro-3-methyl-phenyl)-cyclopropanecarboxylic acid (3-cyano-4,5,6,7-tetrahydro-thieno[2,3-c]pyridin-2-yl)-amide A49. (1RS,2RS)-2-(2-Chloro-5-methyl-phenyl)-cyclopropanecarboxylic acid (3-cyano-4,5,6,7-tetrahydro-thieno[2,3-c]pyridin-2-yl)-amide A50. (1RS,2RS)-2-(2-Fluorophenyl)-cyclopropanecarboxylic acid (3-cyano-4,5,6,7-tetrahydro-thieno[2,3-c]pyridin-2-yl)-amide A51. (1RS,2RS)-2-(2-Ethylphenyl)-cyclopropanecarboxylic acid (3-cyano-4,5,6,7-tetrahydro-thieno[2,3-c]pyridin-2-yl)-amide A52. (1RS,2RS)-2-(3-Chlorophenyl)-cyclopropanecarboxylic acid (3-cyano-4,5,6,7-tetrahydro-thieno[2,3-c]pyridin-2-yl)-amide A53. (1RS,2RS)-2-(3-Methylphenyl)-cyclopropanecarboxylic acid (3-cyano-4,5,6,7-tetrahydro-thieno[2,3-c]pyridin-2-yl)-amide A54. (1RS,2RS)-2-(3-Fluorophenyl)-cyclopropanecarboxylic acid (3-cyano-4,5,6,7-tetrahydro-thieno[2,3-c]pyridin-2-yl)-amide A55. (1RS,2RS)-2-(3-Ethylphenyl)-cyclopropanecarboxylic acid (3-cyano-4,5,6,7-tetrahydro-4-thieno[2,3-c]pyridin-2-yl)-amide A56. (1RS,2RS)-2-(Pyridin-2-yl)-cyclopropanecarboxylic acid (3-cyano-4,5,6,7-tetrahydro-thieno[2,3-c]pyridin-2-yl)-amide A57. (1RS,2RS)-2-(Pyridin-3-yl)-cyclopropanecarboxylic acid (3-cyano-4,5,6,7-tetrahydro-thieno[2,3-c]pyridin-2-yl)-amide A58. (1RS,2RS)-2-(Pyridin-4-yl)-cyclopropanecarboxylic acid (3-cyano-4,5,6,7-tetrahydro-thieno[2,3-c]pyridin-2-yl)-amide A59. (1RS,2RS)-2-(Thiophen-2-yl)-cyclopropanecarboxylic acid (3-cyano-4,5,6,7-tetrahydro-thieno[2,3-c]pyridin-2-yl)-amide A60. (1RS,2RS)-2-(Thiophen-3-yl)-cyclopropanecarboxylic acid (3-cyano-4,5,6,7-tetrahydro-thieno[2,3-c]pyridin-2-yl)-amide A61. (1RS,2RS)-2-(Furan-2-yl)-cyclopropanecarboxylic acid (3-cyano-4,5,6,7-tetrahydro-thieno[2,3-c]pyridin-2-yl)-amide A62. (1RS,2RS)-2-(Furan-3-yl)-cyclopropanecarboxylic acid (3-cyano-4,5,6,7-tetrahydro-4-thieno[2,3-c]pyridin-2-yl)-amide A63. (1RS,2RS)-2-Cyclohexyl-cyclopropanecarboxylic acid (3-cyano-4,5,6,7-tetrahydro-thieno[2,3-c]pyridin-2-yl)-amide

B1. 3-Cyano-2-(3-phenyl-propanoylamino) 4,7-dihydro-5H-thieno[2,3-c]pyridine-4-6-carboxylic acid tert-butyl ester

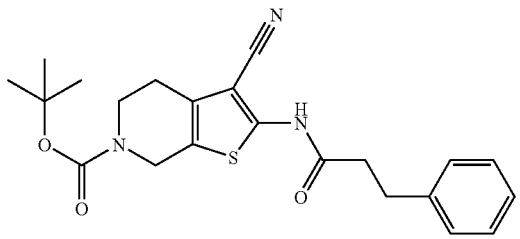

The title compound is prepared according to general procedure A d) starting from 2-amino-3-cyano-4,7-dihydro-5H-thieno[2,3-c]pyridine-6-carboxylic acid tert-butyl ester (compound C1) and hydrocinnamic acid. Using the appropriate carboxylic acids, further relevant starting compounds can be prepared similarly.

MS: calc.: C, 22; H, 25; N, 3; O, 3; S, (411.53). fnd.: 412.1 [M+H].

B2. 3-Cyano-2-(3-pyridin-3-yl-propanoylamino)-4,7-dihydro-5H-thieno[2,3-c]pyridine-carboxylic acid tert-butyl ester

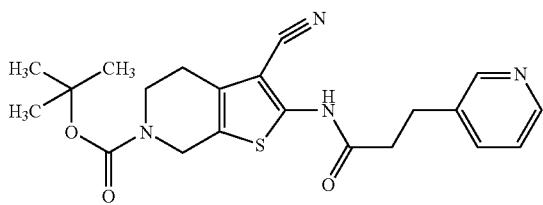

The title compound can be prepared similarly to compound B1 using the appropriate propionic acid.

MS: calc.: C, 21; H, 24; N, 4; O, 3; S, (412.51). fnd.: 413.0 [M+H].

B3. 3-Cyano-2-(3-furan-2-yl-propanoylamino)-4,7-dihydro-5H-thieno[2,3-c]pyridine-carboxylic acid tert-butyl ester 7 g of 3-(2-Furyl) propionic acid are dissolved in dichloromethane and 5.8 g of carbonyldiimidazole (CDI) are slowly added. After the gas evolution terminated 4 g of 2-amino-3-cyano-4,7-dihydro-5H-thieno[2,3-c]pyridine-6-carboxylic acid tert-butyl ester and 10 ml of triethylamine are added and the reaction mixture is heated at 75° C. for 3,5 hours in the microwave. Flash chromatography (dichloromethane) affords the target compound in 85% yield.

C1. 2-Amino-3-cyano-4,7-dihydro-5H-thieno[2,3-c]pyridine-4-carboxylic acid tert-butyl ester

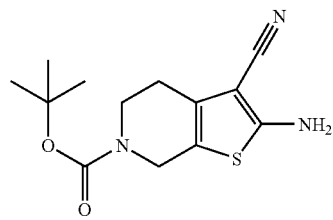

The title compound can be prepared according to general procedure C starting from 4-oxo-piperidine-1-carboxylic acid tert-butylester (Boc-4-piperidone) as cyclic ketone.

MS: calc.: C, 13; H, 17; N, 3; O, 2; S, (279.36). fnd.: 280.0 [M+H].

General Procedures

A'. Further General Procedure for Amide Bond Formation 1.5 eq of the appropriate carboxylic acid are dissolved in a small amount of DMF and 1.3 eq CDI are added. After decease of the gas evolution (~1 h) 1 eq of the appropriate amino building block and 5 eq triethyl amine are added and the reaction mixture stirred for several hours at room temperature.

For workup the following options are used:

In case the product precipitates from the reaction mixture it is filtered off and triturated from ethanol. If the product does not precipitate from the reaction mixture, the reaction mixture is concentrated and subjected to chromatography (either preparative reversed phase HPLC or flash chromatography using dichloromethane/methanol mixtures as eluent).

B. General Procedure for Removal of Boc Protecting Groups

The Boc protected compound is dissolved in dichloromethane/trifluoroacetic acid (TFA) (2/3) and stirred for several hours at room temperature. After evaporation of the solvent and recrystallization from an appropriate solvent (e.g. ethanol), the desired product is obtained as TFA salt. The TFA salt may be converted into the free base in a manner customary per se to the skilled person.

C. General Procedure for Condensed 2-Amino-Thiophene-3-Carbonitrile Derivatives 500 mmol of cyclic ketone and 500 mmol of malononitrile are dissolved in a minimal volume of ethanol and 500 mmol elemental sulfur are added. After addition of 500 mmol diethyl amine, the reaction mixture is heated to 60-70° C. for some minutes and then stirred at room temperature for several hours. The reaction mixture is poured on ice/water and the precipitate filtered off. In case there is no or only some precipitate formed, the aqueous layer is extracted several times with dichloromethane or another appropriate organic solvent, the combined organic layers are dried (e.g. $MgSO_4$) and concentrated in vacuo. Purification of the crude product is achieved by flash chromatography and/or recrystallization from an appropriate solvent (e.g. ethanol).

D. General Procedure for the Preparation of Carboxylic Acids

Synthesis of propionic adds starting from aldehyde:

10 mmol of the appropriate aldehyde are dissolved with 1.1 eq. of triethyl phosphonoacetate in 7 ml THF. At 0° C. 1 eq. of DBU is added and the reaction mixture is stirred over night at room temperature. Then, the reaction mixture is diluted with water, acidified with aq. HCl and extracted with diethyl ether. The organic layer is dried over $MgSO_4$ and the solvent removed. This acrylic acid ester is used without further purification. The crude acrylic acid ester is suspended in 20 ml 1N NaOH and stirred over night. After the reaction is completed, the reaction mixture is acidified with 1N HCl and extracted with diethyl ether. The organic layer is dried over $MgSO_4$ and the solvent evaporated; the desired acrylic acid is obtained in almost pure form. 11 mmol of the acrylic acid are dissolved in 20 ml MeOH, 1 eq. of $NAHCO_3$ and 200 mg Pd/C (10%) are added and the reaction hydrogenated over night at room temperature and normal pressure. Filtration of the reaction mixture over Celite and removal of the solvent affords the desired

Synthesis of β-methyl propionic acid starting from acetophenone 1.9 mmol of sodium hydride are suspended in 5 ml toluene and 1.6 mmol triethyl phosphonoacetate are added at 0° C. After stirring for 30 min at 0° C., 1.1 mmol of the appropriate acetophenone is dissolved in 1 ml toluene, added to the reaction mixture and the reaction mixture stirred over night or for several days at room temperature or heated to 60° C. After addition of some water, the reaction mixture is extracted with toluene and the combined organic layers are dried over $MgSO_4$. The crude acrylic acid ester is obtained as cis/trans mixture and used without further purification. The acrylic acid ester is suspended in a mixture of EtOH and 1N NaOH and stirred over night at room temperature. After acidification with 1N HCl the acrylic acid crystallizes and can be obtained by filtration. In case no crystallization can be achieved, the acrylic acid can be purified via flash chromatography. The acrylic acid is hydrogenated in MeOH with Pd/C (10%) and 1 eq. $NaHCO_3$ under normal pressure at room temperature. After filtration over Celite, the solvent is removed and the desired β-methyl propionic acid purified via flash chromatography if necessary.

Cyclopropanation 113 mg of sodium hydride and 1.1 g of trimethyl sulfoxonium iodide are stirred for one hour in 7 ml DMSO at room temperature. 500 mg of trans cinnamic acid ethyl ester are dissolved in 6 ml DMSO/THF (1:1) and added to the reaction mixture. After completion of the reaction (3 h, TLC) 1N HCl is added and the reaction mixture extracted with diethyl ether. The combined organic layers are dried over $MgSO_4$, the solvent removed and the crude product (393 mg) is used without further purification. In case the purity is not sufficient, the product can be purified by flash chromatography. Saponification of the ester to give the corresponding carboxylic acid can be obtained similarly as described in the foregoing procedures. Further relevant starting compounds can be obtained similarly. Thus, e.g. 2-(pyridin-2-yl)-cyclopropanecarboxylic acid, 2-(pyridin-3-yl)-cyclopropanecarboxylic acid and 2-cyclohexyl-cyclopropanecarboxylic acid may be obtained similarly.

3-Pyridin-2-yl-butyric acid

The title compound can be obtained from the corresponding methyl ester, which is described e.g. in Lindstedt E.-L., Nilsson M., Acta Chem. Scand. Ser. B, EN, 40, 6, 1986, 466-469, by standard saponification using e.g. NaOH or LiOH.

3-Pyridin-3-yl-butyric acid

The title compound can be obtained from the corresponding ethyl ester, which is described e.g. in Sainsbury M., Weerasinghe D., Dolman D., J. Chem. Soc. Perkin Trans. 1, EN, 1982, 587-590, by standard saponification using e.g. NaOH or LiOH.

Synthesis of (Di)methyl-substituted imidazol-1-yl-acetic/-propionic acids (2-Methyl-imidazol-1-yl)-acetic acid methyl ester This compound is prepared in analogy to US2005/154024:

4 ml of bromo acetic acid methyl ester is dissolved in 30 ml DMF and 5.2 g of 2-methylimidazole and 11.2 g potassium carbonate are added. The reaction mixture is stirred at room temperature for several hours and then subjected to aqueous work up. After removal of the solvent the pure product is obtained by flash chromatography in 47 to 78% yield.

(4-Methyl-imidazol-1-yl)-acetic acid methyl ester and (2,4-dimethyl-imidazol-1-yl)-acetic acid methyl ester These compounds are prepared in analogy to (2-methyl-imidazol-1-yl)-acetic acid methyl ester and can be obtained as mixture which is used without separation of the components.

(2-Methyl-imidazol-1-yl)-propionic acid ethyl ester 2-methyl-imidazole is solved in DMF and 1 eq $K_2CO_3$ and 1.3 eq acrylic acid ethyl ester added. After stirring the reaction mixture over night at room temperature, the reaction mixture is poured on water and extracted several times with dichloromethane. Removal of the solvent and flash chromatography affords the desired ethyl ester in >80% yield.

(4-Methyl-imidazol-1-yl)-propionic acid ethyl ester and (2,4-dimethyl-imidazol-1-yl)-propionic acid ethyl ester These compounds are prepared in analogy to (2-methyl-imidazol-1-yl)-propionic acid methyl ester and can be obtained as mixture which is used without separation of the components.

All of the aforementioned (di)methyl-substituted imidazol-1-yl-acetic/-propionic acid esters are saponified under standard conditions to obtain the corresponding carboxylic acids.

3-Imidazol-1-yl-propionic acid can be obtained from the corresponding aldehyde similarly as described above.

3-Phenyl-butyric acid and 3-cyclohexyl-butyric acid can be obtained from the corresponding acetophenone similarly as described above.

Imidazol-1-yl-acetic acid, 3-imidazol-1-yl-propionic acid and 3-cyclohexyl-propionic acid are known or can be obtained analogously or similarly to known procedures.

Relevant pyridyl-acetic acids and 3-pyridyl-propionic acids or other relevant acetic or propionic acid derivatives are known or can be obtained analogously or similarly to known procedures.

E. General Procedure for the Preparation of Salts of the Final Compounds 50 mg of the final compound with basic nitrogen is suspended in 1 ml of acetone and a suspension of 1.1 eq of the corresponding acid in 1 ml of acetone is added. Refluxing of the mixture and addition of 0.5 ml of water affords a clear solution from which the salt normally precipitates upon cooling. This salt is collected and recrystallized from ethanol. In case no or only few salt precipitates the mixture is evaporated to dryness and the remaining solid is recrystallized from ethanol.

Commercial Utility

The compounds according to the present invention have miscellaneous valuable pharmacological properties which can make them commercially applicable.

The compounds according to the invention therefore can be employed as therapeutic agents for the treatment and prophylaxis of diseases in human and veterinary medicine.

Thus, for example, in more embodimental detail, the compounds according to this invention are potent and highly efficacious cell-cycle specific inhibitors of cellular (hyper) proliferation and/or inducers of apoptosis in cancer cells. Therefore, these compounds are expected to be useful for treating (hyper)proliferative diseases and/or disorders responsive to the induction of apoptosis, in particular cancer.

Further on, these compounds can be useful in the treatment of benign or malignant neoplasia. A "neoplasia" is defined by cells displaying aberrant cell proliferation and/or survival and/or a block in differentiation. A "benign neoplasia" is described by hyperproliferation of cells, incapable of forming an aggressive, metastasizing tumor in-vivo. In contrast, a "malignant neoplasia" is described by cells with multiple cellular and biochemical abnormalities, capable of forming a systemic disease, for example forming tumor metastasis in distant organs.

Various diseases are caused by limitless replicative potential and aberrant cell proliferation ("hyperproliferation") as well as evasion from apoptosis. These diseases include e.g. benign hypoplasia like that of the prostate ("BPH") or colon epithelium, psoriasias, glomerulonephritis or osteoarthritis. Most importantly these diseases include malignant neoplasia commonly described as cancer and characterized by tumor cells finally metastasizing into distinct organs or tissues. Malignant neoplasia include solid and hematological tumors. Solid tumors are exemplified by tumors of the breast, bladder, bone, brain, central and peripheral nervus system, colon, endocrine glands (eg thyroid and adrenal cortex), esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva. Malignant neoplasia include inherited cancers exemplified by retinoblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

It is to be noted that a cancer disease as well as a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Neoplastic cell proliferation might effect normal cell behaviour and organ function. For example the formation of new blood vessels, a process described as neovascularization, is induced by tumors or tumor metastases. Compounds according to this invention can be commercially applicable for treatment of pathophysiological relevant processes caused by benign or neoplastic cell proliferation, such as but not limited to neovascularization by unphysiological proliferation of vascular endothelial cells.

Drug resistance is of particular importance for the frequent failure of standard cancer therapeutics. This drug resistance is caused by various cellular and molecular mechanisms like overexpression of drug efflux pumps or mutation within the cellular target protein. The commercial applicability of the compounds according to this invention is not limited to $1^{st}$ line treatment of patients. Patients with resistance to defined cancer chemotherapeutics or target specific anti-cancer drugs ($2^{nd}$ or $3^{rd}$ line treatment) can be also amenable for treatment with the compounds according to this invention.

The compounds according to the present invention display a cell cycle dependent cytotoxic activity, more precisely a mitosis confined activity, leading to a mitotic arrest which inevitably results in the onset of apoptosis and/or cell death.

Compounds of the present invention induce a strongly increased phosphorylation of histone H3 when incubated with test cells for more than 8 hours and less than 48 hours at concentrations around the IC50 value of the cytotoxicity or above. Moreover, treatment of cells with compounds of this invention does not induce polyploidy or multinuclearity as primary mode of action.

Compounds according to the present invention can be commercially applicable for treatment, prevention or amelioration of the diseases of benign and malignant behavior as described before, such as e.g. benign or malignant neoplasia, particularly cancer, such as e.g. any of those cancer diseases described above.

In the context of their properties, functions and usabilities mentioned herein, the compounds according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability (e.g. solubility behaviour).

The invention further includes a method for treating (hyper)proliferative diseases and/or disorders responsive to the induction of apoptosis, particularly those diseases, disorders, conditions or illnesses mentioned above, in mammals, including humans, suffering therefrom comprising administering to said mammals in need thereof a pharmacologically active and therapeutically effective and tolerable amount of one or more of the compounds according to this invention.

The present invention further includes a method useful to modulate apoptosis and/or aberrant cell growth in the therapy of benign or malignant neoplastic diseases, such as e.g. cancer, comprising administering to a subject in need of such therapy a therapeutically active and pharmacologically effective and tolerable amount of one or more of the compounds according to this invention.

The present invention further relates to the use of the compounds according to this invention for the production of pharmaceutical compositions which are employed for the treatment, prophylaxis and/or amelioration of the illnesses mentioned.

The present invention further relates to the use of the compounds according to this invention for the production of pharmaceutical compositions which can be used in the treatment, prevention or amelioration of (hyper)proliferative diseases of benign or malignant behaviour and/or disorders responsive to the induction of apoptosis in a mammal, such as, for example, benign or malignant neoplasia, e.g. cancer.

The present invention further relates to the use of the compounds according to this invention for the production of pharmaceutical compositions which can be used use in the treatment, prevention or amelioration of disorders responsive to arresting of aberrant cell growth and/or induction of apoptosis.

The present invention further relates to the use of the compounds according to this invention for the production of pharmaceutical compositions for treating, preventing or ameliorating benign or malignant neoplasia, particularly cancer, such as e.g. any of those cancer diseases described above.

The present invention further relates to pharmaceutical compositions comprising one or more of the compounds according to this invention and a pharmaceutically acceptable carrier or diluent.

The present invention further relates to pharmaceutical compositions made by combining one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

The present invention further relates to combinations comprising one or more compounds according to this invention and pharmaceutically acceptable auxiliaries, excipients and/or vehicles, e.g. for treating, preventing or ameliorating benign or malignant neoplasia, particularly cancer, such as e.g. any of those cancer diseases described above.

The present invention further relates to a combination comprising a compound according to this invention and a pharmaceutically acceptable excipient, carrier and/or diluent, e.g. for treating, preventing or ameliorating benign or malignant neoplasia, particularly cancer, such as e.g. any of those cancer diseases described above.

The present invention further relates to a composition consisting essentially of a therapeutically effective and tolerable amount of one or more compounds according to this invention together with the usual pharmaceutically acceptable vehicles, diluents and/or excipients for use in therapy, e.g. for treating, preventing or ameliorating hyperproliferative diseases, such as e.g. cancer, and/or disorders responsive to induction of apoptosis.

The present invention further relates to compounds according to this invention for use in therapy, such as, for example, in the treatment, prevention or amelioration (hyper)proliferative diseases of benign or malignant behaviour and/or disorders responsive to the induction of apoptosis, such as e.g. those diseases mentioned herein, particularly cancer.

The present invention further relates to compounds according to this invention having anti-proliferative and/or apoptosis inducing activity.

The present invention further relates to pharmaceutical compositions according to this invention having anti-proliferative activity.

The present invention further relates to pharmaceutical compositions according to this invention having apoptosis inducing activity.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

Additionally, the invention relates to an article of manufacture, which comprises packaging material and a pharmaceutical agent contained within said packaging material, wherein the pharmaceutical agent is therapeutically effective inhibiting cellular (hyper)proliferation and/or inducing apoptosis, ameliorating the symptoms of a (hyper)proliferative disease and/or a disorder responsive to the induction of apoptosis, and wherein the packaging material comprises a label or package insert which indicates that the pharmaceutical agent is useful for treating, preventing or ameliorating a (hyper)proliferative disease and/or a disorder responsive to the induction of apoptosis, and wherein said pharmaceutical agent comprises one or more compounds according to the invention. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, dragees, pills, cachets, granules, capsules, caplets, suppositories, patches (e.g. as TTS), emulsions (such as e.g. micro-emulsions or lipid emulsions), suspensions (such as e.g. nano suspensions), gels, solubilisates or solutions (e.g. sterile solutions), or encapsuled in liposomes or as beta-cyclodextrine inclusion complexes or the like, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, pre-servatives, solubilizers (such as e.g. polyoxyethylenglyceroltriricinoleat 35, PEG 400, Tween 80 or the like), colorants, complexing agents, permeation promoters, stabilizers, fillers, binders, thickeners, disintegrating agents, buffers, pH regulators (e.g. to obtain neutral, alkaline or acidic formulations), polymers, lubricants, coating agents, propellants, tonicity adjusting agents, surfactants, flavorings, sweeteners or dyes, can be used.

In particular, auxiliaries and/or excipients of a type appropriate to the desired formulation and the desired mode of administration are used.

The administration of the compounds, pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, the compounds of the invention can be in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, lotions, pastes, gels or solutions.

The pharmaceutical compositions according to the invention are prepared by processes known per se. The dosage of the compounds of the invention (=active compounds) is carried out in the order of magnitude customary for inhibitors of cellular (hyper)proliferation or apoptosis inducers. Topical application forms (such as ointments) for the treatment of dermatoses thus contain the active compounds in a concentration of, for example, 0.1-99%. The customary dose in the case of systemic therapy (p.o.) may be between 0.03 and 60 mg/kg per day, (i. v.) may be between 0.03 and 60 mg/kg/h. In another embodiment, the customary dose in the case of systemic therapy (p.o.) is between 0.3 and 30 mg/kg per day, (i. v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

For example, compounds according to this invention may be combined with one or more standard therapeutic agents used for treatment of the diseases as mentioned before.

In one particular embodiment, compounds according to this invention may be combined with one or more art-known ant-cancer agents, such as e.g. with one or more chemotherapeutic and/or target specific anti-cancer agents as described below.

Examples of known chemotherapeutic anti-cancer agents frequently used in combination therapy include, but not are limited to (i) alkylating/carbamylating agents such as Cyclophosphamid (Endoxan®), Ifosfamid (Holoxan®), Thiotepa (Thiotepa Lederle®), Melphalan (Alkeran®), or chloroethylnitrosourea (BCNU); (ii) platinum derivatives like cis-platin (Platinex® BMS), oxaliplatin or carboplatin (Cabroplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof, epothilones such as Epothilone B (Patupilone®), Aza-epothilone (Ixabepilone®) or ZK-EPO, a fully synthetic epothilone B analog; (iv) topoisomerase inhibitors such as anthracyclines (exemplified by Doxorubicin/Adriblastin®), epipodophyllotoxines (exemplified by Etoposide/Etopophos®) and camptothecin and camptothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) or premetrexed (Alimta®).

Examples of target specific anti-cancer drug classes used in experimental or standard cancer therapy include but are not limited to (i) kinase inhibitors such as e.g. Imatinib (Glivec®), ZD-1839/Gefitinib (Iressa®), Bay43-9006 (Sorafenib), SU11248/Sunitinib (Sutent®) or OSI-774/Erlotinib (Tarceva®); (ii) proteasome inhibitors such as PS-341/Bortezumib (Velcade®); (iii) histone deacetylase inhibitors like SAHA, PXD101, MS275, MGCD0103, Depsipeptide/FK228, NVP-LBH589, NVP-LAQ824, Valproic acid (VPA) and butyrates (iv) heat shock protein 90 inhibitors like 17-allylaminogeldanamycin (17-AAG); (v) vascular targeting agents (VTAs) like combretastin A4 phosphate or AVE8062/AC7700 and anti-angiogenic drugs like the VEGF antibodies, such as Bevacizumab (Avastin®), or KDR tyrosine kinase inhibitors such as PTK787/ZK222584 (Vatalanib); (vi) monoclonal antibodies such as Trastuzumab (Herceptin®) or Rituximab (MabThera/Rituxan®) or Alemtuzumab (Campath®) or Tositumab (Bexxar®) or C225/Cetuximab (Erbitux®) or Avastin (see above) as well as mutants and conjugates of monoclonal antibodies, e.g. Gemtuzumab ozogamicin (Mylotarg®) or Ibritumomab tiuxetan (Zevalin®), and antibody fragments; (vii) oligonucleotide based therapeutics like G-3139/Oblimersen (Genasense®); (viii) Toll-like receptor/TLR 9 agonists like Promune®, TLR 7 agonists like Imiquimod (Aldara®) or Isatoribine and analogues thereof, or TLR 7/8 agonists like Resiquimod as well as immunostimulatory RNA as TLR 7/8 agonists; (ix) protease inhibitors (x) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors.

Other known target specific anti-cancer agents which may be used for combination therapy include bleomycin, retinoids such as all-trans retinoic acid (ATRA), DNA methyltransferase inhibitors such as the 2-deoxycytidine derivative Decitabine (Docagen®) and 5-Azacytidine, alanosine, cytokines such as interleukin-2, interferons such as interferon $\alpha 2$ or interferon-$\gamma$, death receptor agonists, such as TRAIL, DR4/5 agonistic antibodies, FasL and TNF-R agonists.

As exemplary anti-cancer agents, which may be useful in the combination therapy according to the present invention, any of the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAM-BUCIL, CHLORMETHINE, CISPLATIN, CLADRIBINE, CLOMIFENE, CYCLOPHOSPHAMIDE, DACARBAZINE, DACLIZUMAB, DACTINOMYCIN, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LETROZOLE, LEUPRORELIN, LOBAPLATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALI-PLATIN, PACLITAXEL, PALIVIZUMAB, PATUPILONE, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VERTEPORFIN, VINBLASTINE, VINCRISTINE, VINDESINE, VINORELBINE, VOROZOLE and ZEVALIN.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware on the base of his/her expert knowledge of the kind, total daily dosage(s) and administration form(s) of the additional therapeutic agent(s) coadministered. Said total daily dosage(s) can vary within a wide range.

In practicing the present invention, the compounds according to this invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics, in particular art-known anti-cancer agents (chemotherapeutic and/or target specific anti-cancer agents), such as e.g. any of those mentioned above.

In this context, the present invention further relates to a combination comprising a first active ingredient, which is at least one compound according to this invention, and a second active ingredient, which is at least one art-known anti-cancer agent, such as e.g. one or more of those mentioned herein above, for separate, sequential, simultaneous, concurrent or chronologically staggered use in therapy, such as e.g. in therapy of any of those diseases mentioned herein.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously, concurrently or chronologically staggered.

The present invention further relates to a pharmaceutical composition comprising a first active ingredient, which is at least one compound according to this invention, and a second active ingredient, which is at least one art-known ant-cancer agent, such as e.g. one or more of those mentioned herein above, and, optionally, a pharmaceutically acceptable carrier or diluent, for separate, sequential, simultaneous, concurrent or chronologically staggered use in therapy.

The present invention further relates to a combination product comprising a.) at least one compound according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat (hyper)proliferative diseases and/or disorders responsive to the induction of apoptosis, such as e.g. cancer, more precisely, any of those cancer diseases described above.

The present invention further relates to a combined preparation comprising at least one compound according to this invention and at least one art-known anti-cancer agent for simultaneous, concurrent, sequential or separate administration.

In this connection, the present invention further relates to combinations, compositions, formulations, preparations or kits according to the present invention having anti-proliferative and/or apoptosis inducing properties.

In addition, the present invention further relates to a method for treating in combination therapy (hyper)proliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating (hyper)proliferative diseases of benign or malignant behaviour and/or disorders responsive to the induction of apoptosis, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anticancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing, or ameliorating (hyper)proliferative diseases, such as e.g. cancer, and/or disorders responsive to the induction of apoptosis, particularly those diseases mentioned herein, such as e.g. malignant or benign neoplasia.

The present invention further relates to a commercial package comprising one or more compounds of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a (hyper)proliferative diseases and/or a disorder responsive to the induction of apoptosis, particularly one of those diseases mentioned herein, e.g. benign or malignant neoplasia, especially cancer, like any of those cancer diseases mentioned herein.

In addition, compounds according to the present invention can be used in the pre- or post-surgical treatment of cancer.

In further addition, compounds of the present invention can be used in combination with radiation therapy.

A combination according to this invention can refer to a composition comprising both the compound(s) according to this invention and the other active anti-cancer agent(s) in a fixed combination (fixed unit dosage form), or a medicament pack comprising the two or more active ingredients as discrete separate dosage forms (non-fixed combination). In case of a medicament pack comprising the two or more active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

Biological Investigations

The anti-proliferative/cytotoxic activity of the compounds described herein, can be tested on subclones of RKO (RKOp27) human colon adenocarcinoma cells (Schmidt et al., Oncogene 19, 2423-2429; 2000) using the Alamar Blue cell viability assay (described in O'Brien et al. Eur J Biochem 267, 5421-5426, 2000). The compounds are dissolved as 20 mM solutions in dimethylsulfoxide (DMSO) and subsequently diluted in semi-logarithmic steps. DMSO dilutions are further diluted 1:100 into Dulbecco's modified Eagle's medium (DMEM) containing 10% fetal calf serum to a final concentration twice as much as the final concentration in the test. RKO subclones are seeded into 96 well flat bottom plates at a density of 5000 cells per well in a volume of 50 µl per well. 24 hours after seeding the 50 µl each of the compound dilutions in DMEM medium are added into each well of the 96 Well plate. Each compound dilution is tested as quadruplicates. Wells containing untreated control cells are filled with 50 µl DMEM medium containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values.

The corresponding $IC_{50}$ values of the compounds for anti-proliferative/cytotoxic activity are determined from the concentration-effect curves.

Representative $IC_{50}$ values for anti-proliferation/cytotoxicity determined in the mentioned assay follow from the following table A, in which the numbers of the compounds correspond to the numbers of the examples.

overexpress certain classes of multidrug resistance transporters are used in Alamar Blue assays as described above. Briefly, the compounds are dissolved as 20 mM solutions in dimethylsulfoxide (DMSO) and subsequently diluted in semi-logarithmic steps. DMSO dilutions were further diluted 1:100 into Dulbecco's modified Eagle's medium (DMEM) containing 10% fetal calf serum to a final concentration twice as much as the final concentration in the test. The cells to be tested are seeded into 96 well flat bottom plates at a density of 10000 cells per well in a volume of 50 µl per well. 24 hours after seeding the 50 µl each of the compound dilutions in DMEM medium are added into each well of the 96 Well plate. Each compound dilution is tested as quadruplicates. Wells containing untreated control cells are filled with 50 µl DMEM medium containing 1% DMSO.

The cells are then incubated with the substances for 72 hours at 37° C. in a humidified atmosphere containing 5% carbon dioxide. To determine the viability of the cells, 10 µl of an Alamar Blue solution (Biosource) are added and the fluorescence was measured at an extinction of 544 nm and an emission of 590 nm. For the calculation of the cell viability the emission value from untreated cells is set as 100% viabil-

TABLE A

| | Anti-proliferative/cytotoxic activity | | |
|---|---|---|---|
| | $IC_{50}$ RKO p27 induced (arrested) >100 µM | $IC_{50}$ RKO p27 induced (arrested) ≧40 µM | $IC_{50}$ RKO p27 induced (arrested) ≧10 µM |
| $IC_{50}$ RKO p27 uninduced (proliferating) ≦0.3 µM | 2, 3, 4, 7, 9, 10, 11, 12, 13, 14, 15, 16, 20, 22, 23, 24, 28, 30, 38, 39, 41, 53 | 37 | 34, 35 |
| $IC_{50}$ RKO p27 uninduced (proliferating) ≧0.3 µM but ≦2 µM | 1, 5, 18, 19, 21, 25, 26, 27, 29, 31, 58 | 17, 40, 43 | 32, 33, 36, 42, 45 |

To determine the cell cycle specific mode of action, subclones of RKO colon adenocarcinoma cells (RKOp27 or RKOp21 as described by Schmidt et al. in Oncogene 19, 2423-2429; 2000) are seeded into 96 well flat bottom plates at a density of 15000 cells per well in a volume of 50 µl per well in DMEM growth medium with 10% FCS containing 10 µM Ponasterone A. 24 hours after seeding the 50 µl each of the compound dilutions in DMEM medium are added into each well of the 96 Well plate. Each compound dilution is tested as quadruplicates. Wells containing untreated control cells are filled with 50 µl DMEM medium containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence was measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values. Viability is compared of proliferating cells grown in the absence of the inducer Ponasterone A, versus viability of cells arrested by the expression of ectopic p27Kip1 induced by Ponasterone A.

To test the anti-proliferative activity/cytotoxicity on cells known to be highly resistant towards distinct classes of chemotherapeutics, HCT15 cells (with P-glycoprotein overexpression) and MCF7 ADR cells, both of them are known to ity and the emission rates of treated cells are set in relation to the values of untreated cells. Viabilities are expressed as % values.

The induction of apoptosis can be measured by using a Cell death detection ELISA (Roche Biochemicals, Mannheim, Germany). RKO subclones are seeded into 96 well flat bottom plates at a density of 10000 cells per well in a volume of 50 µl per well. 24 hours after seeding the 50 µl each of the compound dilutions in DMEM medium are added into each well of the 96 Well plate. Each compound dilution is tested at least as triplicates. Wells containing untreated control cells are filled with 50 µl DMEM medium containing 1% DMSO. The cells are then incubated with the substances for 24 hours at 37° C. in a humidified atmosphere containing 5% carbon dioxide. As a positive control for the induction of apoptosis, cells are treated with 50 µM Cisplatin (Gry Pharmaceuticals, Kirchzarten, Germany). Medium is then removed and the cells are lysed in 200 µl lysis buffer. After centrifugation as described by the manufacturer, 10 µl of cell lysate is processed as described in the protocol. The degree of apoptosis is calculated as follows: The absorbance at 405 nm obtained with lysates from cells treated with 50 µM cisplatin is set as 100 cpu (cisplatin units), while an absorbance at 405 nm of 0.0 was set as 0.0 cpu. The degree of apoptosis is expressed as cpu in relation to the value of 100 cpu reached with the lysates obtained from cells treated with 50 µM cisplatin.

The invention claimed is:
1. A compound of formula I

(I)

wherein
Ra is —C(O)R1,
R1 is 1-4C-alkyl, or 1-4C-alkyl substituted by one to four substituents independently selected from R2,
Rb is -T-Q, in which
T is 1-6C-alkylene or 3-7C-cycloalkylene,
Q is optionally substituted by Rca and/or Rcb, and is Har,
each R2 is the same or different and is independently selected from the group consisting of:
3-7C-cycloalkyl, phenyl, Har, Het,
halogen, trifluoromethyl, nitro, cyano,
—C(O)R3, —C(O)OR4, —C(O)N(R5)R6, —S(O)$_2$R3, —S(O)$_2$N(R5)R6,
—N(R7)C(O)R3, —N(R7)C(O)OR4, —N(R7)C(O)N(R5)R6, guanidino,
—OC(O)R3,
completely or predominantly fluorine-substituted 1-4C-alkoxy,
—O[C(R8)R9]$_y$N(R5)R6, —O[C(R8)R9]$_y$C(O)N(R5)R6,
—OR4, hydroxy-2-4C-alkoxy, 1-4C-alkoxy-2-4C-alkoxy, pyridyl-1-4C-alkoxy, (1-4C-alkoxy-2-4C-alkoxy)-2-4C-alkoxy, —N(R5)R6, and —SR3,
wherein each of said 3-7C-cycloalkyl, phenyl, Har and Het is optionally substituted by one to four substituents independently selected from R10,
each R3, R4, R5 and R6 is the same or different and is each independently selected from the group consisting of:
hydrogen, 1-7C-alkyl, 3-7C-cycloalkyl, phenyl, and phenyl-1-4C-alkyl,
each R7 is the same or different and is independently selected from the group consisting of:
hydrogen, 1-7C-alkyl, and 3-7C-cycloalkyl,
each R8 and R9 is the same or different and is each independently selected from the group consisting of:
hydrogen, and 1-4C-alkyl,
each R10 is the same or different is independently selected from the group consisting of:
1-4C-alkyl, phenyl,
halogen, trifluoromethyl, cyano,
1-4C-alkoxycarbonyl, carboxyl,
hydroxyl, and phenoxy,
wherein each of said phenyl and phenoxy radicals can be unsubstituted or optionally substituted by up to four halogen radicals and up to two 1-4C-alkyl, hydroxyl, trifluoromethyl or cyano radicals,
each y is 1, 2, 3 or 4,
each Rca, and Rcb is the same or different and is each independently selected from the group consisting of:
1-4C-alkyl, phenyl,
halogen, trifluoromethyl, cyano,
1-4C-alkoxycarbonyl, carboxyl,
hydroxyl, and phenoxy,
wherein each of said phenyl and phenoxy can be unsubstituted or optionally substituted by up to four halogen radicals and up to two 1-4C-alkyl, hydroxyl, trifluoromethyl or cyano radicals, each Har is the same or different and is independently a fully aromatic or partially aromatic mono- or fused bicyclic ring or ring system, which contains at least one heteroatom in the ring or ring system, made up of
a first constituent being a 5- or 6-member monocyclic unsaturated, aromatic heteroaryl ring A,
which heteroaryl ring A comprises one to four heteroatoms independently selected from the group consisting of nitrogen, oxygen and sulfur,
and, optionally, fused to said first constituent,
a second constituent being a benzene ring, a 5-6C-cycloalkane ring, an additional heteroaryl ring A as defined herein afore, or a heterocyclic ring B,
whereby said Har is attached via a substitutable ring carbon or ring nitrogen atom of Har,
each Het is the same or different and is independently a fully saturated or partially unsaturated mono- or fused bicyclic ring or ring system made up of
a first constituent being a 3- to 7-membered monocyclic fully saturated or partially unsaturated, non-aromatic heterocyclic ring B,
which heterocyclic ring B comprises one to three heteroatoms independently selected from the group consisting of nitrogen, oxygen and sulfur,
and which heterocyclic ring B is optionally substituted by one or two oxo groups,
and, optionally, fused to said first constituent,
a second constituent being a benzene ring, a 3-7C-cycloalkane ring, or an additional heterocyclic ring B as defined herein afore,
wherein said Het is attached via a substitutable ring carbon or ring nitrogen atom;
under the proviso, that
(6-acetyl-3-cyano-4,5,6,7-tetrahydro-thieno[2,3-c]pyridin-2-yl)-3-phenyl-propionamide is disclaimed;
or a salt thereof.

2. A compound according to claim 1, which is a compound of one of the formulae Ia, Ib, Ic, Id and Id'

(Ia)

(Ib)

(Ic)

(Id)

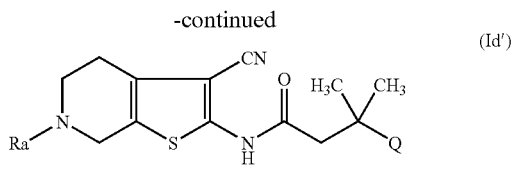

wherein
Ra is —C(O)R1,
R1 is 1-4C-alkyl, or 1-C-alkyl substituted by one or two substituents independently selected from R2,
Q is optionally substituted by Rca and/or Rcb, and is Har,
each R2 is the same or different and is independently selected from the group consisting of:
  Har, Het,
  —C(O)R3, —C(O)OR4, —C(O)N(R5)R6,
  —N(R7)C(O)R3, —OC(O)R3,
  —OR4, hydroxy-2-4C-alkoxy, 1-4C-alkoxy-2-4C-alkoxy, pyridyl-1-4C-alkoxy, (1-4C-alkoxy-2-4C-alkoxy)-2-4C-alkoxy, and phenyl-1-4C-alkoxy,
  wherein each of said Har and Het is optionally substituted by one or two substituents independently selected from R10,
each R3, R4, R5 and R6 is the same or different and is each independently selected from the group consisting of:
  hydrogen, and 1-4C-alkyl,
each R7 is the same or different and is independently selected from the group consisting of:
  hydrogen, and 1-4C-alkyl,
each R10 is the same or different is independently selected from the group consisting of:
  1-4C-alkyl, halogen, trifluoromethyl, cyano,
  1-4C-alkoxycarbonyl, carboxyl, and
  hydroxyl,
each Rca and Rcb is the same or different and is each independently selected from the group consisting of:
  1-4C-alkyl, halogen, trifluoromethyl, cyano,
  1-4C-alkoxycarbonyl, carboxyl, and
  hydroxyl,
each Har is the same or different and is independently
  a 5-membered monocyclic heteroaryl radical comprising one heteroatom independently selected from the group consisting of nitrogen, oxygen and sulphur,
    wherein said Har is attached via a ring carbon or ring nitrogen atom of Har,
  or
  a 6-membered monocyclic heteroaryl radical comprising one or two nitrogen atoms,
    whereby said Har is attached via a ring carbon atom of Har,
Het is a 3- to 7-membered monocyclic fully saturated heterocyclic ring comprising one or two heteroatoms independently selected from the group consisting of nitrogen, oxygen and sulphur,
    whereby said Het is attached via a ring carbon or ring nitrogen atom;
or salt thereof.

3. A compound according to claim 1, which is a compound of one of the formulae Ia, Ib, Ic, Id and Id'

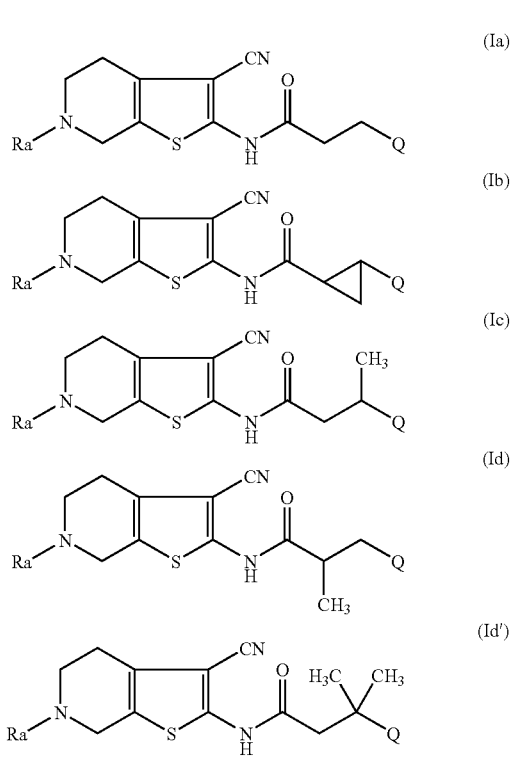

wherein
Ra is —C(O)R1,
R1 is 1-4C-alkyl, 1-4C-alkyl substituted by one substituent selected from R2, or 3-4C-alkyl substituted by two hydroxyl radicals on different carbon atoms,
Q is optionally substituted by Rca and/or Rcb, and is pyridinyl, furanyl, thiophenyl, pyrrolyl, pyrazolyl, thiazolyl, oxazolyl or imidazolyl,
each R2 is the same or different and is independently selected from the group consisting of:
  Har, morpholino, 4-methyl-piperazin-1-yl,
  —C(O)R3, —C(O)OR4, —C(O)N(R5)R6,
  —N(R7)C(O)R3, —OC(O)R3,
  —OR4, hydroxy-2-4C-alkoxy, 1-4C-alkoxy-2-4C-alkoxy, pyridyl-1-4C-alkoxy, phenyl-1-4C-akoxy, and (1-4C-alkoxy-2-4C-alkoxy)-2-4C-alkoxy,
  wherein said Har is optionally substituted by one or two substituents independently selected from R10,
each R3, R4, R5 and R6 is the same or different and is each independently selected from the group consisting of:
  hydrogen, and 1-4C-alkyl,
R7 is hydrogen,
Har is bonded via a ring carbon atom or a ring nitrogen atom of Har, and is imidazolyl, pyrazolyl or triazolyl,
or
Har is bonded via a ring carbon atom of Har, and is pyridinyl, pyrazinyl or pyrimidinyl,
R10 is 1-4C-alkyl,
each Rca and Rcb is the same or different and is each independently selected from the group consisting of:
  1-4C-alkyl, fluorine, chlorine, trifluoromethyl, and cyano;
or a salt thereof.

4. A compound according to claim 1, which is a compound of one of the formulae Ia, Ib and Ic

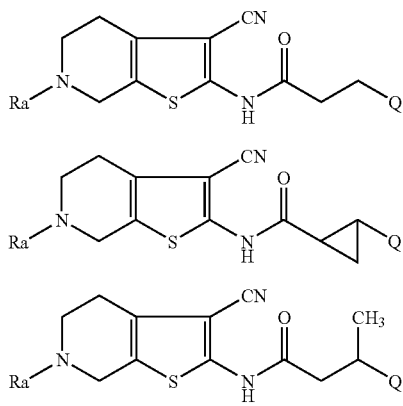

wherein
Ra is —C(O)R1,
R1 is 1-4C-alkyl,
or
1-4C-alkyl which is substituted by one substituent selected from R2,
or
1-2C-alkyl which is substituted by 2,2-dimethyl-[1,3]dioxolan-4-yl,
or
3-4C-alkyl which is substituted by two hydroxyl radicals on different carbon atoms,
Q is optionally substituted by Rca and/or Rcb, and is pyridinyl, furanyl, thiophenyl or pyrazol-1-yl,
each R2 is the same or different and is independently selected from the group consisting of:
pyridyl, pyrimidinyl, R201- and/or R202-substituted pyridyl, R201- and/or R202-substituted pyrimidinyl, morpholino, imidazol-1-yl, pyrazol-1-yl, mono- or di-(R201)-substituted imidazol-1-yl, mono- or di-(R201)-substituted pyrazol-1-yl, 1N-(1-4C-alkyl)-imidazolyl, 1N-(1-4C-alkyl)-pyrazol -1-yl, R201-substituted 1N-(1-4C-alkyl)-imidazolyl, R201-substituted 1N-(1-4C-alkyl)-pyrazol-1-yl, 1N-(H)-imidazolyl, 1N-(H)-pyrazol-1-yl, R201-substituted 1N-(H)-imidazolyl, R201-substituted 1N-(H)-pyrazol-1-yl,
—C(O)OR4, —OC(O)R3,
—OR4,
phenyl-1-2C-alkoxy,
1-2C-alkoxy-2-3C-alkoxy, and
(1-2C-alkoxy-2-3C-alkoxy)-2-3C-alkoxy,
R3 is 1-4C-alkyl,
each R4 is the same or different and is independently selected from the group consisting of: hydrogen, and 1-4C-alkyl,
R201 is 1-4C-alkyl,
R202 is 1-4C-alkyl,
each Rca and Rcb is the same or different and is each independently selected from the group consisting of:
methyl, ethyl, fluorine, chlorine, and trifluoromethyl;
or a salt thereof.

5. A compound according to claim 1, which is a compound of one of the formulae Ia, Ib and Ic

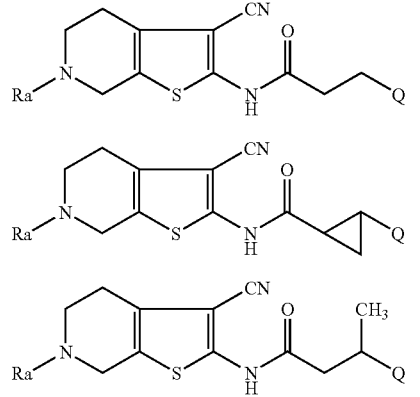

wherein
Ra is —C(O)R1, in which
R1 is methyl, ethyl or propyl,
or
R1 is (R2)-methyl, 2-(R2)-ethyl, or 3-(R2)-propyl,
or
R1 is 2,3-dihydroxypropyl,
Q is unsubstituted, and is pyridinyl, furanyl or thiophenyl,
or
Q is substituted by Rca and/or Rcb, and is pyridinyl, furanyl or thiophenyl,
each R2 is the same or different and is independently selected from the group consisting of:
pyridyl, pyrimidinyl, methybsubstituted pyridyl, imidazol-1-yl, mono- or di-methyl-substituted imidazol-1-yl, 1N-methyl-imidazolyl, carboxyl methoxycarbonyl, hydroxyl, methylcarbonyloxy, methoxy, ethoxy, benzyloxy, and 2-methoxyethoxy,
each Rca and Rcb is the same or different and is each independently selected from the group consisting of:
methyl, ethyl and chlorine;
or a salt thereof.

6. A compound according to claim 1, which is a compound of one of the formulae Ia, Ib and Ic

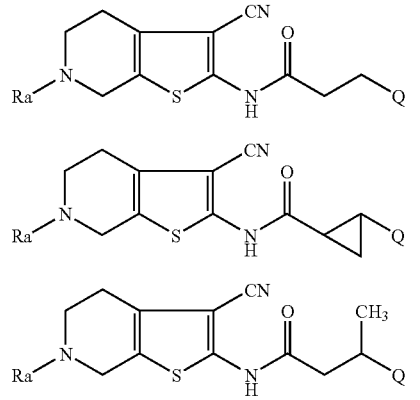

wherein
Ra is —C(O)R1,
R1 is (R2)-methyl, or 2-(R2)-ethyl, in which
R2 is pyridyl,
or
R1is (R2)-methyl, in which R2 is 1N-methyl-imidazolyl,
or
R1 is (R2)-methyl, or 2-(R2)-ethyl, in which
R2 is hydroxyl or methoxy,
or
R1 is (2-methoxyethoxy)-methyl,
or
R1 is (R2)-methyl, or 2-(R2)-ethyl, in which
R2 is imidazol-1-yl, or mono- or di-methyl-substituted imidazol-1-yl;
Q is unsubstituted, and is pyridinyl,
or
Q is unsubstituted, and is furanyl,
or
Q is unsubstituted, and is thiophenyl,
or
Q is 5-(Rca)-furan-2-yl, in which
Rca is methyl or chlorine,
or
Q 5-(Rca)-4-(Rcb)-furan-2-yl, in which
Rca is methyl or chlorine,
Rcb is methyl,
or
Q is 5-(Rca)-thiophen-2-yl, in which
Rca is methyl or chlorine,
or a salt thereof.

7. A compound according to claim 1, which is a compound of one of the formulae Ia, Ib and Ic

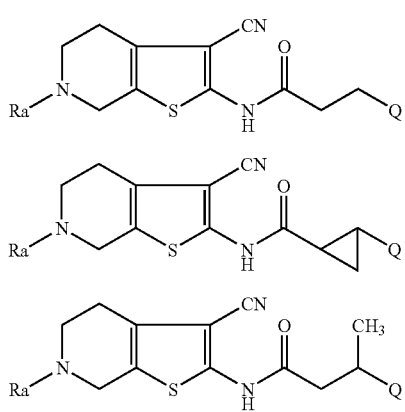

wherein
Ra is —C(O)R1,
R1 is (R2)-methyl, or 2-(R2)-ethyl, in which
R2 is pyridin-2-yl, pyridin-3-yl or pyridin-4-yl,
or
R1 is (R2)-methyl, in which
R2 is 1-methyl-imidazol-2-yl or 1-methyl-imidazol-5-yl,
or
R1 is (R2)-methyl, or 2-(R2)-ethyl, in which
R2 is hydroxyl,
or
R1 is (R2)-methyl, or 2(R2)-ethyl, in which
R2 is imidazol-1-yl, 2-methyl-imidazol-1-yl, 4-methyl-imidazol-1-yl or 2,4-dimethyl-imidazol-1-yl;
Q is unsubstituted, and is pyridin-2-yl,
or
Q is unsubstituted, and is pyridin-3-yl,
or
Q is unsubstituted, and is furan-2-yl,
or
Q is unsubstituted, and is thiophen-2-yl,
or a salt thereof.

8. A compound according to claim 1, which is a compound of one of the formulae Ia, Ib and Ic

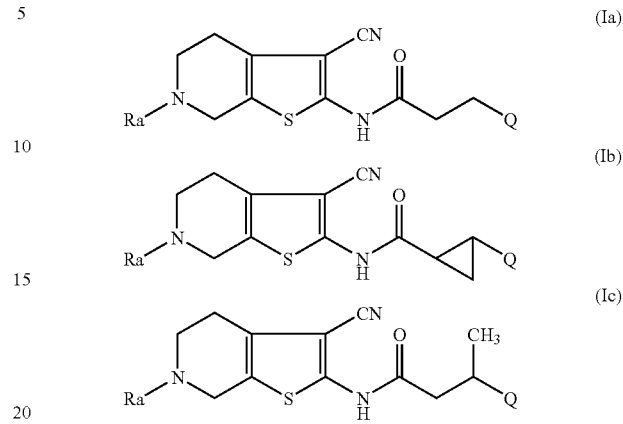

wherein
Ra is —C(O)R1, in which
R1 is (R2)-methyl, or 2-(R2)-ethyl, in which
R2 is pyridin-2-yl, pyridin-3-yl or pyridin-4-yl,
or
R1 is (R2)-methyl, or 2-(R2)-ethyl, in which
R2 is hydroxyl,
or
R1 is (R2)-methyl, or 2-(R2)-ethyl, in which
R2 is imidazol-1-yl;
Q is unsubstituted, and is pyridin-2-yl,
or
Q is unsubstituted, and is pyridin-3-yl,
or
Q is unsubstituted, and is furan-2-yl,
or a salt thereof.

9. A compound according to claim 1, which is a compound of one of the formulae Ia and Ic

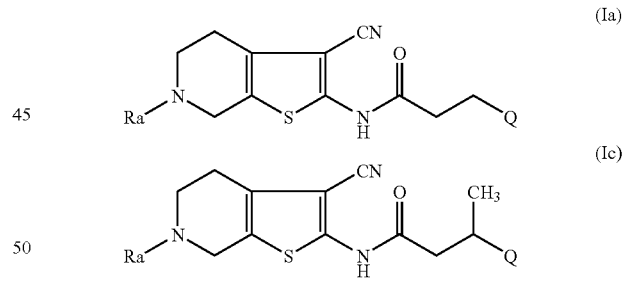

wherein
Ra is —C(O)R1,
R1 is (R2)-methyl, or 2-(R2)-ethyl, in which
R2 is pyridyl,
or
R1 is (R2)-methyl, or 2-(R2)-ethyl, in which
R2 is methoxy,
or
R1 is (2-methoxyethoxy)-methyl,
or
R1 is (R2)-methyl, or 2-(R2)-ethyl, in which
R2 is imidazol-1-yl;
Q is unsubstituted, and is pyridinyl,
or Q is unsubstituted, and is furanyl,
or
Q is unsubstituted, and is thiophenyl,
or
Q is 5-(Rca)-furan-2-yl, in which
Rca is methyl or chlorine,
or
Q 5-(Rca)-4-(Rcb)-furan-2-yl, in which
Rca is methyl or chlorine,
Rcb is methyl,
or
Q is 5-(Rca)-thiophen-2-yl, in which
Rca is methyl or chlorine;
or a salt thereof.

10. A compound according to claim 1, which is a compound of one of the formulae Ia and Ic

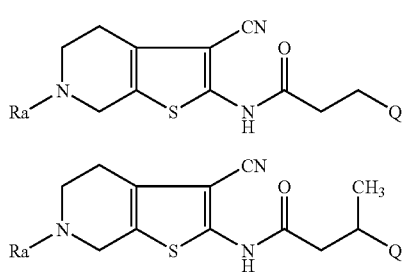

wherein
Ra is —C(O)R1,
R1 is (R2)-methyl, or 2-(R2)-ethyl, in which
R2 is pyridyl,
or
R1 is 2-(R2)-ethyl, in which
R2 is imidazol-1-yl;
Q is unsubstituted, and is pyridin-2-yl,
or
Q is unsubstituted, and is pyridin-3-yl,
or
Q is unsubstituted, and is furan-2-yl,
or
Q is unsubstituted, and is thiophen-2-yl,
or a salt thereof.

11. A compound, which is selected from the group consisting of
N-{3-Cyano-6-[2-(2-methoxy-ethoxy)-ethanoyl]-4,5,6,7-tetrahydro-thieno[2,3-c]pyridin-2-yl}-3-furan-2-yl-propionamide,
N-[3-Cyano-6-(2-pyridin-2-yl-ethanoyl)-4,5,6,7-tetrahydro-thieno[2,3-c]pyridin-2-yl]-3-furan-2-yl -propionamide,
N-(3-Cyano-6-(2-pyridin-3-yl-ethanoyl)-4,5,6,7-tetrahydro-thieno[2,3-c]pyridin-2-yl]-3-furan-2-yl-propionamide,
N-[3-Cyano-6-(3-pyridin-3-yl-propanoyl)-4,5,6,7-tetrahydro-thieno[2,3-c]pyridin-2-yl)-3-furan-2-yl-propionamide,
N-[3-Cyano-6-(2-methoxy-ethanoyl)-4,5,6,7-tetrahydro-thieno[2,3-c]pyridin-2-yl]-3-furan-2-yl-propionamide,
N-(6-Butyryl-3-cyano-4,5,6,7-tetrahydro-thieno[2,3-c]pyridin-2-yl)-3-furan-2-yl-propionamide,
N-[3-Cyano-6-(3-imidazol-1-yl-propanoyl)-4,5,6,7-tetrahydro-thieno[2,3-c]pyridin-2-yl]-3-furan-2-yl-propionamide,
N-[3-Cyano-6-(2-pyridin-4-yl-ethanoyl)-4,5,6,7-tetrahydro-thieno[2,3-c]pyridin-2-yl]-3-furan-2-yl-propionamide,
N-[3-Cyano-6-(3-pyridin-4-yl-propanoyl)-4,5,6,7-tetrahydro-thieno[2,3-c]pyridin-2-yl]-3-furan-2-yl-propionamide,
N-[3-Cyano-6-(3-pyridin-2-yl-propanoyl)-4,5,6,7-tetrahydro-thieno[2,3-c]pyridin-2-yl]-3-furan-2-yl-propionamide,
N-[3-Cyano-6-(2-imidazol-1-yl-ethanoyl)-4,5,6,7-tetrahydro-thieno[2,3-c]pyridin-2-yl]-3-furan-2-yl-propionamide,
N-{3-Cyano-6[3-(1-methyl-1H-imidazol-2-yl)-propanoyl]-4,5,6,7-tetrahydro-thieno[2,3-c]pyridin-2-yl}-3-furan-2-yl-propionamide,
N-[3-Cyano-6-(3-hydroxy-propanoyl)-4,5,6,7-tetrahydro-thieno[2,3-c]pyridin-2-yl]-3-furan-2-yl-propionamide,
N3-Cyano-6-(2-hydroxy-ethanoyl)-4,5,6,7-tetrahydro-thieno[2,3-c]pyridin-2-yl]-3-furan-2-yl-propionamide,
N-[3-Cyano-6-(2-hydroxy-ethanoyl)-4,5,6,7-tetrahydro-thieno[2,3-c]pyridin-2-yl]-3-pyridin-3-yl-propionamide,
N-[3-Cyano-6-(3-hydroxy-propanoyl)-4,5,6,7-tetrahydro-thieno[2,3-c]pyridin-2-yl]-3-pyridin-3-yl-propionamide,
N-[3-Cyano-6-(2-hydroxy-ethanoyl)-4,5,6,7-tetrahyduo-thieno[2,3-c]pyridin-2-yl]-3-pyridin-2-yl-propionamide and
N-[3-Cyano-6-(3-hydroxy-propanoyl)-4,5,6,7-tetrahydro-thieno[2,3-c]pyridin-2-yl]-3-pyridin-2-yl-propionamide,
and salts thereof.

12. An enantiomer of a compound according to claim 1, or a salt thereof.

13. A pharmaceutical composition comprising one or more compounds according to claim 1, together with a pharmaceutically acceptable excipient, diluent and/or carrier.

14. A combination comprising
a first active ingredient, which is at least one compound according to claim 1, and
a second active ingredient, which is at least one anti-cancer agent selected from the group consisting of chemotherapeutic anti-cancer agents and target-specific anti-cancer agents.

15. The combination according to claim 14, in which said chemotherapeutic anti-cancer agents are selected from the group consisting of (i) alkylating/carbamylating agents; (ii) platinum derivatives; (iii) antimitotic agents/tubulin inhibitors; (iv) topoisomerase inhibitors; (v) pyrimidine antagonists; (vi) purin antagonists; and (vii) folic acid antagonists.

16. The combination according to claim 14, in which said target-specific anti-cancer agents are selected from the group consisting of (i) kinase inhibitors; (ii) proteasome inhibitors; (iii) histone deacetylase inhibitors; (iv) heat shock protein 90 inhibitors; (v) vascular targeting agents, anti-angiogenic drugs, and KDR tyrosine kinase inhibitors; (vi) monoclonal antibodies, mutants and conjugates of monoclonal antibodies, and antibody fragments; (vii) oligonucleotide based therapeutics; (viii) Toll-like receptor/TLR 9 agonists, TLR 7 agonists and TLR 7/8 agonists; (ix) protease inhibitors; (x) hormonal therapeutics; (xi) aromatase inhibitors; (xii) bleomycin; (xiii) retinoids; (xiv) DNA methyltransferase inhibitors; (xv) alanosine; (xvi) cytokines; (xvii) interferons; (xviii) death receptor agonists; (xix) DR4/5 agonistic antibodies; (xx) FasL; and (xxi) TNF-R agonists.

* * * * *